United States Patent
Rashid et al.

(10) Patent No.: US 12,404,512 B2
(45) Date of Patent: Sep. 2, 2025

(54) METHOD FOR OPTIMIZING ANTIBODY EXPRESSION

(71) Applicant: Ambrx, Inc., La Jolla, CA (US)

(72) Inventors: Md Harunur Rashid, La Jolla, CA (US); Mark Shimazu, La Jolla, CA (US); Feng Tian, La Jolla, CA (US)

(73) Assignee: Ambrx, Inc., La Jolla, CA (US)

( * ) Notice: Subject to any disclaimer, the term of this patent is extended or adjusted under 35 U.S.C. 154(b) by 1056 days.

(21) Appl. No.: 17/051,690

(22) PCT Filed: May 1, 2019

(86) PCT No.: PCT/US2019/030295
§ 371 (c)(1),
(2) Date: Oct. 29, 2020

(87) PCT Pub. No.: WO2019/213331
PCT Pub. Date: Nov. 7, 2019

(65) Prior Publication Data
US 2021/0108213 A1  Apr. 15, 2021

Related U.S. Application Data

(60) Provisional application No. 62/665,093, filed on May 1, 2018.

(51) Int. Cl.

| | |
|---|---|
| C12N 15/63 | (2006.01) |
| C07K 14/245 | (2006.01) |
| C07K 14/535 | (2006.01) |
| C07K 16/28 | (2006.01) |
| C12N 9/90 | (2006.01) |
| C12N 15/67 | (2006.01) |
| C12N 15/70 | (2006.01) |

(52) U.S. Cl.
CPC ............ *C12N 15/67* (2013.01); *C07K 14/245* (2013.01); *C07K 16/2809* (2013.01); *C12N 9/90* (2013.01); *C07K 2317/522* (2013.01); *C07K 2317/55* (2013.01); *C07K 2317/92* (2013.01); *C12Y 502/01008* (2013.01)

(58) Field of Classification Search
CPC ........... C12N 15/09; C12N 15/10; C12N 1/20
See application file for complete search history.

(56) References Cited

U.S. PATENT DOCUMENTS

| | | |
|---|---|---|
| 4,870,008 A | 9/1989 | Brake |
| 6,673,569 B1 | 1/2004 | Kurokawa |
| 6,927,042 B2 | 8/2005 | Schultz |
| 7,045,337 B2 | 5/2006 | Schultz |
| 7,083,970 B2 | 8/2006 | Schultz |
| 8,119,365 B2 * | 2/2012 | Blattner .............. C12P 21/02 435/252.8 |
| 8,153,758 B2 | 4/2012 | Miao et al. |
| 9,150,849 B2 | 10/2015 | Liu et al. |
| 11,208,497 B2 | 12/2021 | Babcook et al. |
| 11,261,470 B2 | 3/2022 | Bassett et al. |
| 2003/0010885 A1 | 1/2003 | Wayne et al. |
| 2005/0009049 A1 | 1/2005 | Chin |
| 2005/0208536 A1 | 9/2005 | Schultz |
| 2006/0153860 A1 | 7/2006 | Cho et al. |
| 2006/0233744 A1 | 10/2006 | Shultz |
| 2008/0221112 A1 | 9/2008 | Yamamori |

FOREIGN PATENT DOCUMENTS

| | | |
|---|---|---|
| EP | 0786009 B1 | 11/1995 |
| JP | H0759192 B2 | 6/1995 |
| WO | 1987/02670 A1 | 5/1987 |
| WO | 95/21260 A1 | 8/1995 |
| WO | 1998/56930 A2 | 12/1998 |
| WO | 2002/085923 A2 | 10/2002 |
| WO | 2002/086075 A2 | 10/2002 |
| WO | 2004/058946 A2 | 7/2004 |
| WO | 2010/011735 A2 | 7/2004 |
| WO | 2004/094593 A2 | 11/2004 |
| WO | 2005/007624 A2 | 1/2005 |
| WO | 2005/007870 A2 | 1/2005 |
| WO | 2005/019415 A2 | 3/2005 |
| WO | 2005/074650 A2 | 8/2005 |
| WO | WO 2012/106615 A1 | 8/2012 |
| WO | 2019213331 A1 | 11/2019 |

OTHER PUBLICATIONS

Carey, F. & Sundberg, R., Advanced Organic Chemistry, Third Edition, Parts A and B, Plenum Press, New York, 1990.
Matsoukas, et al., J. Med. Chem., 38, 4660-4669, 1995.
King, F. E. & Kidd, D. A. A., A New Synthesis of Glutamine and of gamma-Dipeptides of Glutamic Acid from Phthylated Intermediates, J. Chem. Soc., 3315-3319, 1949.
Friedman, O. M. & Chatterji, R., Synthesis of Derivatives of Glutamine as Model Substrates for Anti-Tumor Agents, J. Am. Chem. Soc. 81, 3750-3752, 1959.
Craig, J. C. et al., Absolute Configuration of the Enantiomers of 7-Chloro-4 [[4-(diethylamino)-1-methylbutyl]amino] quinoline (Chloroquine), J. Org. Chem. 53, 1167-1170, 1988.
Azoulay, M., Vilmont, M. & Frappier, F., Glutamine analogues as Potential Antimalarials, Eur. J. Med. Chem. 26, 201-5, 1991.
Koskinen, A. M. P. & Rapoport, H. Synthesis of 4-Substituted Prolines as Conformationally Constrained Amino Acid Analogues, J. Org. Chem., 54, 1859-1866, 1989.
Christie, B. D. & Rapoport, H., Synthesis of Optically Pure Pipecolates from L-Asparagine. Application to the Total Synthesis of (+)-Apovincamine through Amino Acid Decarbonylation and Iminium Ion Cyclization, J. Org. Chem.:1859-1866, 1985.
Barton, et al., Synthesis of Novel a-Amino-Acids and Derivatives Using Radical Chemistry: Synthesis of L-and D-a-Amino-Adipic Acids, L-a-aminopimelic Acid and Appropriate Unsaturated Derivatives, Tetrahedron Lett, 43:4297-4308, 1987.

(Continued)

*Primary Examiner* — Maryam Monshipouri
(74) *Attorney, Agent, or Firm* — Morrison & Foerster LLP

(57) ABSTRACT

Disclosed herein are methods, compositions and components for optimizing or increasing expression of a protein, polypeptide or fragment therefrom.

22 Claims, 14 Drawing Sheets

Specification includes a Sequence Listing.

(56) References Cited

OTHER PUBLICATIONS

Subasinghe, et al., Quisqualic acid analogues: synthesis of beta-heterocyclic 2-aminopropanoic acid derivatives and their activity at a novel quisqualate-sensitized site, J. Med. Chem. 35:4602-7. 1992.
Dougherty, Unnatural Amino Acids as Probes of Protein Structure and Function, Current Opinion in Chemical Biology, 4:645-652, 2000.
Cornish, et al., J. Am. Chem, Soc., 118:8150-8151, 1996.
Mahal, et al., Science, 276:1125-1128, 1997.
Wang, et al., Science 292: 498-500, 2001.
Chin, et al., J. Am. Chem. Soc. 124:9026-9027, 2002.
Chin, et al., Proc. Natl. Acad. Sci., 99:11020-11024, 2002.
Wang, et al., Proc. Natl. Acad. Sci., 100:56-61, 2003.
Zhang, et al., Biochemistry, 42:6735-6746, 2003.
Chin, et al., Science, 301:964-7, 2003.
Kiick, et al., Incorporation of azides into recombinant proteins for chemoselective modification by the Staudinger ligation, PNAS 99:19-24, 2002.
Palva, et al., Gene 22:229-235, 1983.
Mosbach, et al., Nature 302:543-545, 1983.
Coloma, J. Imm. Methods, 152, 89-104, 1992.
Hagenbuchle, et al., Nature 289, 643-646, 1981.
Valls, et al., Cell 48, 887-897, 1987.
Javahishvili, T., et al., ACS Chem Biol. 9(4): 874-879, 2014.
https://go.drugbank.com/drugs/DB01270.
Miot, M. & Betton, J.M., Microbial Cell Factories, 3, 4, 2004.
Yoon, S. H. et al., Recent Patents in Biotech, 4, 23, 2010.
Thomas, et al., Applied Biochemistry and Biotechnology, 66, 197, 1997.
Kolaj, et. al., Microbial Cell Factories, 8, 2009.
Merdanovic, et. al., Annu. Rev. Microbiol. 65, 149, 2011.
Maynard & Georgiou, Annu. Rev. Biomed. Eng. 2:339-76, 2000.
Hudson, Curr. Opin. Biotechnol. 9:395-402, 1998.
Hu, et al., Cancer Research, 56, 3055-3061, 1996.
Gillam & Smith, Gene 8:81, 1979.
Batzer, et al., Nucleic Acid Res. 19:5081, 1991.
Ohtsuka, et al., J. Biol. Chem. 260:2605-2608, 1985.
Rossolini, et al., Mol. Cell. Probes 8:91-98, 1994.
Schneider, E., et al., Protein Expr. Purif. 6(1):10-14, Ausubel, Sambrook, Berger, 1995.
Roberts, et al., Nature, 328:731, 1987.
Cohen, et al., Proc. Natl. Acad. Sci. USA 69, 2110, 1972.
Chen, C. et al., Biotechnology and Bioengineering, 85, 463, 2004.
Battersby, J. E. et. al., Journal of Chromatography A, 927, 61, 2001.
Keiler, K.C. & Sauer, R.T., The Journal of Biological Chemistry, 271, 2589, 1996.
Feige, et al., Mol. Cell 34, 569, 2009.
Hayhurst, et al., Protein Expr. Purif., 15, 336-343, 1999.
Hayhurst, et al., J. Immunol. Meth., 276, 185-196, 2003.
Padiolleau-Lefevre, et al., Immunol. Lett., 103, 39-44, 2006.
Zhang, et al., Biotechniques, 35, 1032-1038. 2003.
Ege-Mitani, et al., Yeast 6, 127-137, 1990.
Raibaud, et al., Annu.Rev.Genet, 18:173, 1984.
Gerdes, K., Nature Biotech. 6, 1402-1405, 1988.
Gerdes, K. et. al., Mol. Microbiol. 4, 1807, 1990.
Gerdes, K. and Neilsen, AI, J. Mol. Biol. 226, 637, 1992.
Keiler et al. Protein Science 4, 1507, 1995.
Keiler, KC and Sauer, RT, The Journal of Biological Chemistry 271, 2589, 1996.
Liu, et al., PNAS 96:4780-4785, 1999.
Wang, and Schultz, "Expanding the Genetic Code," Angewandte Chemie Int. Ed., 44(1):34-66, 2005.
Wang, et al., Proc. Natl. Acad. Sci. USA 100:56-61, 2003.
Zhang, et al., Biochem. 42(22):6735-6746, 2003.
Pastrnak, et al., Helv. Chim. Acta 83:2277-2286, 2000.
Ohno, et al., J. Biochem. (Tokyo, Jpn.) 124:1065-1068, 1998.
Kowal, et al., PNAS 98:2268-2273, 2001.
Edwards, et al., Mol. Cell. Biol. 10:1633-1641,1990.
Sakamoto, et al., Nucleic Acids Res. 30:4692-4699, 2002.
Sayers, J.R., et al. , 5'-3' Exonucleases in phosphorothioate-based oligonucleotide-directed mutagenesis. Nucleic Acids Res, 16:791-802, 1988.
Ma, et al., Biochemistry, 32:7939, 1993.
Kowal and Oliver, Nud. Acid. Res., 25:4685, 1997.
Anderson, et al., Exploring the Limits of Codon and Anticodon Size, Chemistry and Biology, 9:237-244. 2002.
Magliery, Expanding the Genetic Code: Selection of Efficient Suppressors of Four-base Codons and Identification of "Shifty" Four-base Codons with a Library Approach in *Escherichia coli*, J. Mol. Biol. 307: 755-769, 2001.
Hohsaka, et al., J. Am. Chem. Soc., 121(51), pp. 12194-12195, 1999.
Moore, et al., J. Mol. Biol., 298:195, 2000.
Hirao, et al., An unnatural base pair for incorporating amino acid analogues into protein, Nature Biotechnology, 20:177-182, 2002.
Wu, Y., et al., J. Am. Chem. Soc. 124:14626-14630, 2002.
Ebersbach, G. & Gerdes, K., Annu. Rev. Genet. 39, 453, 2005.
March, J., Advanced Organic Chemistry, Third Edition, Wiley and Sons, New York, 1985.
Ow, et. al., "Co-expression of Skp and FkpA chaparones improves cell liability and alters the global expression of stress response genes during scFuD1.3 production", Microbial Cell Factories, vol. 9, No. 1, p. 22, Apr. 13, 2010.
Bothman, H. & Pluckthun, A., "The Periplasmic *Escherichia coli* Peptidylprolyl cis, trans-Isomerase FkpA I. Increased Functional Espression of Antibody Fragments With and Without cis-Prolines", J. Biol. CHem, 2000, 275:17100-17105, originally published on line Mar. 22, 2000.
Schweder, T. et. al., "An expression vector system providing plasmid stability and conditional suicide of plasmid-containing cells", Applied Microbiology and Biotechnology, vol. 38, No. 1, p. 91-93, Oct. 1, 1992.
Gerdes, K. et. al., "Unique type of plasmid maintenance function: postsecregational killing of plasmid-free cells", PSNA, Nat'l Acadamy of Sciences, US, vol. 83, No. 10, p. 3116-3120, May 1, 1986.
Otsuki, T. (Dec. 3, 2007). "Translational Expansion Using Modified EF-Tu," The Chemical Society of Japan News Letter 22(3):1-6.
Rossolini, G.M. et al. (1994). "Use of Deoxyinosine-containing Primers vs Degenerate Primers for Polymerase Chain Reaction Based on Ambiguous Sequence Information," Molecular and Cellular Probes 8:91-98.
Teramoto, H. (Apr. 2017). "Modification of Silk by Introduction of Unnatural Amino Acids: Creation of Clickable Silk," The Japanese Society of Sericultural Science 86(1):25-38.
Bain, J.D. et al. (Dec. 31, 1989). "Biosynthetic Site-Specific Incorporation of a Non-Natural Amino Acid into a Polypeptide," American Chemical Sociery 111(20):8013-8014.
Ohtsuka, E. et al. (Mar. 10, 1985). "An Alternative Approach to Deoxyoligonucleotides as Hybridization Probes by Insertion of Deoxyinosine at Ambiguous Codon Positions,"J. Biol Chem. (260(5):2605-2608.

* cited by examiner

A. Two-plasmid

B. Single-plasmid

SEQUENCE LISTING

```
<160> NUMBER OF SEQ ID NOS: 18

<210> SEQ ID NO 1
<211> LENGTH: 23
<212> TYPE: PRT
<213> ORGANISM: E. Coli

<400> SEQUENCE: 1

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 2
<211> LENGTH: 110
<212> TYPE: PRT
<213> ORGANISM: E. Coli

<400> SEQUENCE: 2

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45
```

```
Leu Ile Gly Gly Thr Asn Lys Arg Ala Pro Gly Thr Pro Ala Arg Phe
 50                  55                  60

Ser Gly Ser Leu Leu Gly Lys Ala Ala Leu Thr Leu Ser Gly Ala
 65              70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly
            100                 105                 110

<210> SEQ ID NO 3
<211> LENGTH: 107
<212> TYPE: PRT
<213> ORGANISM: E. Coli

<400> SEQUENCE: 3

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 4
<211> LENGTH: 125
<212> TYPE: PRT
<213> ORGANISM: E. Coli

<400> SEQUENCE: 4

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Ile
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 5
<211> LENGTH: 103
<212> TYPE: PRT
<213> ORGANISM: E. Coli
```

-continued

```
<220> FEATURE:
<221> NAME/KEY: pAcF
<222> LOCATION: (16)..(16)
<223> OTHER INFORMATION: Unnatural amino acid

<400> SEQUENCE: 5
```

Ala Ser Thr Lys Gly Pro Ser Val Phe Pro Leu Ala Pro Ser Ser Xaa
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

```
<210> SEQ ID NO 6
<211> LENGTH: 69
<212> TYPE: DNA
<213> ORGANISM: E. Coli

<400> SEQUENCE: 6
```
atgaaaaaga atatcgcatt tcttcttgca tctatgttcg ttttttctat tgctacaaac      60
gcgtacgct                                                              69

```
<210> SEQ ID NO 7
<211> LENGTH: 330
<212> TYPE: DNA
<213> ORGANISM: E.Coli

<400> SEQUENCE: 7
```
caggctgtgg tgactcagga gccctcactg actgtgtccc caggagggac agtcactctc      60
acctgtcgct ccagcactgg agctgtcacc actagtaatt atgccaactg gtccagcag      120 aagcctggcc aagcccccag gggactgatt ggtgggacaa acaagagagc tcccgggaca     180
cctgcccggt tctcaggctc cctccttggg gcaaagctg ccctgaccct tcgggtgcg      240 cagcctgagg atgaggctga gtattactgc gctctctggt atagtaatct gtgggtgttc     300
ggcggaggga ccaagttgac cgtcctcgga                                       330

```
<210> SEQ ID NO 8
<211> LENGTH: 321
<212> TYPE: DNA
<213> ORGANISM: E.Coli

<400> SEQUENCE: 8
```
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 9
<211> LENGTH: 32
<212> TYPE: DNA
<213> ORGANISM: E. Coli

<400> SEQUENCE: 9
tctggggata agaattcggt tgaggtgatt tt                            32

<210> SEQ ID NO 10
<211> LENGTH: 375
<212> TYPE: DNA
<213> ORGANISM: E. Coli

<400> SEQUENCE: 10
gaggtgcagc tggtggagtc tgggggaggc ttggtccagc ctggagggtc cctgagactc      60
tcctgtgcag cctctggatt caccttcaat acctacgcaa tgaactgggt ccgccaggct    120
ccagggaagg gctggagtg gttgctcgt attagaagca aatataacaa ttacgccaca     180
tattacgccg attctgtgaa agacagattc accatctcaa gagatgattc aaagaacatt    240
ctgtatctgc aaatgaacag cctgaaaacc gaggacacgg ccgtgtatta ctgtgttaga    300
catgggaatt tcggcaactc ttatgtcagt tggtttgcct actggggcca aggtaccctg    360
gtcaccgtct cgagt                                                    375

<210> SEQ ID NO 11
<211> LENGTH: 309
<212> TYPE: DNA
<213> ORGANISM: E. Coli

<400> SEQUENCE: 11
gctagcacca agggcccatc ggtcttcccc ctggcaccct cctccagag cacctctggg      60 ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgt                                                           309

<210> SEQ ID NO 12
<211> LENGTH: 580
<212> TYPE: DNA
<213> ORGANISM: E. Coli

<400> SEQUENCE: 12
aacaaactcc gggaggcagc gtgatgcggc aacaatcaca cggatttccc gtgaacggtc      60
tgaatgagcg gattattttc agggaaagtg agtgtggtca gcgtgcaggt atatgggcta    120
tgatgtgccc ggcgcttgag gctttctgcc tcatgacgtg aaggtggttt gttgccgtgt    180
tgtgtggcag aaagaagata gccccgtagt aagttaattt tcattaacca ccacgaggca    240
tccctatgtc tagtccacat caggatagcc tcttaccgcg ctttgcgcaa ggagaagaag    300
gccatgaaac taccacgaag ttcccttgtc tggtgtgtgt tgatcgtgtg tctcacactg    360
ttgatattca cttatctgac acgaaaatcg ctgtgcgaga ttcgttacag agacggacac    420
agggaggtgg cggctttcat ggcttacgaa tccggtaagt agcaacctgg aggcgggcgc    480
aggcccgcct tttcaggact gatgctggtc tgactactga agcgccttta taagggggct    540

```
gctggttcgc cggtagcccc tttctccttg ctgatgttgt            580
```

<210> SEQ ID NO 13
<211> LENGTH: 156
<212> TYPE: DNA
<213> ORGANISM: E. Coli

<400> SEQUENCE: 13

```
atgaaactac cacgaagttc ccttgtctgg tgtgtgttga tcgtgtgtct cacactgttg    60
atattcactt atctgacacg aaaatcgctg tgcgagattc gttacagaga cggacacagg   120
gaggtggcgg ctttcatggc ttacgaatcc ggtaag                             156
```

<210> SEQ ID NO 14
<211> LENGTH: 52
<212> TYPE: PRT
<213> ORGANISM: E. Coli

<400> SEQUENCE: 14

```
Met Lys Leu Pro Arg Ser Ser Leu Val Trp Cys Val Leu Ile Val Cys
1               5                  10                  15

Leu Thr Leu Leu Ile Phe Thr Tyr Leu Thr Arg Lys Ser Leu Cys Glu
            20                  25                  30

Ile Arg Tyr Arg Asp Gly His Arg Glu Val Ala Ala Phe Met Ala Tyr
        35                  40                  45

Glu Ser Gly Lys
    50
```

<210> SEQ ID NO 15
<211> LENGTH: 1199
<212> TYPE: DNA
<213> ORGANISM: E. Coli

<400> SEQUENCE: 15

```
gattcacctc ttttgtcgaa tggtcgccgc ggattctact taactttgct gcccgagaca    60
gcactcattt cgcggtcatc gaaactaatt taaacaaaaa gagtctgaaa atagatgata   120
atagggcgtg tctgtatgta gatttgttcg acaacgcttt atagtaccct tctgataata   180
gttaaccctg gggtgagatg ccccgatcct ggagatatgg atgaaatcac tgtttaaagt   240
aacgctgctg cgaccacaa tggccgttgc cctgcatgca ccaatcactt ttgctgctga   300
agctgcaaaa cctgctacag ctgctgacag caaagcagcg ttcaaaaatg acgatcagaa   360
atcagcttat gcactgggtg cctcgctggg tcgttacatg gaaaactctc taaaagaaca   420
agaaaaactg ggcatcaaac tggataaaga tcagctgatc gctggtgttc aggatgcatt   480
tgctgataag agcaaactct ccgaccaaga gatcgaacag actctacaag cattcgaagc   540
tcgcgtgaag tcttctgctc aggcgaagat ggaaaaagac gcggctgata acgaagcaaa   600
aggtaaagag taccgcgaga aatttgccaa agagaaaggt gtgaaaacct cttcaactgg   660
tctggtttat caggtagtag aagccggtaa aggcgaagca ccgaaagaca gcgatactgt   720
tgtagtgaac tacaaaggta cgctgatcga cggtaaagag ttcgacaact cttacacccg   780
tggtgaaccg ctttctttcc gtctggacgg tgttatcccg ggttggacag aaggtctgaa   840
gaacatcaag aaaggcggta agatcaaact ggttattcca ccagaactgg cttacggcaa   900
agcgggtgtt ccggggatcc caccgaattc taccctggtg tttgacgtag agctgctgga   960
tgtgaaacca gcgccgaagg ctgatgcaaa gccggaagct gatgcgaaag ccgcagattc  1020
tgctaaaaaa taagcattaa gaaccgccgc ctgaccaggc ggcggttttt ttattacagg  1080
```

```
ccggatataa ttagtgctgg aaagcggaac ctccgctgta ttaatttagt tacccgcatc   1140
attaatgagc ctgccctgaa aagttaacga caggctcctg aaaaggagtg tttttttttc   1199
```

<210> SEQ ID NO 16
<211> LENGTH: 270
<212> TYPE: PRT
<213> ORGANISM: E. Coli

<400> SEQUENCE: 16

```
Met Lys Ser Leu Phe Lys Val Thr Leu Leu Ala Thr Thr Met Ala Val
1               5                   10                  15

Ala Leu His Ala Pro Ile Thr Phe Ala Ala Glu Ala Ala Lys Pro Ala
            20                  25                  30

Thr Ala Ala Asp Ser Lys Ala Ala Phe Lys Asn Asp Asp Gln Lys Ser
        35                  40                  45

Ala Tyr Ala Leu Gly Ala Ser Leu Gly Arg Tyr Met Glu Asn Ser Leu
    50                  55                  60

Lys Glu Gln Glu Lys Leu Gly Ile Lys Leu Asp Lys Asp Gln Leu Ile
65                  70                  75                  80

Ala Gly Val Gln Asp Ala Phe Ala Asp Lys Ser Lys Leu Ser Asp Gln
                85                  90                  95

Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
        115                 120                 125

Lys Glu Tyr Arg Glu Lys Phe Ala Lys Glu Lys Gly Val Lys Thr Ser
    130                 135                 140

Ser Thr Gly Leu Val Tyr Gln Val Val Glu Ala Gly Lys Gly Glu Ala
145                 150                 155                 160

Pro Lys Asp Ser Asp Thr Val Val Val Asn Tyr Lys Gly Thr Leu Ile
                165                 170                 175

Asp Gly Lys Glu Phe Asp Asn Ser Tyr Thr Arg Gly Glu Pro Leu Ser
            180                 185                 190

Phe Arg Leu Asp Gly Val Ile Pro Gly Trp Thr Glu Gly Leu Lys Asn
        195                 200                 205

Ile Lys Lys Gly Gly Lys Ile Lys Leu Val Ile Pro Pro Glu Leu Ala
    210                 215                 220

Tyr Gly Lys Ala Gly Val Pro Gly Ile Pro Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
            260                 265                 270
```

<210> SEQ ID NO 17
<211> LENGTH: 634
<212> TYPE: DNA
<213> ORGANISM: E. Coli

<400> SEQUENCE: 17

```
tttaacatcg gtaaaacctg gtaagtgttc tccacaaagg aatgtagtgg tagtgtagcg    60
atgactttag gcgatcaata taagatcgcc gggccacgca agaactgca ccctccggtg    120 caaatgggat ggtaaggagt ttattgtgaa aaagtggtta ttagctgcag gtctcggttt    180
agcactggca acttctgctc aggcggctga caaaattgca atcgtcaaca tgggcagcct    240
```

```
gttccagcag gtagcgcaga aaaccggtgt ttctaacacg ctggaaaatg agttcaaagg    300
ccgtgccagc gaactgcagc gtatggaaac cgatctgcag gctaaaatga aaaagctgca    360
gtccatgaaa gcgggcagcg atcgcactaa gctggaaaaa gacgtgatgg ctcagcgcca    420
gacttttgct cagaaagcgc aggcttttga gcaggatcgc gcacgtcgtt ccaacgaaga    480
acgcggcaaa ctggttactc gtatccagac tgctgtgaaa tccgttgcca acagccagga    540
tatcgatctg gttgttgatg caaacgccgt tgcttacaac agcagcgatg taaaagacat    600
cactgccgac gtactgaaac aggttaaata agta                                634
```

```
<210> SEQ ID NO 18
<211> LENGTH: 161
<212> TYPE: PRT
<213> ORGANISM: E. Coli

<400> SEQUENCE: 18
```

```
Met Lys Lys Trp Leu Leu Ala Ala Gly Leu Gly Leu Ala Leu Ala Thr
1               5                   10                  15

Ser Ala Gln Ala Ala Asp Lys Ile Ala Ile Val Asn Met Gly Ser Leu
            20                  25                  30

Phe Gln Gln Val Ala Gln Lys Thr Gly Val Ser Asn Thr Leu Glu Asn
        35                  40                  45

Glu Phe Lys Gly Arg Ala Ser Glu Leu Gln Arg Met Glu Thr Asp Leu
    50                  55                  60

Gln Ala Lys Met Lys Lys Leu Gln Ser Met Lys Ala Gly Ser Asp Arg
65                  70                  75                  80

Thr Lys Leu Glu Lys Asp Val Met Ala Gln Arg Gln Thr Phe Ala Gln
                85                  90                  95

Lys Ala Gln Ala Phe Glu Gln Asp Arg Ala Arg Arg Ser Asn Glu Glu
            100                 105                 110

Arg Gly Lys Leu Val Thr Arg Ile Gln Thr Ala Val Lys Ser Val Ala
        115                 120                 125

Asn Ser Gln Asp Ile Asp Leu Val Val Asp Ala Asn Ala Val Ala Tyr
    130                 135                 140

Asn Ser Ser Asp Val Lys Asp Ile Thr Ala Asp Val Leu Lys Gln Val
145                 150                 155                 160

Lys
```

METHOD FOR OPTIMIZING ANTIBODY EXPRESSION

CROSS-REFERENCE TO RELATED APPLICATIONS

This application is a U.S. National Stage entry under 35 U.S.C § 371 of International Application No. PCT/US2019/030295, filed on May 1, 2019, which is incorporated by reference herein in its entirety and claims priority to and the benefit of U.S. Provisional Application Ser. No. 62/665,093 filed on May 1, 2018, the specification and contents of which is incorporated by reference herein in its entirety for all purposes.

SEQUENCE LISTING

The instant application contains a Sequence Listing which has been submitted in ASCII format via EFS-Web and is hereby incorporated by reference in its entirety. The ASCII copy, created on Apr. 30, 2019 is named_AMBX_0226_00 PCT_ST25.txt and is 15,184 bytes in size.

FIELD OF THE INVENTION

The present disclosure pertains to the field of molecular biology. The present invention disclosure relates to the design and engineering of vectors and plasmids. The invention also relates to novel production strains or cells incorporating non-naturally encoded amino acids and methods of producing recombinant proteins therefrom.

BACKGROUND OF THE INVENTION

Accumulation of intact, properly assembled, active antibody fragment in *Escherichia coli* (*E. coli*) periplasm requires multiple steps to occur correctly including: transcription, translation, suppression of a stop codon for non-natural amino acid incorporation, translocation across the inner membrane, cleavage of signal peptide, proper folding, correct cis or trans isomerization of proline residues, assembly of light chain with heavy chain, correct formation of intra- and inter-disulfide bonds, and retention in periplasm (no leakage across outer membrane into medium). Alternative pathways for polypeptides in the cytoplasm or periplasm include truncation, misfolding, aggregation, and proteolysis (Miot M. & Betton J. M., Microbial Cell Factories, 3, 4, 2004; Yoon, S. H, et al., Recent Patents in Biotech, 4, 23, 2010).

Many classes of helper proteins and/or factors in *E. coli* function to assist in generating protein in its properly folded and active state. These proteins include chaperones, foldases, isomerases etc., but are not limited to such. Chaperones bind to misfolded or unfolded proteins and facilitate proper folding. Other helper proteins and/or factors include proteins involve in disulfide bond reduction/oxidation or isomerization, peptidyl-prolyl isomerases that interconvert the cis/trans peptidyl-prolyl bond, and proteases that degrade misfolded or aggregated proteins. Overexpression of many of these proteins has been used to increase titer of heterologous proteins, including antibody fragments, in *E. coli* (Thomas et al., Applied Biochemistry and Biotechnology, 66, 197, 1997; Kolaj et. al., Microbial Cell Factories, 8, 2009; Merdanovic et. al., Annu, Rev. Microbiol. 65, 149, 2011).

In the industry, prokaryotic expression of an antibody or antibody fragment having a non-natural amino acid incorporated at a selected or specific site is difficult to achieve. This is particularly observed for antibody fragments in *E. coli*. To date, only a handful of biotech and pharmaceutical companies can successfully express wild-type antibody fragments in *Escherichia coli* at a high titer.

To overcome the challenges faced with expressing difficult-to-express (DTE) proteins, the present invention utilizes helper proteins and/or factors, including chaperones, in the design and engineering of vectors and plasmids therefrom to achieve optimization of titer of an antibody fragment into which a non-naturally encoded amino acid is incorporated.

SUMMARY OF THE INVENTION

The present invention provides novel engineered vectors, plasmids and production strains. In some embodiments, the invention novel expression plasmids and corresponding production strain for protein expression optimization and titer yield. In embodiment of the invention the engineered vectors and strains comprise a nucleic acid sequence encoding a protein of interest having a non-natural amino acid site specifically incorporated and a nucleic acid sequence encoding one or more component wherein the component is a helper protein or factor or a genetic element. In other embodiments, the invention disclosure provides methods and expression plasmids and production strains for optimizing protein expression in a prokaryote system, such as but not limited to *E. coli*.

In some embodiments the one or more component(s) is a eukaryotic or prokaryotic component. In some embodiments the one or more component is a helper protein or factor or a genetic element: The genetic element can be a gene or polynucleotide encoding a protein, or regulatory element.

In one embodiment the present invention provides a vector for optimizing protein expression comprising a nucleic acid sequence encoding a protein of interest having a non-naturally encoded amino acid site specifically incorporated, and a nucleic acid sequence encoding one or more components wherein the one or more components is selected from SEQ. ID. NOs.: 12, 15, or 17.

In other embodiments, the one or more components may be involved in protein folding, periplasmic chaperones, genetic elements including DNA coding sequence, Fab heavy chain (HC) carboxy-terminal extension and the plasmid partition locus, parB. In some embodiments one of these components may be included in an expression plasmid along with the protein of interest. In other embodiments, two or three or more of these components may be included in a plasmid along with the protein of interest. In some embodiments, all components may be included in a single expression plasmid having a native promoter or in a two plasmid system having an inducible promoter.

In other embodiments, the one or more components is a helper protein or factor or a genetic element. In other embodiments, the helper protein or factor is a chaperone. The chaperone is Skp or FkpA or Skp and FkpA. In one other embodiment the genetic element is partition B locus (parB).

In one embodiment the vector of present invention further comprises heavy chain C-terminal extension variant. In one other embodiment, the heavy chain C-terminal extension variant is an antibody heavy chain C-terminal extension variant. In other embodiments, the heavy chain C-terminal extension variant comprises one or more amino acids.

In other embodiments, parB is positioned in a forward transcriptional orientation between the Afe1 and Not1 sites of the nucleic acid sequence encoding the protein of interest.

In another embodiment parB is positioned in a forward transcriptional orientation at the Afe1 or Zra1 sites of the nucleic acid sequence encoding the protein of interest. In one other embodiment parB is positioned in a reverse transcriptional orientation at the Afe1 or Zra1 sites of the nucleic acid sequence encoding the protein of interest. In another embodiment the vector further comprises partition B locus (parB).

In one embodiment, the one or more protein capable of facilitating protein folding is FkpA, Skp, SurA, PPiA and PPiD. In other embodiments, the one or more protein capable of facilitating protein secretion or translocation, is SecY, SecE, SecG, SecYEG, SecA, SecB, FtsY and Lep. In one other embodiment, the one or more protein capable of facilitating disulfide bond formation is DsbA, DsbB, DsbD, DsbG. In some embodiments the chaperone may include Skp or FpkA. In other embodiments, parB may be cloned in the forward direction between the Afe1 and Not1 sites, at the Zra1 site, or at the Afe1 site. In other embodiments the plasmid contains a 271-base pair sequence deletion. In another embodiment, the plasmid contains parB in the forward orientation and Skp or FpkA chaperons cloned at Zra1 site. In other embodiments, the plasmid contains either parB or FkpA in an upstream or downstream position and parB in the forward orientation. In a further embodiment, the plasmid contains either FkpA in an upstream or downstream position and in the forward or reverse orientation. In one other embodiment the plasmid contains parB in an upstream position and FkpA in a downstream position. In another embodiment the plasmid contains parB in a downstream position and FkpA in an upstream position. In some embodiments, the heavy chain carboxy-terminal extension may comprise or consist of 1, 2, 3, 4, 5 or more amino acids. In some embodiments the heavy chain carboxy-terminal extension may comprise or consist of 5 or more amino acids with at least one mutation therein.

In other embodiments, the protein of interest is selected from a biotherapeutic, biologically active molecule, immunogen, antibody, antibody fragment or variants thereof. In other embodiments, the biotherapeutic is a vaccine. In one other embodiment, the protein of interest is a cytokine, chemokine, growth factor, growth factor receptor, interferon, interleukin, inflammatory molecule, oncogene product, peptide hormone, signal transduction molecule, or steroid hormone receptor. In other embodiments, the protein of interest is HER2, CD-70, PSMA, 5T4, EGFR, TROP2, CD3, IL-2, IL-3, IL-10, IL-12, IL-15, IL-21, GPC3, DLL3, ROR1, leptin, ghrelin, FGF-1, FGF-19, FGF-21, FGF-23, HGH, FcR, insulin, IGF1, TNFR1, TRAIL, EPO, and analogs, bispecifics or fragments thereof.

In one embodiment the antibody is a full length antibody or an antibody fragment. In other embodiments, the antibody is an IgG1, IgG2, IgG3 or IgG4 antibody. In other embodiments, the antibody fragment is Fab, Fab', F(ab')2, Fv fragments, single chain antibody fragments (scFv), disulfide stabilized scFv (dsFv)), diabody (Db), BiTE (bispecific T-cell Engager), DART (Dual Affinity Re-Targeting), or Tandem Diabody (TandAb). In some embodiments, the antibody fragment is Fab.

In embodiment of the invention the engineered plasmid and strains comprise a nucleic acid sequence encoding antibodies targeting proteins or polypeptides of interest including but not limited to HER2, CD-70, PSMA, 5T4, EGFR, TROP2, CD3, IL-2, IL-3, IL-10, IL-12, IL-15, IL-21, GPC3, DLL3, ROR1, leptin, ghrelin, FGF-1, FGF-19, FGF-21, FGF-23, HGH, FcR, insulin, IGF1, TNFR1, TRAIL, EPO, and analogs, bispecifics or fragments thereof having a non-natural amino acid site specifically incorporated and a nucleic acid sequence encoding one or more components wherein the one or more component is a helper protein or factor or a genetic element. In other embodiments of the invention the engineered plasmids comprise a nucleic acid sequence encoding an antibody specific for any target antigen including but not limited to HER2, CD-70, PSMA, 5T4, EGFR, TROP2, CD3, IL-2, IL-3, IL-10, IL-12, IL-15, IL-21, GPC3, DLL3, ROR1, leptin, ghrelin, FGF-1, FGF-19, FGF-21, FGF-23, HGH, FcR, insulin, IGF1, TNFR1, TRAIL, EPO, and analogs, bispecifics or fragments thereof wherein the fragment is a Fab, Fab', F(ab')2, Fv fragments, single chain antibody fragments (scFv), disulfide stabilized scFv (dsFv)), diabody (Db), BiTE (bispecific T-cell Engager), DART (Dual Affinity Re-Targeting), or Tandem Diabody (TandAb) and the like, having a non-natural amino acid site specifically incorporated and a nucleic acid sequence encoding one or more components wherein the one or more component is a helper protein or factor or a genetic element. In other embodiments of the nucleic acid sequence encodes a HER2, CD-70, PSMA, 5T4, EGFR, TROP2, CD3, IL-2, IL-3, IL-10, IL-12, IL-15, IL-21, GPC3, DLL3, ROR1, leptin, ghrelin, FGF-1, FGF-19, FGF-21, FGF-23, HGH, FcR, insulin, IGF1, TNFR1, TRAIL, EPO, and analogs, bispecific or antibody fragment but is not limited to such. In other embodiments the antibody fragment is a Fab, Fab', F(ab')2, Fv fragments, single chain antibody fragments (scFv), disulfide stabilized scFv (dsFv)), diabody (Db), BiTE (bispecific T-cell Engager), DART (Dual Affinity Re-Targeting), or Tandem Diabody (TandAb) but is not limited to such. In other embodiments, the antibody or fragment thereof is a pegylated Fab molecule. In other embodiments, the antibody fragment is anti-CD3 Fab.

In one embodiment the engineered production strain or cell is 2797, 2835, 2884, 2885, 2886, 2887, 2909, 2910, 2914, 2915, 2916, 2917, 2918, 2839, 2840, 2841, 3004, 3005, or 3006 as illustrated in the figures, tables and Examples herein. In another embodiment, the expression plasmid is plasmid p56, p96, p117, p118, p119, p120, p134, p135, p141, p142, p143, p144, p145, p94, p199, p200, or p201 as illustrated in the figures, tables and Examples herein.

In one embodiment the invention provides a recombinant cell comprising a nucleic acid sequence encoding a protein of interest having a non-naturally encoded amino acid site specifically incorporated, and a nucleic acid sequence encoding one or more components wherein the one or more components is selected from SEQ. ID. NOs.: 12, 15, or 17. In one embodiment, the recombinant cell is strain 2797, 2835, 2884, 2885, 2886, 2887, 2909, 2910, 2914, 2915, 2916, 2917, 2918, 2839, 2840, 2841, 3004, 3005 or 3006. In other embodiments, the recombinant cell comprises the chaperone Skp and partition B locus (parB). The cell is selected from strain 2910 or 2841. In other embodiments, the recombinant cell comprises the chaperone FkpA and partition B locus (parB). The cell is selected from strain 2909, 2840, 3004, 3005 or 3006. In other embodiments, the recombinant cell comprises a heavy chain C-terminal extension variant. The cell is selected from strain 2914, 2915, 2916, 2917, or 2918.

In one embodiment the invention provides an expression plasmid according to any of the claims wherein the plasmid is p56, p94, p96, p117, p118, p119, p120, p134, p135, p141, p142, p143, p144, p145, p199, p200 or p201.

In other embodiments, optimizing or increasing the expression titer of a protein, polypeptide, or antibody fragment of interest in a prokaryote system such as *E. coli* may include optimizing, or increasing the expression yield at least 0.2-fold, at least 0.5-fold, at least 1-fold, at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, at least 70-fold, at least 80-fold, at least 90 or more fold over the starting strain. In other embodiments, optimizing or increasing the expression titer of a protein, polypeptide, antibody fragment of interest in a prokaryote system such as E. coli may include optimizing, or increasing the expression yield at about or approximately 0.25 g/L, 0.5 g/L, 1.0 g/L, 1.5 g/L, 2.0 g/L, 2.5 g/L, 3.0 g/L, 3.5 g/L, 4.0 g/L, 4.5 g/L, 5.0 g/L or greater, 10 g/L or greater, 20 g/L or greater.

In one embodiment the invention provides a method of producing a recombinant protein of interest incorporating a non-naturally encoded amino acid, the method comprising expressing the protein in a bacterial cell and introducing a nucleic acid sequence encoding one or more components wherein the one or more components is selected from SEQ. ID. NOs.: 12, 15, or 17. In one other embodiment is provided a method for improving the yield of a protein having a non-natural amino acid site-specifically incorporated. In some embodiments, the invention provides method for optimizing or increasing recombinant protein expression of a difficult-to-express protein of interest wherein the protein incorporates a non-naturally encoded amino acid. In other embodiments, the chaperone gene position and orientation in relation to the gene of interest can optimize the recombinant protein yield.

In other embodiments the protein, polypeptide, antibody or gene of interest is a cytokine, a growth factor, a growth factor receptor, an interferon, an interleukin, an inflammatory molecule, an oncogene product, a peptide hormone, a signal transduction molecule, a steroid hormone receptor, a transcriptional activator, a transcriptional suppressor, erythropoietin (EPO), insulin, human growth hormone, epithelial Neutrophil Activating Peptide-78, GROα/MGSA, GROβ, GRO, MIP-1α, MIP-1&, MCP-1, hepatocyte growth factor, insulin-like growth factor, leukemia inhibitory factor, oncostatin M, PD-ECSF, PDGF, pleiotropin, SCF, c-kit ligand, VEGF, G-CSF, IL-1, IL-2, IL-8, IGF-I, IGF-II, FGF (fibroblast growth factor), TNF, TGF-α, TGF-β, EGF (epidermal growth factor), KGF (keratinocyte growth factor), SCF/c-Kit, CD40L/CD40, VLA-4/VCAM-1, ICAM-1/LFA-1, hyalurin/CD44, Mos, Ras, Raf, Met, p53, Tat, Fos, Myc, Jun, Myb, Rel, estrogen receptor, progesterone receptor, testosterone receptor, aldosterone receptor, LDL receptor, and corticosterone, an Alpha-1 antitrypsin, an Angiostatin, an Antihemolytic factor, an Apolipoprotein, an Apoprotein, an Atrial natriuretic factor, an Atrial natriuretic polypeptide, an Atrial peptide, a C-X-C chemokine, T39765, NAP-2, ENA-78, a Gro-a or Gro-c, an IP-10, a GCP-2, an NAP-4, an SDF-1, a PF4, a MIG, a Calcitonin, a c-kit ligand, a cytokine, a CC chemokine, a Monocyte chemoattractant protein-1, a Monocyte chemoattractant protein-2, a Monocyte chemoattractant protein-3, a Monocyte inflammatory protein-1 alpha, a Monocyte inflammatory protein-1 beta, RANTES, 1309, R83915, R91733, HCC1, T58847, D31065, T64262, a C-kit Ligand, a Collagen, a Colony stimulating factor (CSF), a Complement factor 5a, a Complement inhibitor, a Complement receptor 1, a cytokine, an epithelial Neutrophil Activating Peptide-78, an Epidermal Growth Factor (EGF), an epithelial Neutrophil Activating Peptide, an Erythropoietin (EPO), an Exfoliating toxin, a Factor IX, a Factor VII, a Factor VIII, a Factor X, a Fibroblast Growth Factor (FGF), a Fibrinogen, a Fibronec-tin, a G-CSF, a GM-CSF, a Glucocerebrosidase, a Gonadotropin, a growth factor, a growth factor receptor, a Hedgehog protein, a Hemoglobin, a Hepatocyte Growth Factor (HGF), a Hirudin, a Human serum albumin, an ICAM-1, an ICAM-1 receptor, an LFA-1, an LFA-1 receptor, an Insulin, an Insulin-like Growth Factor (IGF), an IGF-I, an IGF-II, an interferon, an IFN-α, an IFN-beta, an IFN-γ, an interleukin, an IL-1, an IL-2, an IL-3, an IL-4, an IL-5, an IL-6, an IL-7, an IL-8, an IL-9, an IL-10, an IL-11, an IL-12, a Keratinocyte Growth Factor (KGF), a Lactoferrin, a leukemia inhibitory factor, a Luciferase, a Neurturin, a Neutrophil inhibitory factor (NIF), an oncostatin M, an Osteogenic protein, an oncogene product, a Parathyroid hormone, a PD-ECSF, a PDGF, a peptide hormone, a Human Growth Hormone, a Pleiotropin, a Protein A, a Protein G, a Pyrogenic exotoxins A, B, or C, a Relaxin, a Renin, an SCF, a Soluble complement receptor I, a Soluble I-CAM 1, a Soluble interleukin receptors, a Soluble TNF receptor, a Somatomedin, a Somatostatin, a Somatotropin, a Streptokinase, a Superantigens, a Staphylococcal enterotoxins, an SEA, an SEB, an SEC1, an SEC2, an SEC3, an SED, an SEE, a steroid hormone receptor, a Superoxide dismutase, a toxic shock syndrome toxin, a thymosin alpha 1, a Tissue plasminogen activator, a tumor growth factor (TGF), a TGF-α, a TGF-β, a Tumor Necrosis Factor, a Tumor Necrosis Factor alpha, a Tumor necrosis factor beta, a Tumor necrosis factor receptor (TNFR), a VLA-4 protein, a VCAM-1 protein, a Vascular Endothelial Growth Factor (VEGF), a Urokinase, a Mos, a Ras, a Raf, a Met; a p53, a Tat, a Fos, a Myc, a Jun, a Myb, a Rel, an estrogen receptor, a progesterone receptor, a testosterone receptor, an aldosterone receptor, an LDL receptor, and a corticosterone and the like.

In other embodiments, the non-naturally amino acid is selected from the group consisting of: an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α di-substituted amino acid; a β-amino acid; and a cyclic amino acid other than praline.

In other embodiments, the invention provides an isolated cell or cell line. In some embodiments, the isolated cell or cell line is for producing a non-natural amino acid-containing protein or polypeptide. In one other embodiment, the invention provides an isolated cell or cell line wherein the yield of the non-natural amino acid containing protein is at least 0.25-fold or greater in the presence of one or more chaperones and parB locus. In other embodiments, the yield of the non-natural amino acid containing protein is at least 0.25-fold or greater in the presence of one or more chaperones and parB locus is positioned in a reverse transcriptional orientation at the AfeI site of the nucleic acid sequence encoding the protein of interest. In other embodiments. The isolated cell or cell line of optimizes plasmid retention in a production cell or cell line.

BRIEF DESCRIPTION OF THE DRAWINGS

The novel features of the invention are set forth with particularity in the appended claims. A better understanding of the features and advantages of the present invention disclosure will be obtained by reference to the following detailed description that sets forth illustrative embodiments, in which the principles of the invention are utilized, and the accompanying drawings provided.

FIG. 13A shows recoverable titer by Capto S column of heavy chain (HC) variants. FIG. 13B shows purity analysis of Capto S column pool of heavy chain (HC) extension variants.

DETAILED DESCRIPTION OF THE INVENTION

Figure 1:
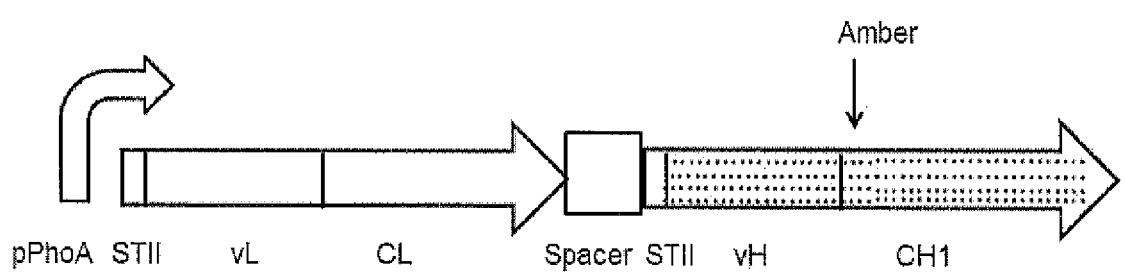
FIG. 1. Schematic of anti-CD3 Fab-HK129pAcF expression cassette with unnatural amino acid pAcF incorporation site shown within the heavy chain constant domain (CH1) region.

Before describing the present invention in detail, it is to be understood that this invention is not limited to particular methodologies, or compositions, or biological systems, which can, of course, vary. It is also to be understood that the terminology used herein is for the purpose of describing particular embodiments only and is not intended to be limiting. As used in this specification and the appended claims, the singular forms "a", "an" and "the" include plural referents unless the content clearly dictates otherwise. Thus, for example, reference to "a cell" includes a combination of two or more cells and the like.

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Unless otherwise defined herein or below in the remainder of the specification, all technical and scientific terms used herein have the same meaning as commonly understood by those of ordinary skill in the art to which the invention belongs.

Definitions

The term "amino acid" refers to naturally occurring and non-natural or unnatural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to compounds that have the same basic chemical structure as a naturally occurring amino acid, by way of example only, an α-carbon that is bound to a hydrogen, a carboxyl group, an amino group, and a functional R group. Such analogs may have modified R groups (by way of example, norleucine) or may have modified peptide backbones while still retaining the same basic chemical structure as a naturally occurring amino acid. Non-limiting examples of amino acid analogs include homoserine, norleucine, methionine sulfoxide, methionine methyl sulfonium. Amino acids may be referred to herein by either their name, their commonly known three letter symbols or by the one-letter symbols recommended by the IUPAC-IUB Biochemical Nomenclature Commission. Additionally, nucleotides, may be referred to by their commonly accepted single-letter codes.

The term "antibody" herein refers to a protein consisting of one or more polypeptides substantially encoded by all or part of the antibody genes. The immunoglobulin genes include, but are not limited to, the kappa, lambda, alpha, gamma (IgG1, IgG2, IgG3, and IgG4), delta, epsilon and mu constant region genes, as well as the myriad immunoglobulin variable region genes. Antibody herein is also meant to include full-length antibodies and antibody fragments, and include antibodies that exist naturally in any organism, antibody variants, engineered antibodies and antibody fragments. Antibody herein is also meant to include intact antibody, monoclonal or polyclonal antibodies. Antibody herein also encompasses, multispecific antibodies and/or bispecific antibodies. Antibodies of the present invention include human antibodies. Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

The term "antibody fragment" herein refers to any form of an antibody other than the full-length form. Antibody fragments herein include antibodies that are smaller components that exist within full-length antibodies, and antibodies that have been engineered, such as antibody variants. Antibody fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDRs, variable regions, framework regions, constant regions, heavy chains, light chains, and variable regions, and alternative scaffold non-antibody molecules, bispecific antibodies, and the like (Maynard & Georgiou, Annu. Rev. Biomed. Eng. 2:339-76, 2000; Hudson, Curr. Opin. Biotechnol. 9:395-402, 1998). Another functional substructure is a single chain Fv (scFv), comprised of the variable regions of the immunoglobulin heavy and light chain, covalently connected by a peptide linker (Hu et al., Cancer Research, 56, 3055-3061, 1996). These small (Mr 25,000) proteins generally retain specificity and affinity for antigen in a single polypeptide and can provide a convenient building block for larger, antigen-specific molecules. Unless specifically noted otherwise, statements and claims that use the term "antibody" or "antibodies" specifically includes "antibody fragment" and "antibody fragments." As used herein, the term "antibody fragment," when used in the context of antibody, refers to a portion of the antibody that is from about 10% to about 99% the length of the complete antibody. For example, a fragment of an antibody can be at least about 10%, 11%, 12%, 13%, 14%, 15%, 16%, 17%, 18%, 19%, 20%, 21%, 22%, 23%, 24%, or 25% of the length of the complete antibody. A fragment of an antibody can also be at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the length of the complete antibody. In some embodiments, the antibody fragment is a diabody (Db), BiTE (bispecific T-cell Engager), DART (Dual Affinity Re-Targeting), or Tandem Diabody (TandAb).

In some embodiments the disclosure concerns amino acids that have been biosynthetically incorporated in the antibody. The term "biosynthetically," as used herein, refers to any method utilizing a translation system (cellular or non-cellular), including use of at least one of the following components: a polynucleotide, a codon, a tRNA, and a ribosome. By way of example, non-natural amino acids may be "biosynthetically incorporated" into non-natural amino acid polypeptides using the methods and techniques described herein and as is well known in the art. See for example, WO2010/011735 and WO2005/074650.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, vaccines, immunogens, hard drugs, soft drugs, carbohydrates, inorganic atoms or molecules, dyes, lipids, nucleosides, radionuclides, oligonucleotides, toxoids, biologically active molecules, prokaryotic and eukaryotic cells, viruses, polysaccharides, nucleic acids and portions thereof obtained or derived from viruses, bacteria, insects, animals or any other cell or cell type, liposomes, microparticles and micelles. Classes of biologically active agents that are suitable for use with the invention include, but are not limited to, drugs, prodrugs, radionuclides, imaging agents, polymers, antibiotics, fungicides, bile-acid resins, niacin, and/or statins, anti-inflammatory agents, anti-tumor agents, cardiovascular agents, anti-anxiety agents, hormones, growth factors, steroidal agents, checkpoint protein inhibitors, signaling pathway inhibitors, microbially derived biologically active molecules, and the like. Biologically active agents also include amide compounds such as those described in U.S. Patent Application Publication Number 20080221112.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used herein with respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N→2,3-(Dioleyoxy)-propyl-N,N,N-trimethyl-ammonium, mild ionic detergents (e.g. sodium cholate or sodium deoxycholate) or zwitterionic detergents including, but not limited to, sulfobetaines (Zwittergent), 3-(3-chlo-lamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially C2-C4 alkanols such as ethanol or isopropanol), or lower alkandiols (especially C2-C4 alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. The term "conservatively modified variants" applies to both natural and non-natural amino acid and natural and non-natural nucleic acid sequences, and combinations thereof. With respect to particular nucleic acid sequences, "conservatively modified variants" refers to those natural and non-natural nucleic acids which encode identical or essentially identical natural and non-natural amino acid sequences, or where the natural and non-natural nucleic acid does not encode a natural and non-natural amino acid sequence, to essentially identical sequences. By way of example, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Thus, by way of example every natural or non-natural nucleic acid sequence herein which encodes a natural or non-natural polypeptide also describes every possible silent variation of the natural or non-natural nucleic acid. One of ordinary skill in the art will recognize that each codon in a natural or non-natural nucleic acid (except AUG, which is ordinarily the only codon for methionine, and UGG, which is ordinarily the only codon for tryptophan) can be modified to yield a functionally identical molecule. Accordingly, each silent variation of a natural and non-natural nucleic acid which encodes a natural and non-natural polypeptide is implicit in each described sequence. As to amino acid sequences, individual substitutions, deletions or additions to a nucleic acid, peptide, polypeptide, or protein sequence which alters, adds or deletes a single natural and non-natural amino acid or a small percentage of natural and non-natural amino acids in the encoded sequence is a "conservatively modified variant" where the alteration results in the deletion of an amino acid, addition of an amino acid, or substitution of a natural and non-natural amino acid with a chemically similar amino acid. Conservative substitution tables providing functionally similar natural amino acids are well known in the art. Conservative substitution tables providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins: Structures and Molecular Properties, W H Freeman & Co. 2nd edition, 1993). Such conservatively modified variants are in addition to and do not exclude polymorphic variants, interspecies homologs, and alleles of the compositions described herein.

The term "identical," as used herein, refers to two or more sequences, (nucleic acids or polypeptide), or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75 to about 100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75 to about 100 nucleic acids in length, over a region that is about 50 nucleic acids in length, or, where not specified, across the entire sequence of a polynucleotide sequence.

The term "isolated," as used herein, refers to separating and removing a component of interest from components not of interest. The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. Purity and homogeneity may be determined using analytical chemistry techniques including, but not limited to, polyacrylamide gel electrophoresis or high-performance liquid chromatography. In addition, when a component of interest is isolated and is the predominant species present in a preparation, the component is described herein as substantially purified. The term "purified," as used herein, may refer to a component of interest which is at least 85% pure, at least 90% pure, at least 95% pure, at least 99% or greater pure. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

The term "modified," as used herein refers to any changes made to a given polypeptide, such as changes to the length of the polypeptide, the amino acid sequence, chemical structure, co-translational modification, or post-translational modification of a polypeptide. In some instances the polypeptides are optionally modified, that is, the polypeptides can be modified or unmodified.

A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

The term "nucleic acid," as used herein, refers to deoxyribonucleotides, deoxyribonucleosides, ribonucleosides or ribonucleotides and polymers thereof in either single- or double-stranded form. By way of example only, such nucleic acids and nucleic acid polymers include, but are not limited to, (i) analogues of natural nucleotides which have similar binding properties as a reference nucleic acid and are metabolized in a manner similar to naturally occurring nucleotides; (ii) oligonucleotide analogs including, but are not limited to, PNA (peptidonucleic acid), analogs of DNA used in antisense technology (phosphorothioates, phosphoroamidates, and the like); (iii) conservatively modified variants thereof (including but not limited to, degenerate codon substitutions) and complementary sequences and sequence explicitly indicated. By way of example, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. Additionally, such "polypeptides," "peptides" and "proteins" include amino acid chains of any length, including full length proteins, wherein the amino acid residues are linked by covalent peptide bonds. In embodiments of the present invention the protein of interest is a cytokine, a growth factor, a growth factor receptor, an interferon, an interleukin, an inflammatory molecule, an oncogene product, a peptide hormone, a signal transduction molecule, a steroid hormone receptor, a transcriptional activator, a transcriptional suppressor, erythropoietin (EPO), insulin, human growth hormone, epithelial Neutrophil Activating Peptide-78, GROα/MGSA, GROβ, GRO, MIP-1α, MIP-1&, MCP-1, hepatocyte growth factor, insulin-like growth factor, leukemia inhibitory factor, oncostatin M, PD-ECSF, PDGF, pleiotropin, SCF, c-kit ligand, VEGF, G-CSF, IL-1, IL-2, IL-8, IGF-I, IGF-II, FGF (fibroblast growth factor), TNF, TGF-α, TGF-β, EGF (epidermal growth factor), KGF (keratinocyte growth factor), SCF/c-Kit, CD40L/CD40, VLA-4/VCAM-1, ICAM-1/LFA-1, hyalurin/CD44, Mos, Ras, Raf, Met, p53, Tat, Fos, Myc, Jun, Myb, Rel, estrogen receptor, progesterone receptor, testosterone receptor, aldosterone receptor, LDL receptor, and corticosterone, an Alpha-1 antitrypsin, an Angiostatin, an Antihemolytic factor, an Apolipoprotein, an Apoprotein, an Atrial natriuretic factor, an Atrial natriuretic polypeptide, an Atrial peptide, a C-X-C chemokine, T39765, NAP-2, ENA-78, a Gro-a or Gro-c, an IP-10, a GCP-2, an NAP-4, an SDF-1, a PF4, a MIG, a Calcitonin, a c-kit ligand, a cytokine, a CC chemokine, a Monocyte chemoattractant protein-1, a Monocyte chemoattractant protein-2, a Monocyte chemoattractant protein-3, a Monocyte inflammatory protein-1 alpha, a Monocyte inflammatory protein-1 beta, RANTES, 1309, R83915, R91733, HCC1, T58847, D31065, T64262, a C-kit Ligand, a Collagen, a Colony stimulating factor (CSF), a Complement factor 5a, a Complement inhibitor, a Complement receptor 1, a cytokine, an epithelial Neutrophil Activating Peptide-78, an Epidermal Growth Factor (EGF), an epithelial Neutrophil Activating Peptide, an Erythropoietin (EPO), an Exfoliating toxin, a Factor IX, a Factor VII, a Factor VIII, a Factor X, a Fibroblast Growth Factor (FGF), a Fibrinogen, a Fibronectin, a G-CSF, a GM-CSF, a Glucocerebrosidase, a Gonadotropin, a growth factor, a growth factor receptor, a Hedgehog protein, a Hemoglobin, a Hepatocyte Growth Factor (HGF), a Hirudin, a Human serum albumin, an ICAM-1, an ICAM-1 receptor, an LFA-1, an LFA-1 receptor, an Insulin, an Insulin-like Growth Factor (IGF), an IGF-I, an IGF-II, an interferon, an IFN-α, an IFN-beta, an IFN-γ, an interleukin, an IL-1, an IL-2, an IL-3, an IL-4, an IL-5, an IL-6, an IL-7, an IL-8, an IL-9, an IL-10, an IL-11, an IL-12, a Keratinocyte Growth Factor (KGF), a Lactoferrin, a leukemia inhibitory factor, a Luciferase, a Neurturin, a Neutrophil inhibitory factor (NIF), an oncostatin M, an Osteogenic protein, an oncogene product, a Parathyroid hormone, a PD-ECSF, a PDGF, a peptide hormone, a Human Growth Hormone, a Pleiotropin, a Protein A, a Protein G, a Pyrogenic exotoxins A, B, or C, a Relaxin, a Renin, an SCF, a Soluble complement receptor I, a Soluble I-CAM 1, a Soluble interleukin receptors, a Soluble TNF receptor, a Somatomedin, a Somatostatin, a Somatotropin, a Streptokinase, a Superantigens, a Staphylococcal enterotoxins, an SEA, an SEB, an SEC1, an SEC2, an SEC3, an SED, an SEE, a steroid hormone receptor, a Superoxide dismutase, a toxic shock syndrome toxin, a thymosin alpha 1, a Tissue plasminogen activator, a tumor growth factor (TGF), a TGF-α, a TGF-β, a Tumor Necrosis Factor, a Tumor Necrosis Factor alpha, a Tumor necrosis factor beta, a Tumor necrosis factor receptor (TNFR), a VLA-4 protein, a VCAM-1 protein, a Vascular Endothelial Growth Factor (VEGF), a Urokinase, a Mos, a Ras, a Raf, a Met; a p53, a Tat, a Fos, a Myc, a Jun, a Myb, a Rel, an estrogen receptor, a progesterone receptor, a testosterone receptor, an aldosterone receptor, an LDL receptor, and a corticosterone and the like.

The term "post-translationally modified" refers to any modification of a natural or non-natural amino acid which occurs after such an amino acid has been translationally incorporated into a polypeptide chain. Such modifications include, but are not limited to, co-translational in vivo modifications, co-translational in vitro modifications (such as in a cell-free translation system), post-translational in vivo modifications, and post-translational in vitro modifications.

The term "recombinant host cell," also referred to as "host cell," refers to a cell which includes an exogenous polynucleotide, wherein the methods used to insert the exogenous polynucleotide into a cell include, but are not limited to, direct uptake, transduction, f-mating, or other methods known in the art to create recombinant host cells. By way of example only, such exogenous polynucleotide may be a nonintegrated vector, including but not limited to a plasmid, or may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the protein of interest has been secreted, including medium either before or after a proliferation step. The term also may encompass buffers or reagents that contain host cell lysates, such as in the case where the protein of interest is produced intracellularly and the host cells are lysed or disrupted to release such.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater. By way of example only, a natural amino acid polypeptide or a non-natural amino acid polypeptide may be purified from a native cell, or host cell in the case of recombinantly produced natural amino acid polypeptides or non-natural amino acid polypeptides. By way of example a preparation of a natural amino acid polypeptide or a non-natural amino acid polypeptide may be "substantially purified" when the preparation contains less than about 30%, less than about 25%, less than about 20%, less than about 15%, less than about 10%, less than about 5%, less than about 4%, less than about 3%, less than about 2%, or less than about 1% (by dry weight) of contaminating material. By way of example when a natural amino acid polypeptide or a non-natural amino acid polypeptide is recombinantly produced by host cells, the natural amino acid polypeptide or non-natural amino acid polypeptide may be present at about 30%, about 25%, about 20%, about 15%, about 10%, about 5%, about 4%, about 3%, about 2%, or about 1% or less of the dry weight of the cells. By way of example when a natural amino acid polypeptide or a non-natural amino acid polypeptide is recombinantly produced by host cells, the natural amino acid polypeptide or non-natural amino acid polypeptide may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. By way of example, "substantially purified" natural amino acid polypeptides or non-natural amino acid polypeptides may have a purity level of about 30%, about 35%, about 40%, about 45%, about 50%, about 55%, about 60%, about 65%, about 70%, about 75%, about 80%, about 85%, about 90%, about 95%, about 99% or greater as determined by appropriate methods, including, but not limited to, SDS/PAGE analysis, RP-HPLC, SEC, and capillary electrophoresis.

In the present invention, the protein, peptide, polypeptide of interest to be expressed may be any protein, peptide, polypeptide that is expressed in an unstabilized form and/or insolubilized form, or a solubilized form in *E. coli* In some embodiments, a insoluble protein can be any protein, peptide, polypeptide in *E. coli* located in the cytoplasm. In other aspects of the invention, a soluble protein can be any protein, peptide, polypeptide in *E. Coli* located in the periplasm or cytoplasm or extracellular media. In some embodiments, such protein, peptide, polypeptide include a therapeutic, prophylactic or diagnostic protein, peptide, polypeptide. In other embodiments, such protein, peptide, polypeptide include interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitors, stem cell growth factors, tumor necrosis factors, growth hormones, proinsulin, insulin-like growth factors, fibroblast growth factors, platelet-derived growth factors, transforming growth factors, hepatocyte growth factors, bone morphogenetic factors, nerve growth factors, ciliary neurotrophic factors, brain-derived neurotrophic factors, glia cell line-derived neurotrophic factors, neurotrophine, prourokinase, tissue plasminogen activators, blood coagulation factors, protein C, glucocerebrosidase, superoxide dismutase, renin, lysozyme, P450, prochymosin, trypsin inhibitors, elastase inhibitors, lipocortin, reptin, immunoglobulins, single-chain antibodies, complement components, serum albumin, cedar pollen allergens, hypoxia-induced stress proteins, protein kinases, proto-oncogene products, transcription factors and virus-constituent proteins, but is not limited to such.

The term "derived from" refers to a component that is isolated from an organism or isolated and modified, or generated, e.g., chemically synthesized, using information of the component from the organism.

The term "translation system" refers to the components necessary to incorporate a naturally occurring amino acid into a growing polypeptide chain (protein). For example, components can include ribosomes, tRNAs, synthetases, mRNA and the like. The components of the present invention can be added to a translation system, in vivo or in vitro.

The term "prokaryote" refers to non-eukaryotic organisms belonging to the Eubacteria (including but not limited to, *Escherichia coli, Thermus thermophiles, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The present invention provides an "operon" encoding the Fab. The term "operon" used in the present invention is defined as a group of genes, each of which encodes the above-described Fab heavy and light chains, forming a transcription unit under the control of a single promoter, which includes a natural or artificial operon. In some embodiments of the present invention, the operon is a bi-cistronic operon is driven by the *E. coli* alkaline phosphatase (phoA) promoter.

As used herein, the term "promoter" refers to a nucleic acid sequence that regulates expression of a nucleic acid, operably linked thereto. Such promoters are known to be cis-acting sequence elements required for transcription as they serve to bind DNA dependent RNA polymerase, which transcribes sequences present downstream thereof. For regulation of the expression level of the protein (or gene) of interest of the present invention, it is preferable that the promoter controlling the transcription be an inducible promoter. Examples of the inducible promoter include, for instance, lac, tac, trc, trp, araB, Pzt-1, lambda $P_L$, and the like. The lac, tac and trc promoters can be induced by using isopropyl-1-thio-beta-D-galactopyranoside (IPTG); the trp, araB and Pzt-1 promoters can be induced by using 3-indoleacrylic acid (IAA), L-arabinose and tetracycline, respectively; and the epsilon $P_L$ promoter can be induced at a high temperature (42° C.). Also usable is a T7 promoter, which is specifically and strongly transcribed by a T7 RNA polymerase. In the transcription by T7 RNA polymerase, induction of the above T7 RNA polymerase by using IPTG is made possible using an *E. coli* strain harboring a lysogenized lambda phage carrying the T7 RNA polymerase gene located downstream of the lac promoter. In some embodiments the inducible promoter is the inducible tetracycline promoter (pTc). In some embodiments of the present invention, the inducible promoter used for expression of genetic elements such as chaperones, may be the same or different from the promoter used to express the protein of interest. In some embodiments it may be advantageous to independently control the expression of the genetic elements, such as chaperones, and that of the desired protein in optimizing the level and timing of expression of the chaperones without lowering the expression level of the desired protein.

In other embodiments, the term "promoter" refers to a region of DNA that generally is located upstream (towards the 5' region of a gene) that is needed for transcription. Promoters permit the proper activation or repression of the gene which they control. A promoter contains specific sequences that are recognized by transcription factors. These factors bind to the promoter DNA sequences and result in the recruitment of RNA polymerase, the enzyme that synthesizes the RNA from the coding region of the gene. In prokaryotes, the promoter is recognized by RNA polymerase and an associated sigma factor, which in turn are brought to the promoter DNA by an activator protein binding to its own DNA sequence nearby. In eukaryotes, the process is more complicated. For instance, at least seven different factors are necessary for the transcription of an RNA polymerase II promoter. Promoters represent elements that can work in concert with other regulatory regions (enhancers, silencers, boundary elements/insulators) to direct the level of transcription of a given gene. The promoters that are useful in carrying out the methods described herein include RNA polymerase III (also called Pol III) promoters, which transcribe DNA to synthesize ribosomal 5S rRNA, tRNA, and other small RNAs. Pol III is unusual (compared to Pol II) in that it requires no control sequences upstream of the gene. Instead, it can rely on internal control sequences. The RNA polymerase III promoters are more varied in structure than the uniform RNA polymerase I promoters, and yet not as diverse as the RNA polymerase II promoters. They have been divided into three main types (types 1-3), two of which are gene-internal and generally TATA-less, and one of which is gene-external and contains a TATA box.

As used herein, the term "encode" is an open-ended term such that a nucleic acid encoding a particular amino acid sequence can consist of codons specifying a polypeptide, or can also comprise additional sequences that are translatable, or whose presence is useful for the control of transcription, translation, or replication, or to facilitate manipulation of some host nucleic acid construct. As used herein, the term is construed broadly, and can have a variety of applications. In some instances, the term "encode" describes the process of semi-conservative DNA replication, where one strand of a double-stranded DNA molecule is used as a template to encode a newly synthesized complementary sister strand by a DNA-dependent DNA polymerase. When used to describe the process of translation, the teen "encode" also extends to the triplet codon that encodes an amino acid. In some instances, an RNA molecule can encode a DNA molecule, for instance, by the process of reverse transcription incorporating an RNA-dependent DNA polymerase. In another aspect, a DNA molecule can encode a peptide, where it is understood that "encode" as used in that case incorporates both the processes of transcription and translation. In another aspect, the term "encode" refers to any process whereby the information in one molecule is used to direct the production of a second molecule that has a different chemical nature from the first molecule.

As used herein, the term "gene expression" refers to the process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a cell, tissue or subject to an agent that increases or decreases gene expression. Expression of a gene also can be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression can be measured at the RNA level or the protein level and by any method known in the art, including, without limitation, Northern blot, RT-PCR, Western blot, or in vitro, in situ, or in vivo protein activity assay(s).

As used herein, the term "isolated" refers to a biological component (such as a nucleic acid molecule, peptide, or cell) has been purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression host cell for a recombinant peptide or nucleic acid molecule).

As used herein, the term "nucleic acid", "nucleic acid molecule", polynucleotide" refers to a polymeric form of nucleotides, which can include both sense and anti-sense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages. Nucleic acid molecules can be modified chemically or biochemically or can contain non-natural or derivatized nucleotide bases, as will be readily appreciated by those of skill in the art, Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, peptides), intercalators (for example, acridine, psoralen, etc.), chelators, alkylators, and modified linkages (for example, alpha anomeric nucleic acids, etc.). The term "nucleic acid molecule" also includes any topological conformation, including single-stranded, double-stranded, partially duplexed, triplexed, hairpinned, circular and padlocked conformations.

As used herein, the term "prokaryote" or "prokaryotic" refers to an organisms belonging to the Kingdom Monera (also termed Procarya). Prokaryotic organisms are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and *Mycoplasma* are sometimes given separate classifications under the Kingdom Monera.

As used herein, the term "transduction" refers to the process by which genetic material, for instance, DNA or other nucleic acid molecule, is inserted into a cell. Common transduction techniques include the use of viral vectors (including bacteriophages), electroporation, and chemical reagents that increase cell permeability. Transfection and transformation are other terms for transduction, although these sometimes imply expression of the genetic material as well.

The terms "transformation", "transformed" or "introducing a nucleic acid into a host cell" denote any process wherein an extracellular nucleic acid (exogeneous or heterologous DNA) like a vector, with or without accompanying material, enters a cell (e.g., host cell). The transforming DNA may or may not be integrated (covalently linked) into the genome of the cell. In prokaryote cells for example, the transforming DNA may be maintained on an episomal element such as a vector or plasmid. The term "cell transformed" or "transformed cell" means the cell or its progeny into which the extracellular nucleic acid has been introduced and thus harbours the extracellular nucleic acid. The nucleic acid might be introduced into the cell so that the nucleic acid is replicable either as a chromosomal integrant or as an extra chromosomal element. Transformation of appropriate host cells with e.g. an expression vector can be accomplished by well-known methods such as microinjection, electroporation, particle bombardment or by chemical methods such as Calcium phosphate-mediated transformation, described e.g. in Maniatis et al., Molecular Cloning, A laboratory Manual, Cold Spring Harbor Laboratory, 1982, or in Ausubel et al., Current protocols in molecular biology, John Wiley and Sons, 1994.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule". The term "recombinant protein" or "recombinant polypeptide" as used herein refers to a protein molecule which is expressed from a recombinant DNA molecule.

The term vector or construct as used herein refers to a nucleic acid molecule capable of transporting a non-vector nucleic acid sequence which has been introduced into the vector. One type of vector is a "plasmid," which refers to a circular double-stranded DNA into which non-plasmid DNA segments can be ligated. Other vectors include cosmids, bacterial artificial chromosomes (BAC) and yeast artificial chromosomes (YAC). Another type of vector is a viral vector, wherein additional DNA segments can be ligated into all or part of the viral genome. Certain vectors are capable of autonomous replication in a host cell into which they are introduced (for example, vectors having a bacterial origin of replication replicate in bacteria hosts). Other vectors can be integrated into the genome of a host cell upon introduction into the host cell and are replicated along with the host genome. Some vectors contain expression control sequences (such as promoters) and are capable of directing the transcription of an expressible nucleic acid sequence that has been introduced into the vector, such vectors are referred to as "expression vectors." A vector can also include one or more selectable marker genes and/or genetic elements known in the art.

The term "plasmid" as used herein refers to a DNA molecule separate from chromosomal DNA and capable of autonomous replication. It is typically circular and double-stranded, and can naturally occur in bacteria, and sometimes in eukaryotic organisms (for instance, the 2-micrometre-ring in *Saccharomyces cerevisiae*). The size of plasmids can vary from about 1 to over 400 kilobase pairs. Plasmids often contain genes or gene cassettes that confer a selective advantage to the bacterium (or other cell) harboring them, such as the ability to make the bacterium (or other cell) antibiotic resistant. Plasmids contain at least one DNA sequence that serves as an origin of replication, which enables the plasmid DNA to be duplicated independently from the chromosomal DNA. The chromosomes of most bacteria are circular, but linear plasmids are also known. Plasmids used in genetic engineering are referred to as vectors. They can be used to transfer genes from one organism to another, and typically contain a genetic marker conferring a phenotype that can be selected for or against. Most also contain a polylinker or multiple cloning site, which is a short region containing several commonly used restriction sites allowing the easy insertion of DNA fragments at this location. The plasmid of the present invention may further contain a selection marker gene in order to facilitate selection upon transformation. Examples of such selection marker genes include ampicillin resistance genes, kanamycin resistance genes, and chloramphenicol resistance genes. It is desired that the plasmid selection marker gene used be different from the selection marker gene, if any, contained in the chromosome of the strain. A plasmid as defined above, may be introduced into a host through standard techniques. With regard to transformation of prokaryotic host cells, see, for example, Cohen et al., Proc. Natl. Acad. Sci. USA 69, 2110, 1972 and Sambrook et al., Molecular Cloning, A Laboratory Manual, 3.sup.rd Ed. Cold Spring Harbor Laboratory, Cold Spring Harbor, N.Y., 2001.

As used herein, the term "expression cassette" refers to a polynucleotide sequence encoding a polypeptide, operably linked to a promoter and other transcription and translation control elements, including but not limited to enhancers, termination codons, internal ribosome entry sites, or polyadenylation sites. The cassette can also include sequences that facilitate moving it from one host molecule to another.

The term "expression construct" as used herein refers to an expression module or expression cassette made up of a recombinant or synthetic DNA molecule containing a desired coding sequence and appropriate nucleic acid sequences necessary for the expression of the operably linked coding sequence in a particular host organism. Nucleic acid sequences necessary for expression in prokaryotes usually include a promoter and a ribosome binding site, often along with other sequences. Typically, an expression vector includes a transcriptional unit comprising a particular nucleic acid sequence to be transcribed operably linked to a promoter. A vector in a host can be e.g. an autonomously or self-replicating plasmid, a cosmid, a phage, a virus or a retrovirus.

The terms "host", "host cell" and "recombinant host cell" are used interchangeably herein to indicate a prokaryotic cell into which one or more vectors or isolated and purified nucleic acid sequences of the invention have been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Genetic Elements or Components

As used herein, "genetic elements" or "genetic element" may include any molecules that may facilitate, enhance, potentiate or synergize with a helper protein or factor to promote protein expression. Genetic elements may facilitate transcription of one or more genes associated with, or involved in, protein expression. Such elements may be from a non-eukaryotic or eukaryotic source.

The present invention utilizes one or more genetic elements involved in protein expression, including difficult-to-express (DTE) proteins, protein folding, and plasmid retention and stabilization in a prokaryotic system. Such genetic elements include, but are not limited to, DNA coding sequence, and helper proteins and/or factors including chaperones, foldases and isomerases. In some embodiments of the invention, such genetic elements include periplasmic chaperones, heavy chain (HC) carboxy-terminal extension and the presence of plasmid partition locus, parB. Many classes of helper proteins and/or factors in *E. coli* assist in generating properly folded and active protein(s). Chaperones for example, bind to misfolded or unfolded proteins and facilitate proper folding. Other helper proteins play a role in disulfide bond reduction/oxidation or isomerization. Peptidyl-prolyl isomerases are involved in cis/trans peptidyl-prolyl bond interconversion, and proteases function to degrade misfolded or aggregated proteins.

It has been demonstrated in the art that overexpression of molecular chaperones of various classes increase the titer of heterologous proteins, including antibody fragments, in *E. coli* (Thomas et al., Applied Biochemistry and Biotechnology 66, 197, 1997; Kolaj et. al., Microbial Cell Factories, 2009; Merdanovic et. al., Annu. Rev. Microbiol. 65, 149, 2011). It is also known to those of skill in the art that antibody heavy chain (HC) polypeptide is difficult to fold and peptidyl prolyl isomerization has been proposed as a rate-limiting step for HC folding (Feige et al., Mol. Cell 34, 569, 2009). Further, prokaryotic expression of an antibody or antibody fragment having a non-natural amino acid incorporated at a selected site has been difficult to achieve.

The present invention utilizes helper proteins and/or factors or genetic elements in the design and engineering of vectors and plasmids therefrom to achieve increase in titer of proteins incorporating non-natural amino acids.

It is well known in the art that the periplasmic localization of several helper proteins and/or factors including protein folding factors and chaperones, catalyze the proper assembly and folding of functional antibody fragments. For example, chaperones promote the proper isomerisation and cellular targeting by transiently interacting with folding intermediates; and foldases accelerate rate-limiting steps along the folding pathway. It is also well known in the art that *Escherichia coli* is one of the most widely used hosts for the production of recombinant proteins. *E. coli* serves ideally as a host for production of heterologous proteins at low costs and high yields, because it can easily be grown to high densities and the studies on the host-vector systems have been most advanced and many high-expression vectors have been developed. *E. coli* host-vector systems are, therefore, most widely utilized as expression systems for heterologous genes.

The periplasm of *E. coli* provides a more oxidizing environment than the cytosol, which promotes disulfide bond formation, and the periplasmic space also contains fewer host proteins as compared to the cytoplasm, thus facilitating subsequent purification processes. However, there are often problems in recovering substantial yields of correctly folded proteins. For example, high expression of proteins, such as antibody fragments, increases the demand for protein folding promoting an uncharacterized metabolic burden on the cells leading to protein misfolding and aggregation. The periplasmic localization of several protein folding factors and chaperones catalyze the proper assembly and folding of functional proteins such as antibody fragments. One approach to solve the problem of low to poor protein yield is to have recombinant proteins secreted into the periplasmic space or culture medium. Therefore, to increase, improve and/or optimize protein yield periplasmic protein folding factors in *E. coli*. may be by utilized.

Another approach to improve the low to poor protein yield is to utilized helper proteins and/or factors including protein folding factors, such as chaperones, involved in restoring the solubility and functionality of recombinant protein products, and affecting cellular metabolism during periplasmic antibody fragment expression. Chaperones of the present invention may be any protein involved in protein folding including, but not limited to chaperones derived from *E. coli*. Examples of such chaperones include, for example, DnaK, DnaJ, GrpE, GroEL, GroES, HscA/Hsc66, ClpA, ClpB, ClpS, ClpX, HtpG, HdeA, HdeB, HtpG, HslO, HscC osmY, SecB, Spy, Tig and the like. Other chaperones include the periplasmic chaperones Skp, FkpA, SurA, PPiA, PPiD but are not limited to such. In some embodiments of the invention one or more chaperones may be used in combination. Co-expression of one or more of helper proteins and/or factors, such as chaperones, with the target protein can increase the levels of soluble protein. In one embodiment, the one or more protein capable of facilitating protein folding is FkpA, Skp, SurA, PPiA and PPiD. In other embodiments, the one or more protein capable of facilitating protein secretion or translocation, is SecY, SecE, SecG, SecYEG, SecA, SecB, FtsY and Lep. In one other embodiment, the one or more protein capable of facilitating disulfide bond formation is DsbA, DsbB, DsbD, DsbG. In some embodiments the disulfide bond oxidizing and isomerizing components can be from eukaryotic sources such as protein disulfide isomerase (PDI) from yeast or human.

Periplasmic chaperones, including but not limited to Skp and FkpA, have been shown to improve periplasmic production of antibody fragments (Hayhurst et al., Protein Expr. Purif., 15, 336-343, 1999; Hayhurst et al., J. Immunol. Meth., 276, 185-196, 2003; Padiolleau-Lefèvre et al., Immunol. Lett., 103, 39-44, 2006; Zhang, et al., Biotechniques, 35, 1032-1038, 2003; Bothmann et al., J. Biol. Chem., 275, 17100-17105, 2000; Ow et al., Microb. Cell Fact., 9, 22, 2010). In *E. coli*, FkpA and Skp are two well-known bi-functional periplasmic chaperones having peptidyl prolyl isomerase activities. Skp and FkpA are molecular chaperones with general ability to refold misfolded proteins and prevent their aggregation into insoluble inclusion bodies in the periplasm. Skp a 17-kDa homotrimeric protein that facilitates proper folding of newly synthesized outer-membrane proteins and helps to maintain their solubility, and FkpA a 26-kDa homodimeric protein that exhibits chaperone activity and peptidyl-prolyl isomerase (PPlase) activity.

In some embodiments, proteins capable of facilitating disulfide bond formation, including disulfide bond oxidizing and isomerizing chaperones and enzymes, can be utilized. Protein disulfide isomerase is an enzyme that catalyzes the formation and breakage of disulfide bonds between cysteine residues within proteins as they fold. In *E. coli* such disulfide isomerases (helper proteins) include DsbA, DsbB, DsbC, DsbD, or DsbG. Co-expression of proteins which catalyze the formation of disulfide bonds to improve protein expression in a host cell are well known to those of skill in the art. For example, WO1998/56930 discloses a method for producing heterologous disulfide bond-containing polypeptides in bacterial cells wherein a prokaryotic disulfide isomerase, such as DsbC or DsbG is co-expressed with a eukaryotic polypeptide; U.S. Pat. No. 6,673,569 discloses an artificial operon comprising polynucleotides encoding each of DsbA, DsbB, DsbC and DsbD for use in producing a foreign protein; EP Patent No. 0786009 discloses a process for producing a heterologous polypeptide in bacteria wherein the expression of nucleic acid encoding DsbA or DsbC is induced prior to the induction of expression of nucleic acid encoding the heterologous polypeptide. Further, some protein isomerases, for example DsbC, are bifunctional and critical in protein expression as observed in the art for FkpA.

It is known in the art that in some bacterial plasmid segregation systems, specific genes known as plasmid partition locus (par) are involved in the killing of daughter cells which had lost the plasmid during cell division (Ebersbach G. and Gerdes K., Annu. Rev. Genet. 2005 39, 453). Additionally, other findings in the literature have demonstrated that a 580-bp minimal partition B (parB) locus, originally from *E. coli* plasmid R1, mediates maintenance and stability in many bacteria including *E. coli* (Gerdes K., Nature Biotech. 1988 6, 1402-1405; Gerdes K. et. al., Mol. Microbiol. 1990 4, 1807; Gerdes K. and Neilsen Al, J. Mol. Biol. 1992 226, 637). The parB (partition B) locus of plasmid R1 controls plasmid stability and encodes the hok and sok genes. Those cells that at cell division lose a parB-carrying plasmid are rapidly killed (so-called post-segregational killing; Gerdes et al., 1986a). The hok gene, which is responsible for the host cell killing is located in the left part of the parB region. This gene is regulated by the sok gene-encoded repressor, a small anti-sense RNA complementary to the hok mRNA, at the translational level. The sok gene (suppression of killing) encoding a trans-acting antagonist, of hok gene activity is located just upstream from the entire gene coding frame (Gerdes et al., 1986a). The hok mRNA is highly stable, whereas the sok RNA quickly deteriorates. This mechanism of action, post-segregational killing, occurs as the sok RNA molecule rapidly disappears in cells that have lost a parB-carrying plasmid. This in turns leads to translation of the stable hok mRNA. Subsequently the Hok protein is synthesized and promotes killing of plasmid free cells. Thus, to improve plasmid retention in the production strains of the invention disclosure, parB locus gene was utilized in the design and engineering of the synthetic expression plasmids. As observed in the Examples herein, parB locus was significant in increasing the yield of recombinant protein expression. In some embodiments of the invention, the position and orientation of the parB locus in relation to the gene of interest also influenced the increase of recombinant protein expression.

Proteases play an important role in turning over old and miss-folded proteins in the *E. coli* periplasm and cytoplasm. Bacterial proteases act to degrade the recombinant protein of interest, thereby often significantly reducing the yield of active protein. Such proteases include but not limited to Protease III (ptr), DegP, OmpT, Tsp, prlC, ptrA, ptrB, pepA-T, tsh, espc, eatA, clpP and Ion. The periplasmic serine endo-protease Prc (for processing of C-terminus), also known as tail-specific protease (Tsp) is believed to be responsible for Fab cleavage (Chen C. et al. Biotechnology and Bioengineering 2004 85, 463). Prc is believed to recognize and bind to the C-terminus of a protein and then cleave at loose or unfolded regions within the protein sequence (Keiler et al. Protein Science 1995 4, 1507). The site of cleavage is determined by protein secondary or tertiary structure and not primary sequence. Prc has a broad sequence specificity with respect to the proteolysis site. It is known in the art that the C-terminal sequence of a protein can affect its cleavage by Prc, and that modifying the C-terminal sequence can change the amount of cleavage of that protein by Pre (Keiler K C and Sauer R T, The Journal of Biological Chemistry 1996 271, 2589). Thus, in some embodiments, the present invention examines the involvement of protease in modulating or regulating protein yield.

Orthogonal tRNA Technology

In optimizing protein expression in a prokaryotic system, for example *E. coli*, the present invention utilizes protein, including difficult-to-express (DTE) antibody fragments, in which a non-naturally encoded amino acid is incorporated. Use of non-natural amino acid incorporation technology in *Escherichia coli*, is well known in the art. This technology uses orthogonal tRNA/aminoacyl-tRNA synthetase pairs that function in prokaryotic species to site specifically incorporate unnatural amino acids in response to selector codons. See, for example, WO 2002/085923, WO 2002/086075, WO 2004/09459, WO 2005/019415, WO 2005/007870 and WO 2005/007624 the content of which is incorporated by reference in its entirety. See also, Wang and Schultz, "Expanding the Genetic Code," Angewandte Chemie Int. Ed., 44(1):34-66, 2005, the content of which is incorporated by reference in its entirety. The incorporation of the unnatural amino acids into proteins can be programmed to occur at any desired position by engineering the polynucleotide encoding the protein (or gene) of interest to contain a selector codon that signals the incorporation of the unnatural amino acid. Selector codons of the present includes, for example a unique three base codon, a nonsense codon, such as a stop codon.

To add additional reactive unnatural amino acids to the genetic code, new orthogonal pairs comprising an aminoacyl-tRNA synthetase and a suitable tRNA are needed that can function efficiently in the host translational machinery, but that are "orthogonal" to the translation system at issue, meaning that it functions independently of the synthetases and tRNAs endogenous to the translation system. Desired characteristics of the orthologous pair include tRNA that decode or recognize only a specific codon, for example, a selector codon, that is not decoded by any endogenous tRNA, and aminoacyl-tRNA synthetases that preferentially aminoacylate (or "charge") its cognate tRNA with only one specific unnatural amino acid. The O-tRNA is also not typically aminoacylated by endogenous synthetases. For example, in *E. coli*, an orthogonal pair will include an aminoacyl-tRNA synthetase that does not cross-react with any of the endogenous tRNA, for example, which there are 40 in *E. coli*, and an orthogonal tRNA that is not aminoacylated by any of the endogenous synthetases, for example, of which there are 21 in *E. coli*.

A wide variety of orthogonal tRNAs and aminoacyl tRNA synthetases have been described in the art for inserting particular synthetic amino acids into polypeptides, and are generally suitable for use in the present invention. For example, keto-specific O-tRNA/aminoacyl-tRNA synthetases are described in Wang et al., *Proc. Natl. Acad. Sci. USA* 100:56-61 (2003) and Zhang et al., *Biochem*. 42(22): 6735-6746 (2003). Exemplary O-RS, or portions thereof, are encoded by polynucleotide sequences and include amino acid sequences disclosed in U.S. Pat. Nos. 7,045,337 and 7,083,970, each incorporated herein by reference. Corresponding O-tRNA molecules for use with the O-RSs are also described in U.S. Pat. Nos. 7,045,337 and 7,083,970 which are incorporated by reference herein. Additional examples of O-tRNA/aminoacyl-tRNA synthetase pairs are described in WO 2005/007870, WO 2005/007624; and WO 2005/019415.

Several other orthogonal pairs have been reported. Glutaminyl (see, e.g., Liu et al., (1999) PNAS 96:4780-4785), aspartyl (see, e.g., Pastrnak et al., (2000) Helv. Chim. Acta 83:2277-2286), and tyrosyl (see, e.g., Ohno et al., (1998) J. Biochem. (Tokyo, Jpn.) 124:1065-1068; and, Kowal et al., (2001) PNAS 98:2268-2273) systems derived from *S. cerevisiae* tRNA's and synthetases have been described for the potential incorporation of unnatural amino acids in *E. coli*. Systems derived from the *E. coli* glutaminyl (see, e.g., Kowal et al., (2001) PNAS 98:2268-2273) and tyrosyl (see, e.g., Edwards et al., (1990) Mol. Cell. Biol. 10:1633-1641) synthetases have been described for use in *S. cerevisiae*. The *E. coli* tyrosyl system has been used for the incorporation of 3-iodo-L-tyrosine in vivo, in mammalian cells. See, Sakamoto et al., (2002) Nucleic Acids Res. 30:4692-4699.

In general, when an orthogonal pair recognizes a selector codon and loads an amino acid in response to the selector codon, the orthogonal pair is said to "suppress" the selector codon. That is, a selector codon that is not recognized by the translation system's (e.g., the cell's) endogenous machinery is not ordinarily translated, which can result in blocking production of a polypeptide that would otherwise be translated from the nucleic acid, An O-tRNA of the invention recognizes a selector codon and includes at least about 45%, 50%, 60%, 75%, 80%, or 90% or more suppression efficiency in the presence of a cognate synthetase in response to a selector codon as compared to the suppression efficiency of an O-tRNA comprising or encoded by a polynucleotide sequence. The O-RS aminoacylates the O-tRNA with an unnatural amino acid of interest. The cell uses the O-tRNA/O-RS pair to incorporate the unnatural amino acid into a growing polypeptide chain, for example, via a nucleic acid that comprises a polynucleotide that encodes a polypeptide of interest, where the polynucleotide comprises a selector codon that is recognized by the O-tRNA. In certain desirable aspects, the cell can include an additional O-tRNA/O-RS pair, where the additional O-tRNA is loaded by the additional O-RS with a different unnatural amino acid. For example, one of the O-tRNAs can recognize a four base codon and the other can recognize a stop codon. Alternately, multiple different stop codons or multiple different four base codons can specifically recognize different selector codons.

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, in a single polynucleotide encoding the protein of interest.

In one embodiment, the methods involve the use of a selector codon that is a stop codon for the incorporation of one or more unnatural amino acids in vivo. For example, an O-tRNA is produced that recognizes the stop codon, including but not limited to, UAG, and is aminoacylated by an O-RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5'-3' Exonucleases in phosphorothioate-based oligonucleotide-directed mutagenesis. Nucleic Acids Res, 16:791-802. When the O-RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., Biochemistry, 32:7939 (1993). In this case, the synthetic tRNA competes with the naturally occurring tRNAArg, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., Kowal and Oliver, Nucl. Acid. Res., 25:4685 (1997). Components of the present invention can be generated to use these rare codons in vivo.

Selector codons also comprise extended codons, including but not limited to, four or more base codons, such as, four, five, six or more base codons. Examples of four base codons include, but are not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., Exploring the Limits of Codon and Anticodon Size, Chemistry and Biology, 9:237-244. 2002; Magliery, Expanding the Genetic Code: Selection of Efficient Suppressors of Four-base Codons and Identification of "Shifty" Four-base Codons with a Library Approach in *Escherichia coli*, J. Mol. Biol. 307: 755-769, 2001.

For example, four-base codons have been used to incorporate unnatural amino acids into proteins using in vitro biosynthetic methods. See, e.g., Ma et al., Biochemistry, 32:7939, 1993; and Hohsaka et al., J. Am. Chem. Soc., 121(51), pp 12194-12195, 1999. CGGG and AGGU were used to simultaneously incorporate 2-naphthylalanine and an NBD derivative of lysine into streptavidin in vitro with two chemically acylated frameshift suppressor tRNAs. (See, e.g., Hohsaka et al., supra). In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., J. Mol. Biol., 298:195, 2000. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., An unnatural base pair for incorporating amino acid analogues into protein, Nature Biotechnology, 20:177-182, 2002. See, also, Wu, Y., et al., J. Am. Chem. Soc. 124:14626-14630, 2002. Other relevant publications are listed below In certain embodiments of the invention, a cell such as an *E. coli* cell that includes an orthogonal tRNA (O-tRNA), an orthogonal aminoacyl-tRNA synthetase (O-RS), an unnatural amino acid and a nucleic acid that comprises a polynucleotide that encodes a polypeptide of interest, where the polynucleotide comprises the selector codon that is recognized by the O-tRNA. The translation system can also be a cell-free system, for example, any of a variety of commercially available "in vitro" transcription/translation systems. Examples of pairs include a mutRNATyr-mutTyrRS pair, such as a mutRNATyr-SS 12TyrRS pair, a mutRNALeu-mutLeuRS pair, a mutRNAThr-mutThrRS pair, a mutRNA-Glu-mutGluRS pair, or the like.

Non-Natural Amino Acids

The present disclosure includes antibody fragments having a non-naturally or unnaturally encoded amino acid site specifically incorporated therein. Methods for site specifically introducing non-natural amino acids in an antibody or antibody fragment are described in the art, see for example in WO2010/011735 and in WO2005/074650. Typically, the unnatural amino acids of the invention are selected or designed to provide additional characteristics unavailable in the twenty natural amino acids. For example, unnatural amino acids are optionally designed or selected to modify the biological properties of a protein into which they are incorporated. For example, the following properties are optionally modified by inclusion of an unnatural amino acid into a protein: toxicity, biodistribution, solubility, stability (for example, thermal, hydrolytic, oxidative, resistance to enzymatic degradation, and the like), facility of purification and processing, structural properties, spectroscopic properties, chemical and/or photochemical properties, catalytic activity, redox potential, half-life, ability to react with other molecules (either covalently or noncovalently), or the like.

As used herein, the term "non-natural or unnatural amino acid" refers to any amino acid, modified amino acid, and/or amino acid analogue, that is not one of the 20 common naturally occurring amino acids or seleno cysteine or pyrrolysine. Non-natural amino acids of the invention can be naturally occurring compounds other than the twenty alpha-amino acids known in the art. Non-natural amino acids can include but are not limited to p-ethylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenyl alanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine and p-nitro-L-phenylalanine and can include L and D-enantiomers of such. Non-natural amino acids of the invention can comprise an alkyl-, aryl-, acyl-, hydrazine, cyano-, halo-, hydrazide, alkenyl, ether, borate, boronate, phospho, phosphono, phosphine, enone, imine, ester, hydroxylamine, amine, and the like, or any combination thereof. Other non-natural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photo caged and/or photoisomerizable amino acids, biotin or biotin-analogue containing amino acids, keto containing amino acids, glycosylated amino acids, a saccharide moiety attached to the amino acid side chain, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, greater than about 5, greater than about 10 carbons, etc.), carbon-linked sugar-containing amino acids, amino thioacid containing amino acids, and amino acids containing one or more toxic moiety.

Non-natural amino acids based on natural amino acids, such as tyrosine, glutamine, phenylalanine, and the like are included in the present invention. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, alpha-hydroxy derivatives, beta-substituted derivatives, cyclic derivatives, and amide substituted glutamine derivatives. Example phenylalanine analogs include, but are not limited to, meta-substituted phenylalanines, wherein the substituent comprises a hydroxy group, a methoxy group, a methyl group, an allyl group, an acetyl group, or the like. Specific examples of unnatural amino acids include, but are not limited to, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAc beta-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like.

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., Fessenden, R & Fessenden, J, Organic Chemistry, Secod Edition, Willard Grant Press, Boston Mass., 1982; March, J., Advanced Organic Chemistry, Third Edition, Wiley and Sons, New York, 1985; and Carey, F. & Sundberg, R., Advanced Organic Chemistry, Third Edition, Parts A and B, Plenum Press, New York, 1990). Additional publications describing the synthesis of unnatural amino acids include, e.g., WO 2002/085923 entitled "In vivo incorporation of Unnatural Amino Acids"; Matsoukas et al., J. Med. Chem., 38, 4660-4669, 1995; King, F. E. & Kidd, D. A. A., A New Synthesis of Glutamine and of gamma-Dipeptides of Glutamic Acid from Phthylated Intermediates, J. Chem. Soc., 3315-3319, 1949; Friedman, O. M. & Chatterrji, R., Synthesis of Derivatives of Glutamine as Model Substrates for Anti-Tumor Agents, J. Am. Chem. Soc. 81, 3750-3752, 1959; Craig, J. C. et al., Absolute Configuration of the Enantiomers of 7-Chloro-4 [[4-(diethylamino)-1-methylbutyl]amino]quinoline (Chloroquine), J. Org. Chem. 53, 1167-1170, 1988; Azoulay, M., Vilmont, M. & Frappier, F., Glutamine analogues as Potential Antimalarials, Eur. J. Med. Chem. 26, 201-5, 1991; Koskinen, A. M. P. & Rapoport, H. Synthesis of 4-Substituted Prolines as Conformationally Constrained Amino Acid Analogues, J. Org. Chem., 54, 1859-1866, 1989; Christie, B. D. & Rapoport, H., Synthesis of Optically Pure Pipecolates from L-Asparagine. Application to the Total Synthesis of (+)-Apovincamine through Amino Acid Decarbonylation and Iminium Ion Cyclization, J. Org. Chem. 1989:1859-1866, 1985; Barton et al., Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives, Tetrahedron Lett, 43:4297-4308, 1987; and, Subasinghe et al., Quisqualic acid analogues: synthesis of beta-heterocyclic 2-aminopropanoic acid derivatives and their activity at a novel quisqualate-sensitized site, J. Med. Chem. 35:4602-7, 1992. See also, International Publication WO 2004/058946, entitled "Protein Arrays," filed on Dec. 22, 2003.

The incorporation of an unnatural amino acid can be done for a variety of purposes, including but not limited to, modulating the interaction of a protein with its receptor or one or more subunits of its receptor, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: receptor binding, toxicity, biodistribution, structural properties, spectroscopic properties, chemical and/or photochemical properties, catalytic ability, half-life (including but not limited to, serum half-life), ability to react with other molecules, including but not limited to, covalently or non-covalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function*, Current Opinion in Chemical Biology, 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein. By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish et al., (1996) J. Am. Chem. Soc., 118:8150-8151; Mahal et al., (1997) Science, 276:1125-1128; Wang et al., (2001) Science 292:498-500; Chin et al., (2002) J. Am. Chem. Soc. 124:9026-9027; Chin et al., (2002) Proc. Natl. Acad. Sci., 99:11020-11024; Wang et al., (2003) Proc. Natl. Acad. Sci., 100:56-61; Zhang et al., (2003) Biochemistry, 42:6735-6746; and Chin et al., (2003) Science, 301:964-7, all of which are incorporated by reference herein. This allows selective labeling of virtually any protein with a host of reagents including fluorophores, crosslinking agents, saccharide derivatives and cytotoxic molecules. See U.S. Pat. No. 6,927,042 entitled "Glycoprotein synthesis," which is incorporated by reference herein. Post-translational modifications, including but not limited to, through an azido amino acid, can also made through the Staudinger ligation (including but not limited to, with triarylphosphine reagents). See, e.g., Kiick et al., Incorporation of azides into recombinant proteins for chemoselective modification by the Staudinger ligation, PNAS 99:19-24, 2002.

Expression Systems

To obtain high level expression of a cloned polynucleotide, one typically subclones polynucleotides encoding a protein or polypeptide of interest into an expression vector that contains a strong promoter to direct transcription, a transcription/translation terminator, and if for a nucleic acid encoding a protein, a ribosome binding site for translational initiation. Suitable bacterial promoters are known to those of ordinary skill in the art and described, e.g., in Sambrook et al. and Ausubel et al.

Bacterial expression systems for expressing protein of interest of the invention are available in, including but not limited to, *E. coli, Bacillus* sp., *Pseudomonas* fluorescens, *Pseudomonas aeruginosa, Pseudomonas putida*, and *Salmonella* (Palva et al., Gene 22:229-235, 1983; Mosbach et al., Nature 302:543-545, 1983). Kits for such expression systems are commercially available.

A recombinant host cell of the present invention provides the ability to synthesize proteins that comprise unnatural amino acids in large useful quantities. In one aspect, the composition optionally includes, including but not limited to, at least 2 micrograms, at least 5 micrograms, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 2 micrograms of protein per liter, 5 micrograms of protein per liter, 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L or more).

The nucleotide sequence encoding a protein of interest of the may or may not also include sequence that encodes a signal peptide. The signal peptide is present when the polypeptide is to be secreted from the cells in which it is expressed. Such signal peptide may be any sequence. The signal peptide may be prokaryotic or eukaryotic. (Coloma, J. Imm. Methods, 152, 89-104, 1992) describe a signal peptide for use in mammalian cells (murine Ig kappa light chain signal peptide). Other signal peptides include but are not limited to, the α-factor signal peptide from *S. cerevisiae* (U.S. Pat. No. 4,870,008 which is incorporated by reference herein), the signal peptide of mouse salivary amylase (Hagenbuchle et al., Nature 289, 643-646, 1981), a modified carboxypeptidase signal peptide (Valls et al., Cell 48, 887-897, 1987), the yeast BAR1 signal peptide (WO 87/02670, which is incorporated by reference herein), and the yeast aspartic protease 3 (YAPS) signal peptide (cf. Egel-Mitani et al., Yeast 6, 127-137, 1990).

Bacterial expression techniques are known to those of ordinary skill in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) (Raibaud et al., Annu. Rev. Genet, 18:173, 1984). Regulated expression may therefore be either positive or negative, thereby either enhancing or reducing transcription.

The term "bacterial host" or "bacterial host cell" refers to a bacteria that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a protein of interest of the invention, are included in the progeny intended by this definition.

The selection of suitable host bacteria for expression proteins of the invention is known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, CA); and the American Type Culture Collection ("ATCC") (Manassas, VA). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. Other examples of suitable *E. coli* hosts include, but are not limited to, strains of BL21, DH10B, or derivatives thereof. In another embodiment of the methods of the present invention, the *E. coli* host is a protease minus strain including, but not limited to, OMP- and LON-. The host cell strain may be a species of *Pseudomonas*, including but not limited to, *Pseudomonas fluorescens, Pseudomonas aeruginosa*, and *Pseudomonas putida. Pseudomonas fluorescens* biovar 1, designated strain MB101, is known to be useful for recombinant production and is available for therapeutic protein production processes. Examples of a *Pseudomonas* expression system include the system available from The Dow Chemical Company as a host strain (Midland, MI available on the worldwideweb at dow.com).

Once a recombinant host cell strain has been established (i.e., the expression construct has been introduced into the host cell and host cells with the proper expression construct are isolated), the recombinant host cell strain is cultured under conditions appropriate for production of the protein or polypeptide of interest. As will be apparent to one of skill in the art, the method of culture of the recombinant host cell strain will be dependent on the nature of the expression construct utilized and the identity of the host cell. Recombinant host strains are normally cultured using methods that are known to those of ordinary skill in the art. Recombinant host cells are typically cultured in liquid medium containing assimilatable sources of carbon, nitrogen, and inorganic salts and, optionally, containing vitamins, amino acids, growth factors, and other proteinaceous culture supplements known to those of ordinary skill in the art. Liquid media for culture of host cells may optionally contain antibiotics or antifungals to prevent the growth of undesirable microorganisms and/or compounds including, but not limited to, antibiotics to select for host cells containing the expression vector.

Recombinant host cells may be cultured in batch or continuous formats, with either cell harvesting or harvesting of culture supernatant in either batch or continuous formats. For production in prokaryotic host cells, batch culture and cell harvest are preferred.

The proteins of interest of the present invention can be purified after expression in recombinant systems. The proteins of interest may be purified from host cells or culture medium by a variety of methods known to the art. Proteins of interest of the invention produced in bacterial host cells may be poorly soluble or insoluble (in the form of inclusion bodies). In one embodiment of the present invention, amino acid substitutions may readily be made in the protein or polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods known to those of ordinary skill in the art. Host cell disruption or homogenization may be performed using well known techniques including, but not limited to, enzymatic cell disruption, sonication, dounce homogenization, or high pressure release disruption.

Insoluble or precipitated proteins or polypeptide may then be solubilized using any of a number of suitable solubilization agents known to the art. The proteins or polypeptide may be solubilized with urea or guanidine hydrochloride. The volume of the solubilized proteins or polypeptide should be minimized so that large batches may be produced using conveniently manageable batch sizes. This factor may be significant in a large-scale commercial setting where the recombinant host may be grown in batches that are thousands of liters in volume. In addition, when manufacturing proteins or polypeptide in a large-scale commercial setting, in particular for human pharmaceutical uses, the avoidance of harsh chemicals that can damage the machinery and container, or the protein product itself, should be avoided, if possible.

In some instances, the soluble protein may be secreted into the periplasmic space or into the culture medium. In addition, soluble protein may be present in the cytoplasm of the host cells. It may be desired to concentrate soluble protein prior to performing purification steps. Standard techniques known to those of ordinary skill in the art may be used to concentrate soluble protein for example, cell lysates or culture medium. In addition, standard techniques known to those of ordinary skill in the art may be used to disrupt host cells and release soluble protein from the cytoplasm or periplasmic space of the host cells.

Methodology and Techniques

The present disclosure encompasses methodologies and routine techniques well known in the art. These include conventional methods of molecular biology, recombinant DNA techniques, biochemistry and cell biology, all within the skill of the art. Such techniques are explained fully in the literature, such as Molecular Cloning: A Laboratory Manual, Third Edition (Sambrook et at, Eds., Cold Spring Harbor Press, Cold Spring Harbor, NY, 2001); Oligonucleotide Synthesis: Methods And Applications (Methods in Molecular Biology), (Herdewijn, P., Ed., Humana Press, Totowa, NJ); Oligonucleotide Synthesis (Gait, M. J., Ed., 1984); Methods In Molecular Biology, (Humana Press, Totowa, NJ); Cell Biology: A Laboratory Notebook (Cellis, J. E., Ed., Academic Press, New York, NY, 1998); Animal Cell Culture (Freshney, R. I., Ed., 1987); Introduction To Cell And Tissue Culture (Mather, J. P. and Roberts, P. E., Eds., Plenum Press, New York, NY, 1998); Cell And Tissue Culture: Laboratory Procedures (Doyle, A. et al., Eds., John Wiley and Sons, Hoboken, NJ, 1993-8); Gene Transfer Vectors For Mammalian Cells (Miller, J. M. et al. Eds., Cold Spring Harbor Press, Cold Spring Harbor, NY, 1987); Current Protocols In Molecular Biology (Ausubel, F. M. et al., Eds., Greene Pub. Associates, New York, NY, 1987); PCR: The Polymerase Chain Reaction, (Mullis, K. et al., Eds., Birkhauser, Boston, MA, 1994); Short Protocols In Molecular Biology (John Wiley and Sons, Hoboken, NJ, 1999); Immunobiology 7 (Janeway, C. A. et al., Garland Science, London, U K, 2007); Antibodies (P. Finch, Stride Publications, Devoran, U K, 1997); Antibodies: A Practical Approach (D. Catty., ed., Oxford University Press, USA, New York, NY, 1989); Monoclonal Antibodies: A Practical Approach (Shepherd, P. et al. Eds., Oxford University Press, USA, New York NY, 2000); Using Antibodies: A Laboratory Manual (Harlow, E. et al. Eds., Cold Spring Harbor Laboratory Press, Cold Spring Harbor, NY, 1998); The Antibodies (Zanetti, M. et al. Eds., Harwood Academic Publishers, London, U K, 1995).

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector.

Several well-known methods of introducing target nucleic acids into cells are available, any of which can be used in the invention. These include fusion of the recipient cells with bacterial protoplasts containing the DNA, electroporation, projectile bombardment, and infection with viral vectors etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., EasyPrep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, Gene 8:81, 1979; Roberts, et al., Nature, 328:731, 1987; Schneider, E., et al., Protein Expr. Purif. 6(1):10-14, 1995; Ausubel, Sambrook, Berger (all supra). A catalogue of bacteria and bacteriophages useful for cloning is provided, e.g., by the ATCC, e.g., The ATCC Catalogue of Bacteria and Bacteriophage (1992) Gherna et al. (eds) published by the ATCC. Additional basic procedures for sequencing, cloning and other aspects of molecular biology and underlying theoretical considerations are also found in Watson et al. (1992) Recombinant DNA Second Edition Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, TX available on the worldwideweb at mcrc.com), The Great American Gene Company (Ramona, CA available on the worldwideweb at genco.com), ExpressGen Inc. (Chicago, IL available on the worldwideweb at expressgen.com), Operon Technologies Inc. (Alameda, CA) and many others.

Kits

Any of the compositions described herein can be assembled together in a kit, in a suitable container means. More particularly, all or a subset of the components for designing and constructing or engineering a vector and/or plasmid of the present invention can be packaged together in a kit. The one or more components of the present invention can be packaged separately or together. In some embodiments, it is preferable to package the vector and/or plasmid together with one or more components disclosed herein. In embodiments of the invention, the proteins, peptides, polypeptides (including antibody fragments), or nucleic acid encoding such can be packaged together, or as single molecules, or as a set of molecules. Alternatively, the components disclosed herein can be packaged and sold individually along with instructions, in printed form or on machine-readable media, describing how they can be used in conjunction with each other to design and construct a vector and/or plasmid, as disclosed herein.

In one embodiment, the kit can have a single container means, and/or it can have distinct container means for additional compounds. The components of the present invention may be provided in in liquid form or in dry powder form. In instances where the components are provided in one or more liquid solutions, the liquid solution is an aqueous solution, with a sterile aqueous solution being particularly preferred. In other instances, the components of the kit can be provided as dried powder(s). When components (e.g., reagents) are provided as a dry powder, the powder can be reconstituted by the addition of a suitable solvent. It is envisioned that the solvent can also be provided in another container means. The container means contemplated herein, include in a non-limiting manner, at least one vial, test tube, flask, bottle, and/or other container means.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

Example 1: Engineering of Expression Vectors

Anti-CD3 Fab expression plasmids of the present invention were engineered either by recombination-based cloning method using Gibson Assembly kit (New England Biolabs, MA) or by using QuikChange mutagenesis kit (Agilent Technologies, CA) in *E. coli* NEB5α cloning strain (New England Biolabs, MA) as described below. Table 1 shows three *E. coli* cloning and production hosts, used in this study, and their detailed genotypes.

TABLE 1

*Escherichia coli* Cloning and Production Host Strains and Genotypes

| Strain | Genotypes | Source/Reference |
|---|---|---|
| NEB5α | fhuA2 (argF-lacZ)U169 phoA glnV44 80 (lacZ)M15 gyrA96 recA1 relA1 endA1 thi-1 hsdR17 | NEB#2987 |
| W3110 | F- mcrA mcrB IN(rrnD-rrnE) lambda-rph-1 | ATCC#27325 |
| W3110B60 | F- mcrA mcrB IN(rrnD-rraE) lambda- rph-1 araB::g1-tetA fhuA::dhfr proS-W375R-cat | Ambrx, Inc. |

Gibson Assembly: The primers for amplifying various gene of interests (GOIs) containing donor fragments had about 18-24 base pair (bp) overlap sequence at their 5'-termini with the acceptor vector sequences for homologous recombination and were synthesized at Integrated DNA Technologies ((IDT), San Diego, CA)). The PCR fragments were amplified using high fidelity DNA polymerase mix, Pfu Ultra II Hotstart PCR Master Mix (Agilent Technologies, CA). The PCR products were digested with Dpn1 restriction enzyme (NEB) for 2 hours at 37° C. to remove plasmid background followed by column purification using Qiagen PCR column purification kit (Qiagen) and quantitated by Nanodrop (ThermoFisher). The acceptor vectors were linearized by digesting with unique restriction enzymes (NEB, MA) within the vector for 3 to 5 hours at supplier recommended temperatures, PCR column purified and quantitated. The donor inserts and appropriately prepared acceptor vectors were mixed at a 3:1 molar ratio, incubated at 50° C. for 15 min, using Gibson Assembly kit (NEB), and then used for transformation into *E. coli* NEB5α strain (NEB).

The recombinants were recovered by plating Gibson Assembly mix on to LB agar plates containing appropriate antibiotics. The next day, 4 to 6 well-isolated single colonies were inoculated into 5 mL LB+50 µg/mL kanamycin sulfate (Sigma) or carbenicillin 100 µg/mL (Teknova) media and grown overnight at 37° C. The recombinant plasmids were isolated using Qiagen plasmid DNA mini-prep kit (Qiagen) and verified by DNA sequencing (Eton Biosciences, CA). The complete GOI region plus 100 bp upstream and 100 bp downstream sequences were verified by using gene-specific sequencing primers.

QuikChange Mutagenesis (QCM): Amber variants containing TAG stop codon were created by using QuikChange Lightning site directed mutagenesis kit (Agilent Technologies). QCM oligonucleotides were designed using QuikChange Web Portal (Agilent Technologies Inc.), and ordered from IDT (San Diego, CA). The QCM PCR mix contained 5 µl of 10× buffer, 2.5 µl of dNTP Mix, 1 µl (100 ng) of plasmid template, 1 µl of oligo mix (10 uM conc each), 1 µl of QuikChange Lightning enzyme, 2.5 µl of Quick solution and 37 µl of distilled water (DW). The DNA was amplified using the PCR program recommended by the kit for 18 cycles only.

After the completion of the PCR reaction, the mix was digested with Dpn1 enzyme that came with the kit (Agilent Technologies) for 2-3 hours at 37° C. and ran on a gel to check the presence of amplified PCR product. Then, 2.5 to 5 µl of PCR product was transformed into E. coli NEB5α strain. The recombinant plasmids from 4 to 6 colonies were then isolated and sequence verified as described for Gibson Assembly above.

Example 2: Engineering of Expression Strains

To prepare production strains of the present invention, chemically competent E. coli W3110B60 host cells were transformed with sequence-verified plasmid DNA (50 ng), the recombinant cells were selected on 2xYT+1% glucose agar plates containing 50 µg/mL kanamycin sulfate (Sigma) (or carbenicillin 100 µg/mL, Teknova), and incubated overnight at 37° C. A single colony from the fresh transformation plate was then propagated thrice on 2xYT+1% glucose agar plates containing 50 µg/mL kanamycin sulfate or carbenicillin 100 µg/mL by sequential triple-streaking and incubating overnight at 37° C. Finally, a single colony from the third-streaked plate was inoculated into 20 mL Super Broth (Fisher-Optiglow™) containing 50 µg/mL kanamycin sulfate (Sigma) (or carbenicillin 100 µg/mL, Teknova), and incubated for overnight at 37° C. and 250 rpm. The overnight grown culture was then diluted with glycerol to a final glycerol concentration of 20% (w/v). This cell suspension was then dispensed into 1 mL aliquots into several cryovials and frozen at −80° C. as production strain vials.

After the generation of glycerol vials of the production strains as described above, the production strains were further validated by DNA sequencing and phenotypic characterization of antibiotic resistance markers. To confirm that the production strain vial had the correct plasmid in the production host, the plasmid was sequence verified. Twenty (20) mL LB containing 50 µg/mL kanamycin sulfate (or carbenicillin 100 µg/mL) was inoculated with a stab from a glycerol vial of the clone and grown at 37° C., 250 rpm overnight. The plasmid DNA was isolated using Qiagen Miniprep Kit and the presence of intact GOI ORF in the isolated plasmid was confirmed by DNA sequencing (Eton Biosciences, CA).

To further verify the strain genotype of each production strain, cells from the same vial were streaked onto four separate plates of LB: LB containing 50 ug/mL kanamycin sulfate, LB containing 15 ug/mL tetracycline, LB containing 34 ug/mL chloramphenicol and LB containing 75 ug/mL trimethoprim. All plates were then checked for positive growth, as expected with the strain genotype of W3110B60 production host strain, disclosed in Table 1.

Example 3: Fermentation Process

The fermentation process for production of anti-CD3 Fab-pAcF consists of two stages: (i) inoculum preparation and (ii) fermentor production. The inoculum is started from a single glycerol vial, thawed, diluted 1:1000 (v/v) into 50 mL of defined seed medium in a 250 mL baffled Erlenmeyer flask, and incubated at 37° C. and 250 rpm. Prior to use, the fermentor is cleaned and autoclaved. A specified amount of basal medium is added to the fermentor and steam sterilized. Specified amounts of kanamycin sulfate solution, feed medium and P2000 antifoam are added to the basal medium prior to inoculation. All solutions added to the fermentor after autoclaving are either 0.2 filtered or autoclaved prior to aseptic addition. The production fermentor is inoculated at a target $OD_{600}$ of 0.0004 by aseptic transfer of the contents of the inoculum. After inoculation, the culture is sampled at appropriate intervals for determination of $OD_{600}$. Temperature, pH and dissolved oxygen are monitored and controlled at the specified set points of 37° C., 7.0, and >30%, respectively. The pH is controlled by the addition of ammonium hydroxide solution or sulfuric acid. Dissolved oxygen is controlled by varying the agitation speed and by increasing the composition of oxygen in the sparged air/oxygen mixture. Antifoam is added during the fermentation process to control foaming.

When the cell density reaches an $OD_{600}$ of >25, a bolus of feed medium is added. When the cell density reaches an $OD_{000}$ of >50, a feed medium is added at a constant flow rate of 0.094 mL/L-start volume/minute for 32 hours until it is reduced to 0.052 mL/L-start volume/minute until the end of fermentation. Immediately after feed start, a specified amount of pAcF solution is added aseptically to allow incorporation of pAcF into the protein amino acid sequence. Simultaneously, the temperature is shifted from 37° C. used during growth to 27° C. for production. Production is controlled by the phoA promoter and starts when phosphate levels in the medium are depleted. The harvest is initiated approximately 24 and 48 hours after induction for short and long fermentation processes, respectively.

Example 4: Plasmid Retention Assay

To measure plasmid retention of fermentation samples, glycerol (20% v/v) was added to 1 mL fermentation broth at harvest and stored at −80° C. for future analysis. From this sample, 100 µL was taken and serially diluted into 900 µL of LB broth through $10^{-1}$, $10^{-2}$, $10^{-3}$, $10^{-4}$, $10^{-5}$, $10^{-6}$, $10^{-7}$ and $10^{-8}$ dilutions. 100 µL of the $10^{-4}$, $10^{-5}$, $10^{-6}$, $10^{-7}$ and $10^{-8}$ dilutions were plated on 2xYT+1% glucose agar plates. The plates were incubated at 30° C. overnight. The next day 100 colonies were picked from the dilution plates with well-isolated colonies and replica plated on 2xYT+1% glucose agar and 2xYT+1% glucose+kanamycin (50 µg/mL) plates. The plates were incubated at 30° C. overnight. After the overnight incubation, the colonies were counted and compared between the 2xYT+1% glucose and 2xYT+1% glucose+kanamycin (50 µg/mL) plates. Plasmid retention is reported as a percentage of colonies that grew on 2xYT+1% glucose plates compared to 2xYT+1% glucose+kanamycin (50 µgimp plates.

Example 5: Product Titer Quantitation

To quantitate product titer, 1 mL of fermentation broth was centrifuged (18,000×g, 5 minutes) at various time points throughout the fermentation process. The supernatant was transferred to a separate 1.5 mL centrifuge tube and both pellet and supernatant were retained and stored at −80° C. for future analysis. Cell pellets were lysed and titer was determined using ELISA or CEX assays as described below.

Sample preparation: 1.0 mL of E. coli cell pellets as described above from fermentation samples (cell paste) were dried and weighed to determine the mass for sample. Lysonase Bioprocessing Reagent (Novagen) and Benzonase Nuclease Reagent (Novagen) were used to chemically lyse the cell paste and were each diluted 1:500 in BugBuster Protein Extraction Reagent (Novagen). 1.0 mL of the Bugbuster/Lysonase/Benzonase mixture was added to 1.0 mL of dried cell paste and the resulting mixture was vortexed vigorously and then placed on a Thermos shaker at 22° C. for 20 minutes with shaking at 1000 revolutions per minute (rpm). After the incubation had been completed, the cellular lysate was centrifuged at 18,000×g for 3 minutes to pellet the cellular debris.

ELISA assay: ELISA, enzyme-linked immunosorbent assay, analyzes samples by immune-enzymatic assay to quantitatively measure the presence of anti-CD3 Fab. The above-mentioned samples were then diluted in Casein Buffer (ThermoFisher) before ELISA analysis. An MSD plate (MSD) was coated with goat anti-human IgG Fd (Southern Biotech) specific to the heavy chain portion of anti-CD3 Fab. The coated ELISA plates were then washed with 1×KPL Buffer (KPL) and blocked with Casein Blocking buffer. Samples containing anti-CD3 Fab and purified standards are then incubated on the plate for 2 hours at room temperature with shaking. The plate was washed with 1×KPL buffer and an additional binding step with goat anti-human kappa biotinylated (Southern Biotech) antibody specific to the light chain portion of anti-CD3 Fab was carried out to ensure only the intact Fab is detected. Sulfo-tag Strepavidin (MSD) was used for the identification and quantification of the captured anti-CD3 Fab proteins. 4×MSD read buffer (MSD) was diluted to 1× and added to each well. The amount of anti-CD3 Fab in the sample is determined by extrapolation against a standard curve.

CEX assay: A 200 μL aliquot of the cellular lysate supernatant as described above was then filtered through a 0.22 μm PVDF centrifugal filter (Millipore) at 18,000×g for 3 minutes. The filtered product was then analyzed by cation exchange chromatography (CEX) to determine the amount of anti-CD3 Fab present in the fermentation samples. The ProPac WCX-10, 4×100 mm CEX column (ThermoFisher) was used to separate the anti-CD3 Fab from the host cell protein contaminants. Mobile Phase A was used to capture anti-CD3 Fab and consisted of 20 mM Sodium Phosphate at pH 6.5 while Mobile Phase B, which was used to elute anti-CD3 Fab and consisted of 20 mM Sodium Phosphate, 200 mM sodium Chloride at pH 6.5. The amount of anti-CD3 Fab in the sample is determined by interpolation of observed peak area against a standard curve.

Example 6: Product Quality and Titer Recovery

Anti-CD3 Fabs of the present invention were each produced in E. coli cells and recovered from the whole cell lysate (WCL) supernatants. Cell lysis was performed at 4° C. Cells are lysed in 100 mM acetic acid, 100 mM NaCl, 1 mM EDTA pH 3.5, in a volume equal to the original fermentation volume, resulting in a post-lysis pH of 4.1-4.2. Following lysis, the WCL is centrifuged at 15,900×g for 30 minutes at 4° C. and filtered (0.8/0.2 micron) to remove precipitated protein and cell debris. Capto S cation exchange chromatography was used to capture anti-CD3 Fab from E. coli WCL supernatant. RP-HPLC analysis was conducted on the Capto S pool to determine the purity of intact Fab versus additional clipped and truncated heavy chain and light chain species that co-purify on the Capto S column along with the intact Fab. Recoverable titer was also estimated by calculating the total amount of protein recovered from the Capto S capture column and multiplying that by the percentage of intact Fab in the Capto S elution pool. The amount of intact Fab was divided by the initial Capto S load volume to estimate the fermentation titer, as the harvested cell pellets were re-suspended back to the fermentation harvest volume for lysis and purification.

Mass spectrometry: 5-10 μg of anti-CD3 Fab sample was loaded onto a reverse phase PLRP-S 2.1 mm×150 mm, 8 μm, 4000 angstroms (A) analytical HPLC column (Agilent) for analysis. Both purified and fraction collected samples were injected onto the analytical column neat. Mobile phase A consisted of 0.05% LC/MS grade TFA (FisherSci) in LC/MS grade HPLC water (FisherSci) while mobile phase B consisted of 0.05% LC/MS grade TFA in LC/MS grade acetonitrile (FisherSci). An Agilent 1200 series HPLC system with a binary pump coupled to an Agilent 6510 ESI Q-Toff-LC/MS system was used for mass spectrum analysis. Agilent Mass Hunter analysis software was used to qualitatively identify the mass of the chromatographically separated peaks. Mass spectrum protein analysis software GPMAW was used to determine the theoretical mass of the anti-CD3 Fab protein primary sequence. The theoretical mass was compared to the measured mass to determine the identity of each peak.

Example 7: Anti-CD3 Fab Expression System in E. coli

FIG. 1 shows the schematic of anti-CD3 Fab expression cassette with the location of UAA incorporation site within the heavy chain constant domain (CH1) indicated. This bi-cistronic operon is driven by the E. coli alkaline phosphatase (phoA) promoter which is induced when phosphate in the medium is depleted. The amino acid sequence of the anti-CD3 Fab is composed of vH and vL (variable region of immunoglobulin heavy and light chains, respectively) coding sequences plus the human gammal (CH1) and kappa (CL) constant regions. A secretion signal peptide, STII, appended to both the heavy and the light chains, directs secretion of Fab into the oxidizing periplasm for proper folding and disulfide bond formation. An amber stop codon (TAG) was engineered at lysine (K) residue 129 in heavy-chain constant domain (CH1) position 129, (refer to herein after as HK129amber or HK129am), (shown in FIG. 1) in the anti-CD3 Fab. This TAG stop codon encoded pAcF at this site with the evolved M. jannaschii pAcF tyrRS/tRNA machinery (see for example, Wang L. et al., Science, 292, 498, 2001; Zhang Z. et. al., Biochemistry, 42, 6735, 2003).

Figure 2:
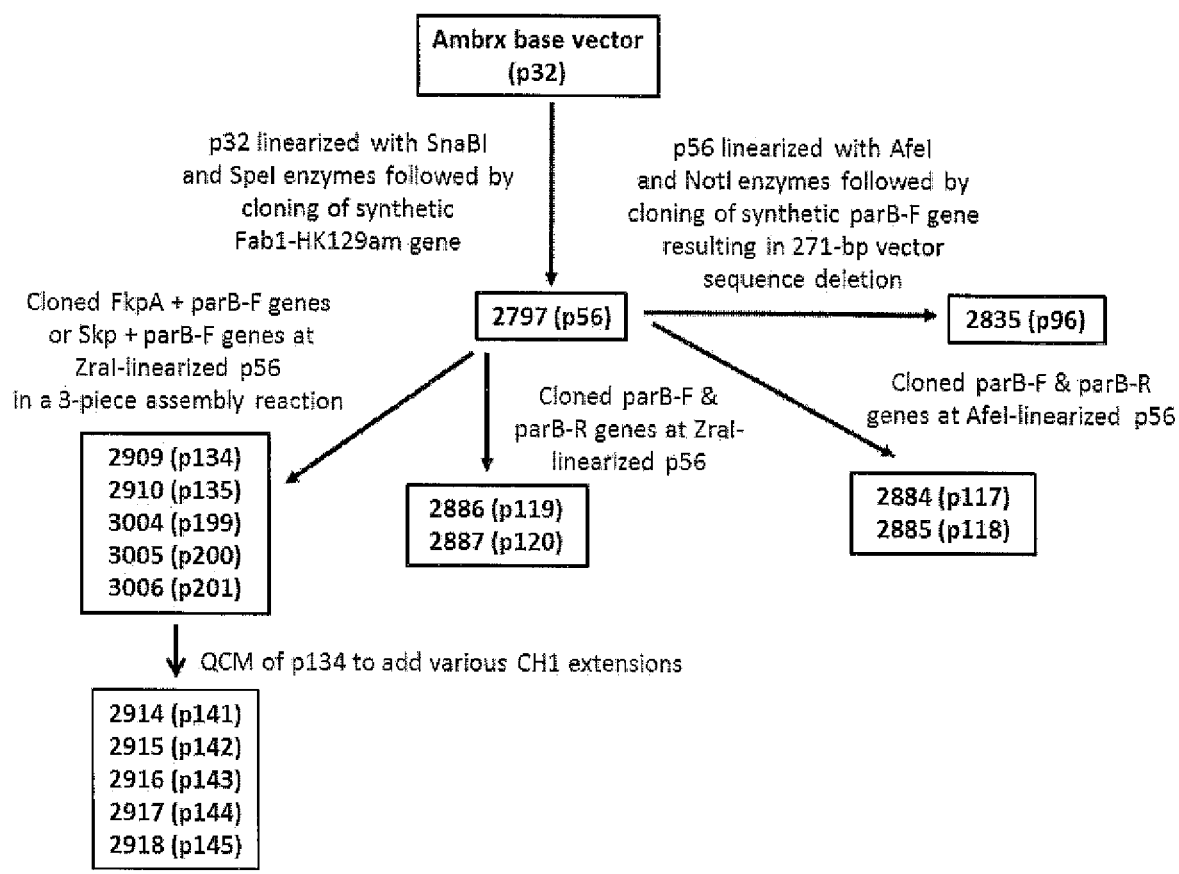
FIG. 2. General scheme for the construction of expression plasmids and their corresponding production strains.

General scheme of expression vector and corresponding production strain construction: FIG. 2 shows the general scheme of expression vector and their corresponding production strain construction. Table 2 describes all expression vectors and their corresponding strains that were used in this study. Briefly, an expression vector was initially constructed either by Gibson Assembly method or by QuikChange mutagenesis protocol in E. coli NEB5α (New England Biolabs, MA) cloning strain as described above. The sequence-verified expression vector DNA was then transformed into platform production host W3110 or W3110B60 strains (Table 1) resulting in corresponding production strains (Table 2) as described herein.

TABLE 2

Production Strains and Corresponding Expression Plasmids

| Production strain | Host strain | Plasmid | Plasmid parameters |
|---|---|---|---|
| 2797 | W3110B60 | p56 | Parent plasmid/stiain with HK129-pAcF site |
| 2835 | W3110B60 | p96 | parB-F cloned between AfeI & NotI sites; deletes Δ271 bp plasmid sequence |
| 2884 | W3110B60 | p117 | parB-F cloned at AfeI site; no plasmid sequence deletion |
| 2885 | W3110B60 | p118 | parB-R cloned at AfeI site; no plasmid sequence deletion |
| 2886 | W3110B60 | p119 | parB-F cloned at ZraI site; no plasmid sequence deletion |
| 2887 | W3110B60 | p120 | parB-R cloned at ZraI site; no plasmid sequence deletion |
| 2909 | W3110B60 | p134 | Both parB-F and FkpA-F chaperone cloned at ZraI site; no plasmid sequence deletion |
| 2910 | W3110B60 | p135 | Both parB-F and Skp-F chaperone cloned at ZraI site; no plasmid sequence deletion |
| 2914 | W3110B60 | p141 | CH1-D extension (1-aa) |
| 2915 | W3110B60 | p142 | CH1-DK extension (2-aa) |
| 2916 | W3110B60 | p143 | CH1-DKTH extension (4-aa) |
| 2917 | W3110B60 | p144 | CH1-DKTHT extension (5-aa) |
| 2918 | W3110B60 | p145 | CH1-DICTHL extension (5-aa with T > L mutation) |
| 3004 | W3110B60 | p199 | Both parB-F and FkpA-R chaperone cloned at ZraI site; no plasmid sequence deletion |
| 3005 | W3110B60 | P200 | Both parB-F and FkpA-F chaperone cloned at ZraI site; no plasmid sequence deletion |
| 3006 | W3110B60 | P201 | Both parB-F and FkpA-R chaperone cloned at ZraI site; no plasmid sequence deletion |

Example 8: Engineered 2797 Strain with Plasmid p56

Figure 3:
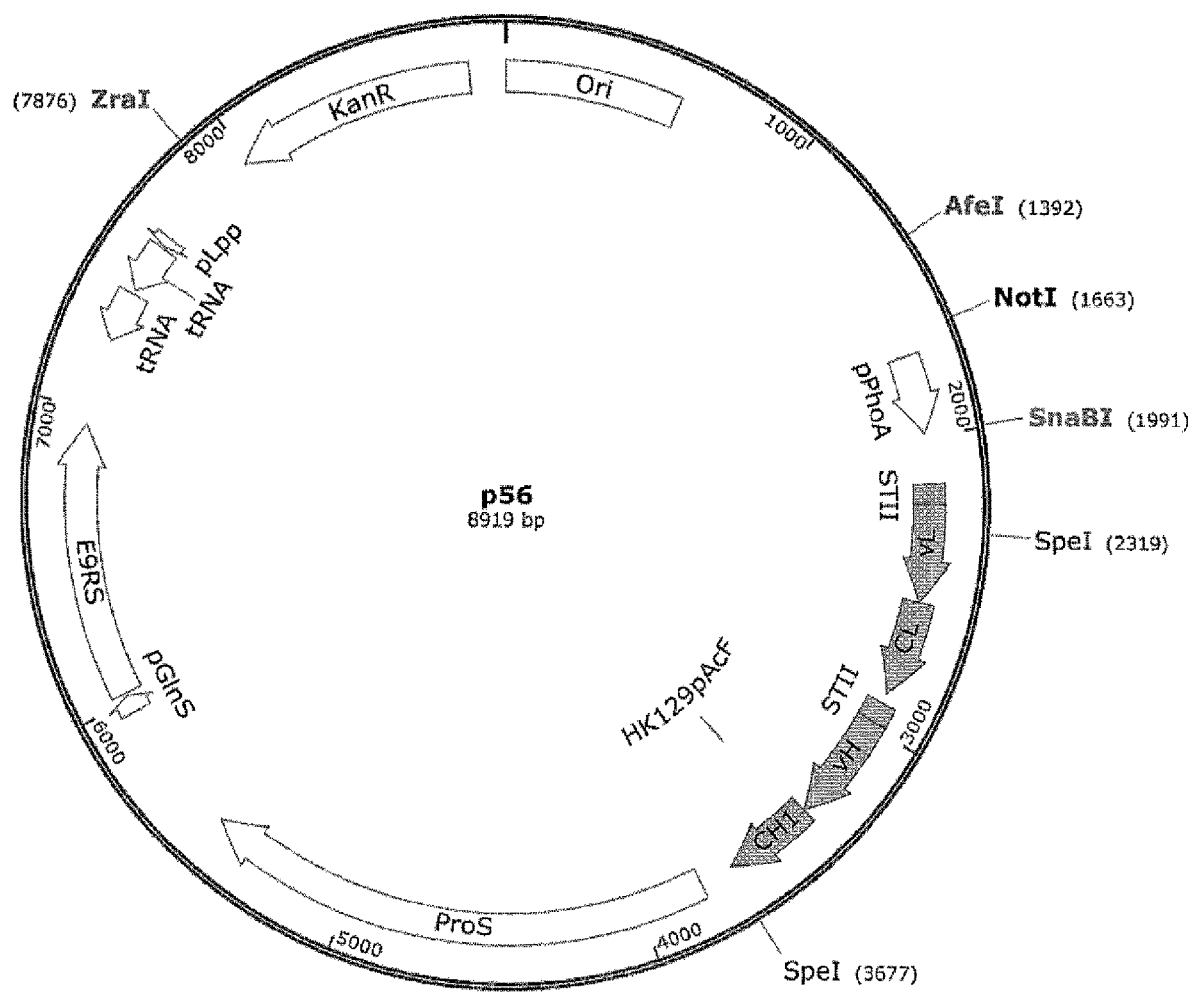
FIG. 3. Plasmid p56 circular map illustrating names, locations and transcriptional directions of various expression elements.

FIG. 3 shows the map of expression plasmid p56. In designing and engineering this plasmid, an orthogonal system with E9 RS synthetase and tRNA cluster contained within the plasmid was utilized, (See, for example, U.S. Patent Publication Nos.: 2003010885, 20050009049, 20050208536, 20060233744). Also utilized in designing and engineering of plasmids of the invention was the overexpression of E. coli proline synthetase, ProS, protein into proprietary plasmid to prevent proline mis-incorporation as well as to complement a temperature-sensitive proS mutation within the chromosome of proprietary platform production host W3110B60 strain to assure plasmid maintenance (described in, for example, Javahishvili, T. et. al., ACS Chem. Biol., 9, 87, 2014).

A synthetic gene for humanized anti-CD3 Fab sequence with Amber TAG stop codon at heavy chain amino acid position HK129 with flanking SnaBI and SpeI restriction enzyme sites was engineered (FIG. 1). The engineered Fab gene was cloned into a proprietary E. coli expression vector using Gibson Assembly kit (New England Biolabs, MA). After sequence verification, plasmid was transformed into the E. coli production host W3110B60 strain and an isolated single colony purified to make glycerol vials. These glycerol vials served as the 2797 production clones for E. coli fermentation of Fab molecule. The DNA and amino acid sequences of both the heavy and light chains of this Fab are shown as SEQ. ID, Nos.: 1 through 11 in Table 3 below.

TABLE 3

Amino Acid and DNA Sequences of Anti-CD3 Fab-HK129am Expression Cassette

| SEQ. ID. NO. | Name | Type | Sequence |
|---|---|---|---|
| 1 | STII (23aa) | Protein | MKKNIAFLLASMFVFSIATNAYA |
| 2 | vL (110aa) | Protein | QAVVTQEPSLTVSPGGTVTLTCRSSTGAVTTSN YANWVQQKPGQAPRGLIGGTNKRAPGTPARFS GSLLGGKAALTLSGAQPEDEAEYYCALWYSNL WVFGGGTKLTVLG |
| 3 | CL (107aa) | Protein | RTVAAPSVFIFPPSDEQLKSGTASVVCLLNNFYP REAKVQWKVDNALQSGNSQESVTEQDSKDST YSLSSTLTLSKADYEKHKVYACEVTHQGLSSP VTKSFNRGEC |
| 4 | vH (125aa) | Protein | EVQLVESGGGLVQPGGSLRLSCAASGFTFNTY AMNWVRQAPGKGLEWVARIRSKYNNYATYY ADSVKDRFTISRDDSKNILYLQMNSLKTEDTAV YYCVRHGNFGNSYVSWFAYWGQGTLVTVSS |

TABLE 3 -continued

Amino Acid and DNA Sequences of Anti-CD3 Fab-HK129am Expression Cassette

| SEQ. ID. NO. | Name | Type | Sequence |
|---|---|---|---|
| 5 | CH1 (103aa) X indicates pAcF insertion | Protein | ASTKGPSVFPLAPSSXSTSGGTAALGCLVKDYF PEPVTVSWNSGALTSGVHTFPAVLQSSGLYSLS SVVTVPSSSLGTQTYICNVNHKPSNTKVDKKVE PKSC |
| 6 | STII (69 bp) | DNA | ATGAAAAAGAATATCGCATTTCTTCTTGCATC TATGTTCGTTTTTTCTATTGCTACAAACGCGT ACGCT |
| 7 | vL (330 bp) | DNA | CAGGCTGTGGTGACTCAGGAGCCCTCACTGA CTGTGTCCCCAGGAGGGACAGTCACTCTCAC CTGTCGCTCCAGCACTGGAGCTGTCACCACT AGTAATTATGCCAACTGGGTCCAGCAGAAGC CTGGCCAAGCCCCCAGGGGACTGATTGGTGG GACAAACAAGAGAGCTCCCGGGACACCTGCC CGGTTCTCAGGCTCCCTCCTTGGGGGCAAAG CTGCCCTGACCCTTTCGGGTGCGCAGCCTGA GGATGAGGCTGAGTATTACTGCGCTCTCTGG TATAGTAATCTGTGGGTGTTCGGCGGAGGGA CCAAGTTGACCGTCCTCGGA |
| 8 | CL (321 bp) | DNA | CGTACGGTGGCTGCACCATCTGTCTTCATCTT CCCGCCATCTGATGAGCAGTTGAAATCTGGA ACTGCCTCTGTTGTGTGCCTGCTGAATAACTT CTATCCCAGAGAGGCCAAAGTACAGTGGAAG GTGGATAACGCCCTCCAATCGGGTAACTCCC AGGAGAGTGTCACAGAGCAGGACAGCAAGG ACAGCACCTACAGCCTCAGCAGCACCCTGAC GCTGAGCAAAGCAGACTACGAGAAACACAA AGTCTACGCCTGCGAAGTCACCCATCAGGGC CTGAGCTCGCCCGTCACAAAGAGCTTCAACA GGGGAGAGTGT |
| 9 | Spacer (32 bp) | DNA | TCTGGGGATAAGAATTCGGTTGAGGTGATTT T |
| 10 | vH (375 bp) | DNA | GAGGTGCAGCTGGTGGAGTCTGGGGGAGGCT TGGTCCAGCCTGGAGGGTCCCTGAGACTCTC CTGTGCAGCCTCTGGATTCACCTTCAATACCT ACGCAATGAACTGGGTCCGCCAGGCTCCAGG GAAGGGGCTGGAGTGGGTTGCTCGTATTAGA AGCAAATATAACAATTACGCCACATATTACG CCGATTCTGTGAAAGACAGATTCACCATCTC AAGAGATGATTCAAAGAACATTCTGTATCTG CAAATGAACAGCCTGAAAACCGAGGACACG GCCGTGTATTACTGTGTTAGACATGGGAATTT CGGCAACTCTTATGTCAGTTGGTTTGCCTACT GGGGCCAAGGTACCCTGGTCACCGTCTCGAG T |
| 11 | CH1 (309 bp) TAG indicates amber site | DNA | GCTAGCACCAAGGGCCCATCGGTCTTCCCCC TGGCACCCTCCTCCTAGAGCACCTCTGGGGG CACAGCGGCCCTGGGCTGCCTGGTCAAGGAC TACTTCCCCGAACCGGTGACGGTGTCGTGGA ACTCAGGCGCCCTGACCAGCGGCGTGCACAC CTTCCCGGCTGTCCTACAGTCCTCAGGACTCT ACTCCCTCAGCAGCGTGGTGACCGTGCCCTC CAGCAGCTTGGGCACCCAGACCTACATCTGC AACGTGAATCACAAGCCCAGCAACACCAAG GTGGACAAGAAAGTTGAGCCCAAATCTTGT |

Figure 4:
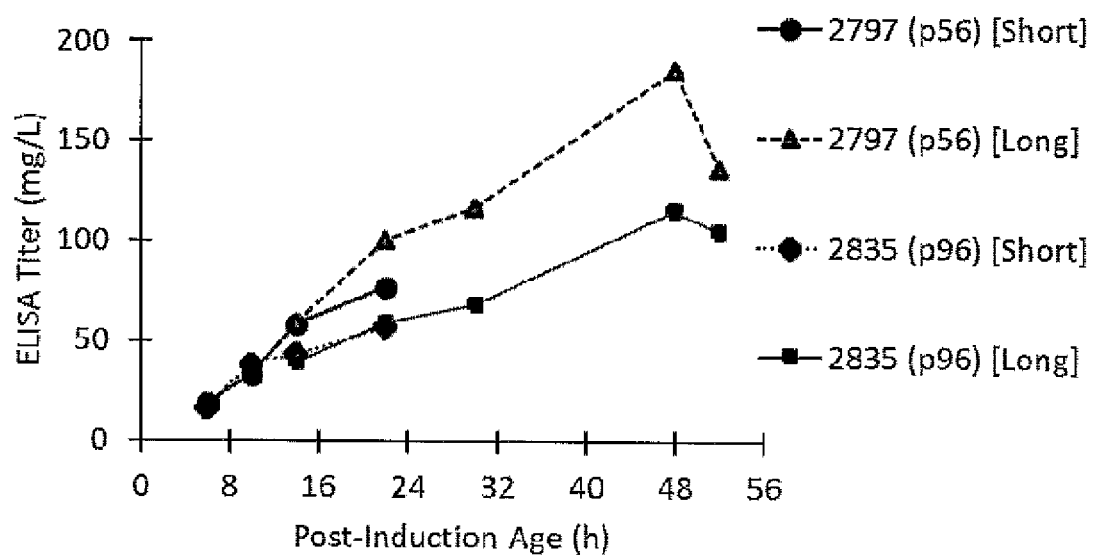
FIG. 4. Fermentation titers of production strain 2835 harboring plasmid p96 along with parent strain 2797 harboring parent plasmid p56. In plasmid p96, the parB locus was cloned in Forward orientation between the AfeI and NotI restriction enzyme sites, thereby deleting a 271-bp nucleotide sequence from the plasmid backbone. Cell pellet titers of production strains 2797 and 2835 are shown.
Figure 5A:
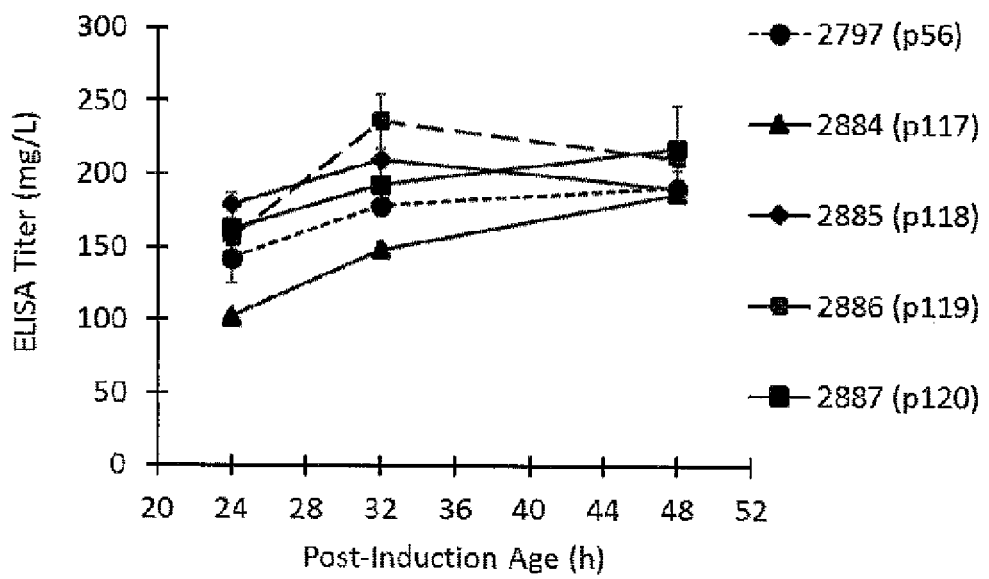
FIGS. 5A-B. Fermentation titers of 4 new parB-containing production strains without any deletion of plasmid backbone sequence. In strains 2884 (p117) and 2885 (p118), parB locus was cloned in either For or Rev orientation, respectively, at Afe1 restriction enzyme site. In strains 2886 (p119) and 2887 (p120), parB locus was cloned in either For or Rev orientation, respectively, at Zra1 restriction enzyme site. Both cell pellet (FIG. 5A) and medium (FIG. 5B) titers are shown.
Figure 5B:
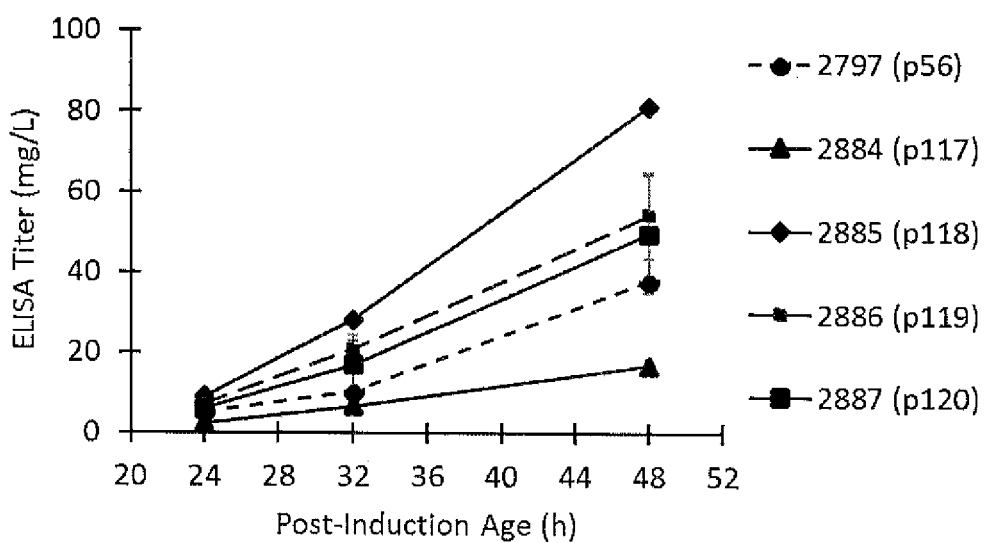

The fermentation titers and plasmid retention of strain 2797 are shown in FIGS. 4, 5A-B and Table 4 below.

TABLE 4

Plasmid Retention of Strain 2797

| Production strain | Fermentation process | Time point (hr) | Plasmid retention (%) | Plasmid parameters (parB status) |
|---|---|---|---|---|
| 2797 | Long | 54 | 1 | No parB |
| 2797 | Long-optimized | 48 | 0-44 | No parB |

Example 9: Engineered Strains with Varied Partition Locus B (parB) Positioning and Orientation Production host cell line W3110B60, used to generate strain 2797, contains a mutation in the genomic proS proline synthetase gene (W375R). This mutation makes the genomic ProS protein inactive above 34° C., thus creating a temperature-sensitive W3110B60 cell line with growth inhibited at 37° C. In addition to the anti-CD3 Fab gene of interest (GOI), the p56 plasmid in 2797 strain also contains the *E. coli* proS gene for expression of the wild-type *E. coli* ProS protein. This enables growth and provides a selective pressure to maintain the GOI plasmid at 37° C. It may not, however, provide an advantage for plasmid maintenance when production temperature is lower than 34° C. The kanR gene for kanamycin resistance is also present on p56 plasmid (FIG. 3), providing a selective pressure for plasmid maintenance when the antibiotic kanamycin is added to the medium. Even with both of these components, poor plasmid retention was observed in 2797 cells collected at various time points during fermentation (Table 4).

To ensure robust plasmid maintenance during the entire fermentation run, irrespective of Fab production temperature or any other process limitations, various strategies were investigated. One strategy was to ensure proper plasmid segregation during bacterial cell division such that each daughter cell inherits the same plasmid. It has been shown in the literature that in some bacterial plasmid segregation systems, specific genes known as plasmid partition locus (par) ensure this by killing the daughter cells which had lost the plasmid during cell division (Ebersbach G. & Gerdes K., Annu. Rev. Genet. 39, 453, 2005). Additionally, other findings in the literature have demonstrated that incorporation of a 580-bp minimal partition B parB (hok/sok) locus (SEQ. ID. NO:12), originally from *E. coli* plasmid R1, on plasmids can improve their maintenance and stability in many bacteria including *E. coli* (Gerdes K., Nature Biotech. 6, 1402, 1988; Gerdes K. et. al., Mol. Microbiol. 4, 1807, 1990; Gerdes K. and Neilsen Al, J. Mol. Biol. 226, 637, 1992).

Therefore, the inventors sought to clone a synthetic 580-bp parB locus gene (DNA2.0, Menlo Park, CA) with Forward (F) transcriptional direction of its host killing (hok) gene (SEQ. ID. NO:13) and amino acid (SEQ. ID. NO:14) with respect to the downstream Fab gene transcriptional direction between the Afe1 and Not1 restriction enzyme sites in plasmid p56. This strategy generated a synthetic engineered plasmid, p96, having a 271-bp deletion in plasmid backbone just upstream of the phoA promoter region. All other coding regions (CDSs) and their transcriptional directions including the Fab gene, kanR, and proS genes remain unchanged. Plasmid p96 was then transformed into a standard production host W3110B60 strain as described in above Examples, to obtain production strain 2835.

TABLE 5

DNA and Protein Sequences of parB locus, FkpA and Skp Chaperones

| SEQ. ID. No. | Name | Type | Sequence |
|---|---|---|---|
| 12 | parB (580-bp) | DNA | AACAAACTCCGGGAGGCAGCGTGATGCGGCAACAATC ACACGGATTTCCCGTGAACGGTCTGAATGAGCGGATT ATTTTCAGGGAAAGTGAGTGTGGTCAGCGTGCAGGTA TATGGGCTATGATGTGCCCGGCGCTTGAGGCTTTCTGC CTCATGACGTGAAGGTGGTTTGTTGCCGTGTTGTGTGG CAGAAAGAAGATAGCCCCGTAGTAAGTTAATTTTCAT TAACCACCACGAGGCATCCCTATGTCTAGTCCACATC AGGATAGCCTCTTACCGCGCTTTGCGCAAGGAGAAGA AGGCCATGAAACTACCACGAAGTTCCCTTGTCTGGTG TGTGTTGATCGTGTGTCTCACACTGTTGATATTCACTT ATCTGACACGAAAATCGCTGTGCGAGATTCGTTACAG AGACGGACACAGGGAGGTGGCGGCTTTCATGGCTTAC GAATCCGGTAAGTAGCAACCTGGAGGCGGGCGCAGG CCCGCCTTTTCAGGACTGATGCTGGTCTGACTACTGAA GCGCCTTTATAAAGGGGCTGCTGGTTCGCCGGTAGCC CCTTTCTCCTTGCTGATGTTGT |
| 13 | hok (156-bp) | DNA | ATGAAACTACCACGAAGTTCCCTTGTCTGGTGTGTGTT GATCGTGTGTCTCACACTGTTGATATTCACTTATCTGA CACGAAAATCGCTGTGCGAGATTCGTTACAGAGACGG ACACAGGGAGGTGGCGGCTTTCATGGCTTACGAATCC GGTAAG |
| 14 | Hok (52-aa) | Protein | MKLPRSSLVWCVLIVCLTLLIFTYLTRKSLCEIRYRDGHR EVAAFMAYESGK |

TABLE 5 -continued

DNA and Protein Sequences of parB locus, FkpA and Skp Chaperones

| SEQ. ID. No. | Name | Type | Sequence |
|---|---|---|---|
| 15 | fkpA (1199-bp) | DNA | GATTCACCTCTTTTGTCGAATGGTCGCCGCGGATTCTA CTTAACTTTGCTGCCCGAGACAGCACTCATTTCGCGGT CATCGAAACTAATTTAAACAAAAAGAGTCTGAAAATA GATGATAATAGGGCGTGTCTGTATGTAGATTTGTTCGA CAACGCTTTATAGTACCCTTCTGATAATAGTTAACCCT GGGGTGAGATGCCCCGATCCTGGAGATATGGATGAAA TCACTGTTTAAAGTAACGCTGCTGGCGACCACAATGG CCGTTGCCCTGCATGCACCAATCACTTTTGCTGCTGAA GCTGCAAAACCTGCTACAGCTGCTGACAGCAAAGCAG CGTTCAAAAATGACGATCAGAAATCAGCTTATGCACT GGGTGCCTCGCTGGGTCGTTACATGGAAAACTCTCTA AAAGAACAAGAAAAACTGGGCATCAAACTGGATAAA GATCAGCTGATCGCTGGTGTTCAGGATGCATTTGCTGA TAAGAGCAAACTCTCCGACCAAGAGATCGAACAGACT CTACAAGCATTCGAAGCTCGCGTGAAGTCTTCTGCTCA GGCGAAGATGGAAAAAGACGCGGCTGATAACGAAGC AAAAGGTAAAGAGTACCGCGAGAAATTTGCCAAAGA GAAAGGTGTGAAAACCTCTTCAACTGGTCTGGTTTATC AGGTAGTAGAAGCCGGTAAAGGCGAAGCACCGAAAG ACAGCGATACTGTTGTAGTGAACTACAAAGGTACGCT GATCGACGGTAAAGAGTTCGACAACTCTTACACCCGT GGTGAACCGCTTTCTTTCCGTCTGGACGGTGTTATCCC GGGTTGGACAGAAGGTCTGAAGAACATCAAGAAAGG CGGTAAGATCAAACTGGTTATTCCACCAGAACTGGCT TACGGCAAAGCGGGTGTTCCGGGGATCCCACCGAATT CTACCCTGGTGTTTGACGTAGAGCTGCTGGATGTGAA ACCAGCGCCGAAGGCTGATGCAAAGCCGGAAGCTGAT GCGAAAGCCGCAGATTCTGCTAAAAAATAAGCATTAA GAACCGCCGCCTGACCAGGCGGCGGTTTTTTTATTACA GGCCGGATATAATTAGTGCTGGAAAGCGGAACCTCCG CTGTATTAATTTAGTTACCCGCATCATTAATGAGCCTG CCCTGAAAAGTTAACGACAGGCTCCTGAAAAGGAGTG TTTTTTTC |
| 16 | FkpA (270-aa) | Protein | MKSLFKVTLLATTMAVALHAPITFAAEAAKPATAADSK AAFKNDDQKSAYALGASLGRYMENSLKEQEKLGIKLDK DQUAGVQDAFADKSKLSDQEIEQTLQAFEARVKSSAQA KMEKDAADNEAKGKEYREKFAKEKGVKTSSTGLVYQV VEAGKGEAPKDSDTVVVNYKGTLIDGKEFDNSYTRGEP LSFRLDGVIPGWTEGLKNIKKGGKIKLVIPPELAYGKAG VPGIPPNSTLVFDVELLDVKPAPKADAKPEADAKAADSA KK |
| 17 | skp | DNA | TTTAACATCGGTAAAACCTGGTAAGTGTTCTCCACAA AGGAATGTAGTGGTAGTGTAGCGATGACTTTAGGCGA TCAATATAAGATCGCCGGGCCACGCAAAGAACTGCAC CCTCCGGTGCAAATGGGATGGTAAGGAGTTTATTGTG AAAAAGTGGTTATTAGCTGCAGGTCTCGGTTTAGCAC TGGCAACTTCTGCTCAGGCGGCTGACAAAATTGCAAT CGTCAACATGGGCAGCCTGTTCCAGCAGGTAGCGCAG AAAACCGGTGTTTCTAACACGCTGGAAAATGAGTTCA AAGGCCGTGCCAGCGAACTGCAGCGTATGGAAACCGA TCTGCAGGCTAAAATGAAAAAGCTGCAGTCCATGAAA GCGGGCAGCGATCGCACTAAGCTGGAAAAAGACGTG ATGGCTCAGCGCCAGACTTTTGCTCAGAAAGCGCAGG CTTTTGAGCAGGATCGCGCACGTCGTTCCAACGAAGA ACGCGGCAAACTGGTTACTCGTATCCAGACTGCTGTG AAATCCGTTGCCAACAGCCAGGATATCGATCTGGTTG TTGATGCAAACGCCGTTGCTTACAACAGCAGCGATGT AAAAGACATCACTGCCGACGTACTGAAACAGGTTAAA TAAGTA |
| 18 | Skp (161-aa) | Protein | MKKWLLAAGLGLALATSAQAADKIAIVNMGSLFQQVA QKTGVSNTLENEFKGRASELQRMETDLQAKMKKLQSM KAGSDRTKLEKDVMAQRQTFAQKAQAFEQDRARRSNE ERGKLVTRIQTAVKSVANSQDIDLVVDANAVAYNSSDV KDITADVLKQVK |

Production strains, 2797 and 2835, were then compared in high cell density fermentation processes as described above. FIG. 4 compares the production titer of strains 2797 and 2835 under both short and long fermentation conditions. Table 6 shows the plasmid retention data for these two strains under two different fermentation processes. Typical plasmid retention for strain 2797 varied between 0% and 44% at 48 hour upon long fermentation process optimization to retain the plasmid, with only 1% plasmid retention measured at 54 hours. As expected and shown, incorporation of the parB locus in strain 2835 significantly improved plasmid retention. Both fermentation runs with 2835 strain showed 100% plasmid retention in both processes and at both time points (22 hours and 54 hours; Table 6).

TABLE 6

Plasmid retention of parB-containing strains and parent strain 2797

| Production strain | Fermentation process | Time point (hr) | Plasmid retention (%) | Plasmid parameters (parB status) |
|---|---|---|---|---|
| 2797 | Long | 54 | 1 | No parB |
| 2797 | Long-optimized | 48 | 0-44 | No parB |
| 2835 | Short | 22 | 100 | parB-F at AfeI + NotI site; 271-bp plasmid sequence deletion |
| 2835 | Long | 52 | 100 | parB-F at AfeI + NotI site; 271-bp plasmid sequence deletion |
| 2884 | Long | 48 | 100 | parB-F at AfeI site; no plasmid sequence deletion |
| 2885 | Long | 48 | 100 | parB-R at AfeI site; no plasmid sequence deletion |
| 2886 | Long | 48 | 100 | parB-F at ZraI site; no plasmid sequence deletion |
| 2887 | Long | 48 | 100 | parB-R at ZraI site; no plasmid sequence deletion |

Despite improved plasmid maintenance, the cell pellet titers were about 40% lower with the 2835 cell line for both short and long fermentation processes (FIG. 4). This was unexpected since improved plasmid retention theoretically should have, at least, maintained the same productivity, if not improved at all. Titer improvements were later observed with insertion of the parB locus without any deletion of plasmid backbone sequence which is described below.

Example 10: Engineering of ParB-Containing Vectors and Strains without Plasmid Sequence Deletion As described above, insertion of the parB locus between the AfeI and NotI restriction enzyme sites in Forward (F) orientation resulted in improved plasmid retention (100%), as expected from the literature. However, unexpectedly, it also lowered intact Fab titers by about 40% in the cell pellet. To recover this production loss, 4 new expression plasmids (p117, p118, p119 and to p120; Table 2) without any deletion of the plasmid backbone sequence were engineered. AfeI and ZraI unique restriction enzyme sites within the plasmid backbone were utilized. The same parB locus was cloned at both locations either in forward (F) or in reverse (R) orientation with respect to the Fab CDS. This strategy resulted in 4 new production strains, 2884, 2885, 2886 and 2887, (Table 2), which were then compared in high cell density fermentation with the original strain 2797 for both plasmid retention and production titer (FIGS. 5A-B and Table 6).

The new production cell lines were 2884 (anti-CD3 Fab, parB-AfeI-F), 2885 (anti-CD3 Fab, parB-AfeI-R), 2886 (anti-CD3 Fab, parB-ZraI-F), and 2887 (anti-CD3 Fab, parB-ZraI-R) where AfeI or ZraI indicates the restriction enzyme site where the parB locus was cloned, and F (forward) indicates that transcription of hok gene is in the same orientation as Fab CDS, where R (reverse) indicates that transcription of hok gene is in the reverse orientation compared to Fab CDS. These production cell lines were compared to 2797 (anti-CD3 Fab) without the parB locus.

As expected, all 4 new parB cell lines showed 100% plasmid retention 48 hours post-induction (Table 6). This demonstrates a significant improvement over 2797 without the parB locus, where plasmid retention at the end of fermentation varied from as low as 0% to the highest measured at 44%, depending on the fermentation process used (see Table 6 and above Examples). Surprisingly, the location and the orientation of the parB locus within the plasmid had significant effect on anti-CD3 Fab titer. Three strains (strain 2885, 2886, and 2887) out of 4 new strains showed significantly improved cell pellet (FIG. 5A) and media (FIG. 5B) titers over 2797 control strain. In addition to the change in location and orientation of the parB locus from 2835 described above, in strains 2884 to 2887, parB was cloned with avoidance of deleting any portion of the plasmid sequence. In a separate study, it was observed that deleting parts of the plasmid sequence upstream of the phoA promoter region had a negative impact on Fab titers (data not shown). By relocating parB away from this region and leaving this sequence intact likely supports the increased Fab titers observed with a majority of these constructs.

Only strain 2884 had both cell pellet and media titers lower than the control strain 2797 (FIGS. 5A-5B). The only difference between strains 2884 and 2835, described herein, is the deletion of 271-bp plasmid sequence between the AfeI and NotI restriction enzyme sites with same parB-F orientation. Therefore, as plasmid sequence deletion, or lack thereof, at this location resulted in lower Fab titer (strain 2835 compare with 2884), it was concluded that parB orientation is more important than location for increasing titer given strain 2885 with parB-R orientation improved titer.

Figure 6:
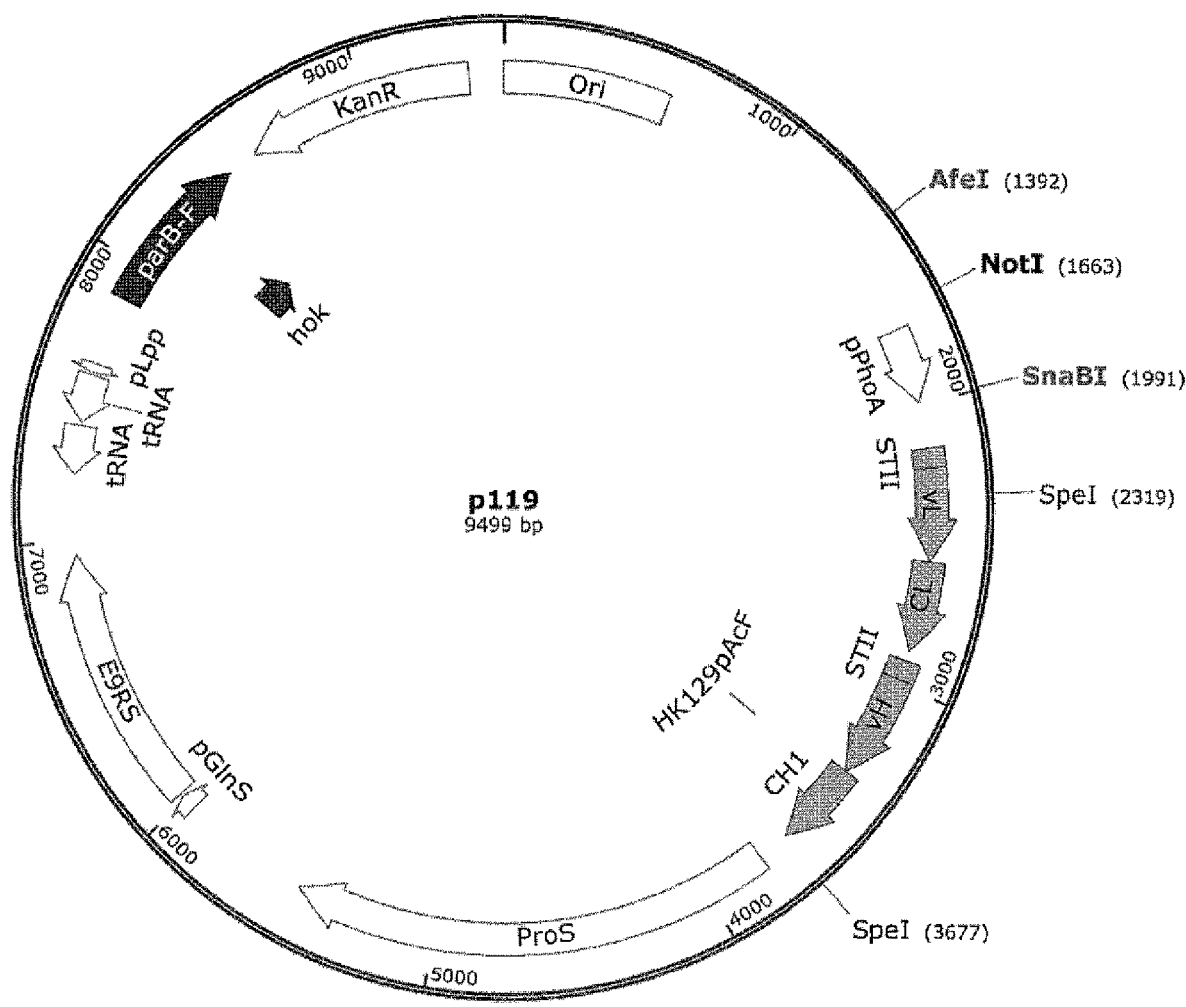
FIG. 6. Map of plasmid p119 contained in strain 2886 shown with the optimal location and orientation of parB locus.

Further studies were conducted using strains 2886 and 2887, where parB is located further away from the phoA promoter region, in an effort to determine the best strain for optimization of the expression process. Strain 2886 was chosen as it gave the highest titer, with 236 mg/L measured 32 hours post-induction (average of n=3 fermentations; data not shown). Plasmid p119 map contained in strain 2886 is shown in FIG. 6 with the optimal location and orientation of the cloned parB locus.

Example 11: Design and Effects of Periplasmic Chaperones in a Compatible Two-Plasmid Expression System To determine the involvement of molecular chaperones in optimizing or increasing protein titer in *E. coli*, two well-known bi-functional periplasmic chaperones, FkpA and Skp, having peptidyl prolyl isomerase activities were analyzed.

Figure 7:
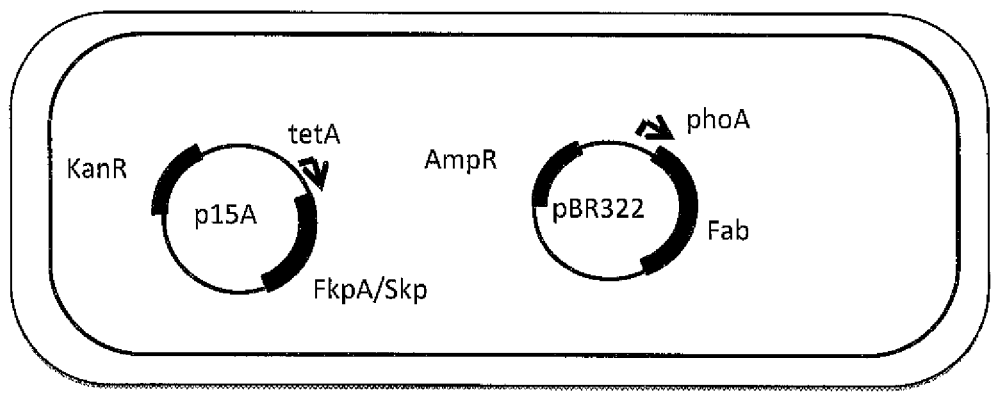
FIGS. 7A-B. Schematic of a compatible two plasmid (FIG. 7A) versus single plasmid (FIG. 7B) expression system for testing the effects of periplasmic chaperone expression. Fab vector contains AmpR marker and chaperone vector contains KanR marker in the two-plasmid system. For the single plasmid system, chaperone gene is cloned into standard Fab vector with KanR marker.
Figure 7:
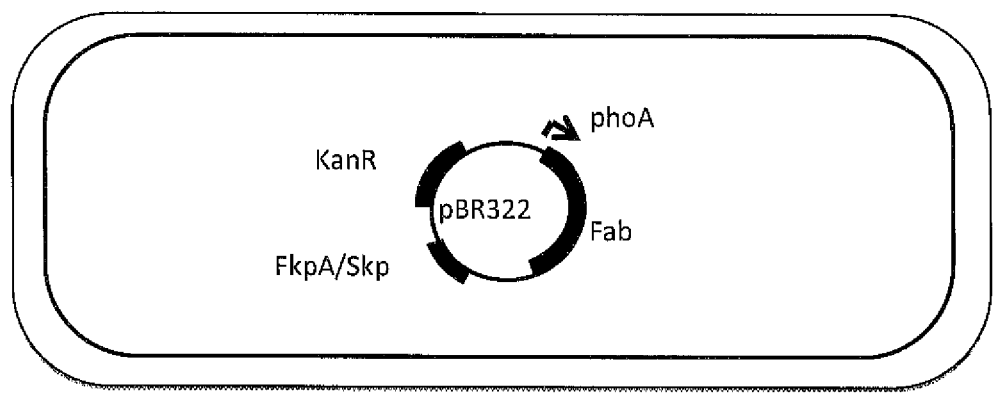

Toward this end, two compatible plasmids were constructed with p15A origin of replication (10-15 copy number/cell) by cloning FkpA or Skp gene. These kanamycin-resistance (KanR) plasmids were co-transformed with anti-CD3 Fab expression plasmid having ampicillin-resistance (AmpR) with pBR322 origin of replication (30-50 copy number/cell) to test the effects of periplasmic chaperone co-expression (FIG. 7A).

For this study, wild-type W3110 expression host strain (Table 1) was utilized given that the standard production host, W3110B60, strain has a KanR marker inserted in the chromosome. All 3 proprietary cell lines in this study were co-transformed with two plasmids as illustrated in FIG. 7A. Plasmid 1 contains anti-CD3 Fab+ampR+parB (with para cloned with 271-bp deletion between Afe1 and Not1 restriction enzyme sites) in all 3 production strains. For the periplasmic chaperone strains 2840 and 2841, plasmid 2 contains chaperones FkpA and Skp, respectively, behind the inducible tetracycline promoter (pTetA) with kanamycin resistance (kanR) marker where fkpA and skp genes are induced by the addition of 50 parts per billion (ppb) of tetracycline in the medium (FIG. 7A). For the control strain 2939, plasmid 2 contains kanamycin resistance (kanR) marker but no chaperone. The DNA and protein sequences of FkpA and Skp chaperones are included as SEQ ID NOs: 15 to 18 in Table 5.

Figure 8:
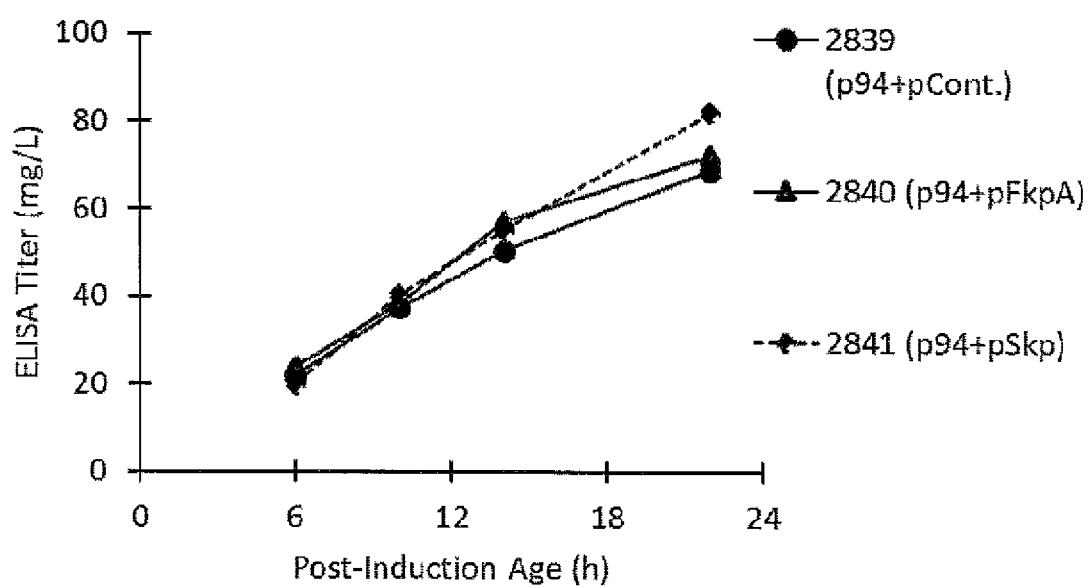
FIG. 8. Fermentation titers of two periplasmic chaperone expressing strains, strains 2840 and 2841, along with a control strain 2839 without any chaperone gene in a compatible two-plasmid expression system.

All fermentations were conducted using the short fermentation process as mentioned in the above Examples and shown in FIG. 4. For all 3 strains, 50 mg/mL carbenicillin and 50 µg/mL kanamycin were added to the medium to maintain both plasmids. For strains 2840 and 2841 (Table 7), 2 mL of 50 µg/mL tetracycline (50 ng/mL final concentration) was added with pAcF at phosphate ($PO_4$) depletion to induce expression of chaperones. Cell pellet ELISA titers are shown in FIG. 8. Contrary to expectation, there was no increase in pellet titer observed for co-expression of periplasmic chaperones FkpA and Skp. There was no leakage to the media for any of these strains either (data not shown).

It is noted that the lack of Fab expression improvement observed may be attributed to the expression of periplasmic chaperones being un-coupled from their natural E. coli promoter since they were artificially driven by the inducible tetracycline promoter (pTetA) as disclosed herein. In E. coli, the expression of FkpA and Skp genes are driven by an alternative sigma factor E (sigma E) which is involved in various periplasmic stress sensing including mis-folded/unfolded protein stress (Merdanovic M. et. al., Annu. Rev. Microbial. 2011, 65, 149). This allows, expression of these chaperones to be induced when necessary i.e., when cells sense mis-folded/unfolded protein stress. Based on this rationale, the inventors sought to determine the influence of the natural promoter system, disclosed below.

Example 12: Design and Effects of Periplasmic Chaperones in a Single Plasmid Expression System Given that no improvement of Fab titer was observed in a compatible two-plasmid system, as disclosed above, a single plasmid system was examined. In this system the chaperone genes, FkpA and Skp, were cloned behind their native promoters into the same plasmid as anti-CD3 Fab with parB-ZraI-F as in 2886 strain (see FIG. 7B).

The cell lines used in this study were 2886 (anti-CD3 Fab, parB-ZraI-F) as a control, 2909 (anti-CD3 Fab, parB-ZraI-F, AA) for FkpA co-expression, and 2910 (anti-CD3 Fab, parB-ZraI-F, skp) for Skp co-expression. Plasmids p134 and p135 (Table 2) contain the FkpA and Skp chaperones, respectively, cloned with their native promoter sequences in Forward (F) orientation with respect to parB locus and Fab orientation. Thus, this strategy tied expression to the cellular physiology (i.e., misfolded/unfolded protein stress) rather than the uncoupled tetracycline-inducible expression as in the two-plasmid system (see FIG. 10, p134 plasmid map).

Figure 9A:
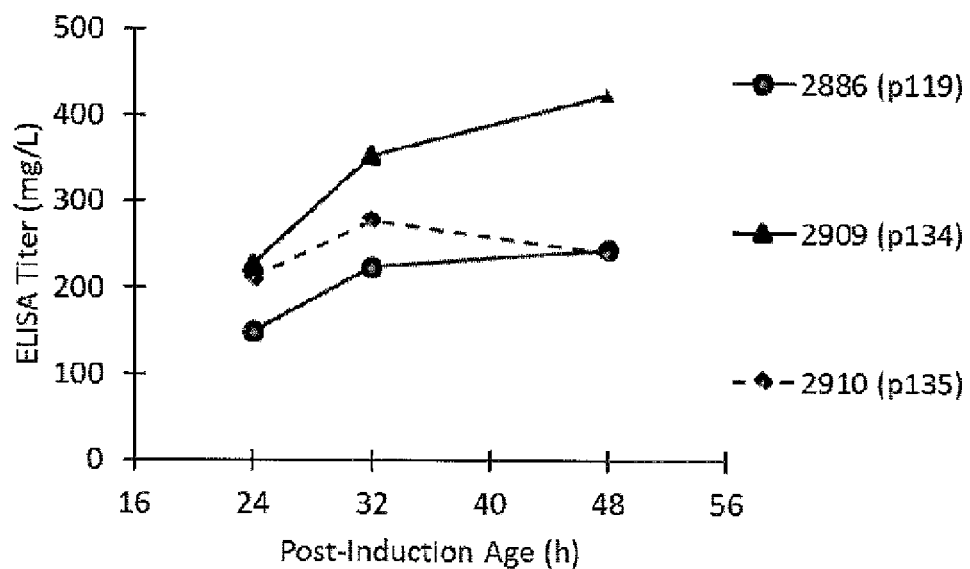
FIGS. 9A-B. Fermentation titers of two periplasmic chaperone expressing strains, strain 2909 (p134) and strain 2910 (p135), along with the parent strain 2886 (p119) in a single plasmid expression system. Both cell pellet (FIG. 9A) and medium (FIG. 9B) titers are shown.
Figure 9B:
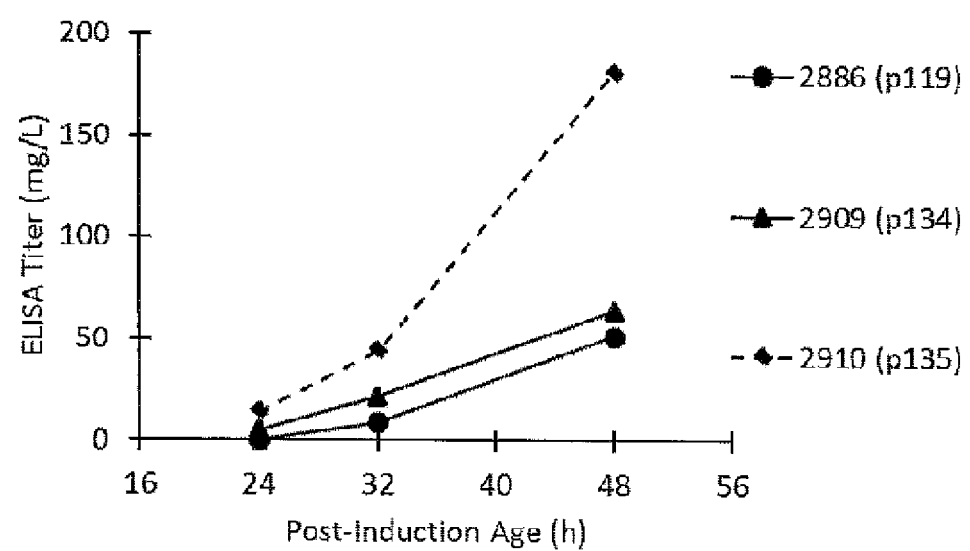

Co-expression of either periplasmic chaperone FkpA or Skp in this manner increased total Fab production significantly over 2886 titers (FIGS. 9A-9B). Skp co-expression, however, resulted in significant Fab leakage into the medium, and 2910 cell pellet titers at 48 hours post-induction were not any higher than 2886. With FkpA co-expression, the majority of the Fab was retained in the cell pellet. 424 mg/L ELISA titer was measured for 2909, versus 245 mg/L for 2886 ELISA titers measured the same day. Thus, it was clear that the manner in which chaperones are co-expressed for recombinant protein production is very important. From this data, 2909 with the FkpA chaperone was chosen for further development.

Figure 10:
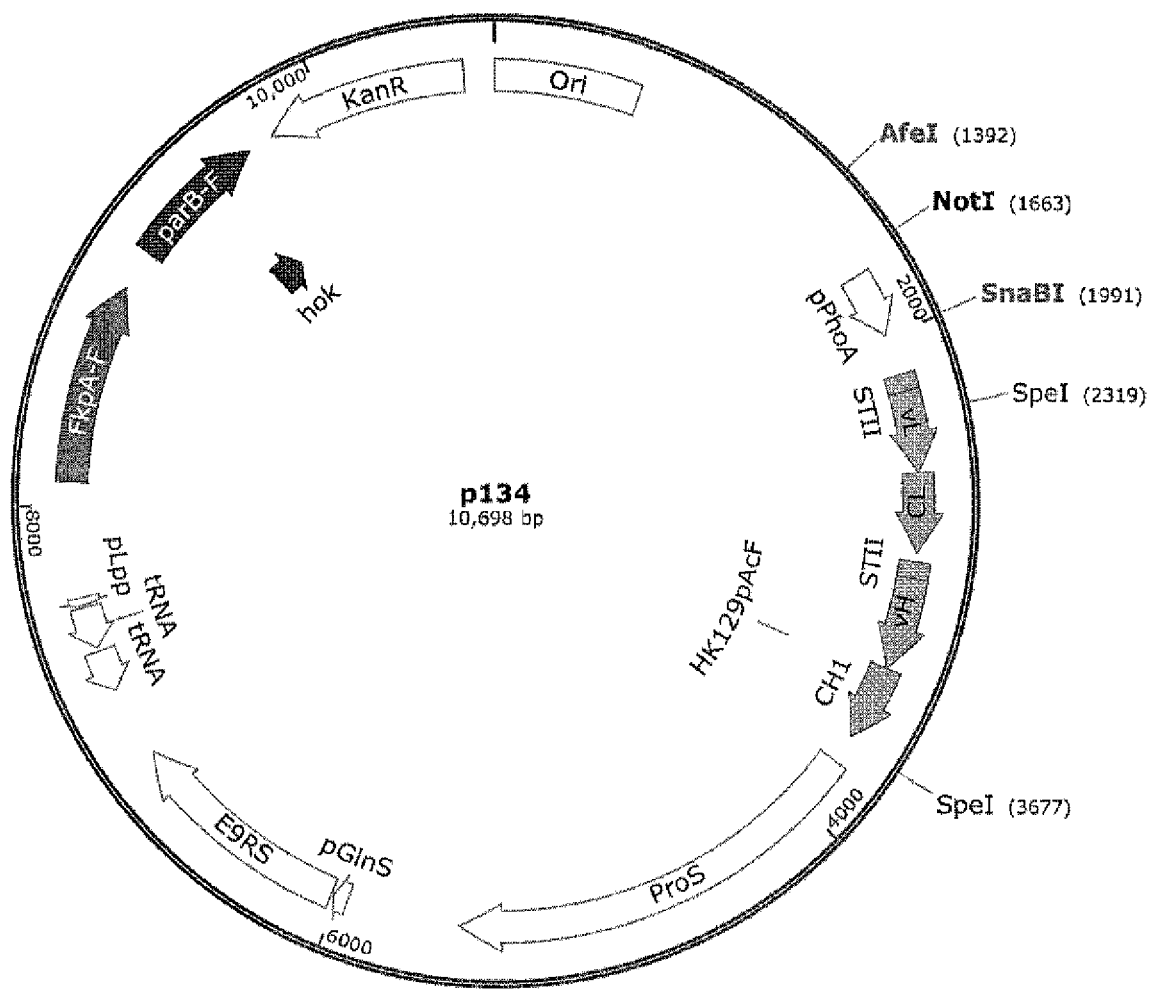
FIG. 10. Map of plasmid p134 contained in strain 2909 shown with the location and orientation of FkpA chaperone and parB locus.

Example 13: Optimization of FkpA Chaperone Location and Orientation with Respect to Fab and ParB Locus within the Plasmid As disclosed above in strain 2909, FkpA chaperone was cloned in Forward orientation behind the parB locus in the single plasmid expression system (FIG. 10). The same FkpA chaperone gene, when expressed from a separate plasmid as in the two-plasmid expression system in strain 2840 (see FIGS. 7A-B and Figure-8), did not improve Fab titer underscoring the importance of aligning helper chaperone expression with cellular physiology.

Based on the data obtained on the effects of location and orientation of parB locus with respect to Fab orientation in the expression plasmid, as described in the above Examples, the inventors speculated that the location and orientation of the chaperone genes including FkpA might also impact Fab titer. To examine this aspect of the invention, plasmids were designed and engineered by cloning the fkpA gene in front

TABLE 7

Production Strains and Corresponding Expression Plasmids in a Compatible Two-plasmid System

| Production strain | Host strain | Fab1 plasmid | Fab AbR | Chaperone plasmid | Chaperone AbR | Comments |
|---|---|---|---|---|---|---|
| 2839 | W3110 | p94 | Amp | No chaperone | Kan | Parent strain for comparison |
| 2840 | W3110 | p94 | Amp | FkpA | Kan | FkpA chaperone strain |
| 2841 | W3110 | p94 | Amp | Skp | Kan | Skp chaperone strain | or in back of the parB locus in both For and Rev orientations. This strategy allowed for assessment of the effect of chaperone gene co-expression on recombinant protein production at three different levels: 1) promoter effect, 2) position effect, and 3) orientation effect.

Figure 11:
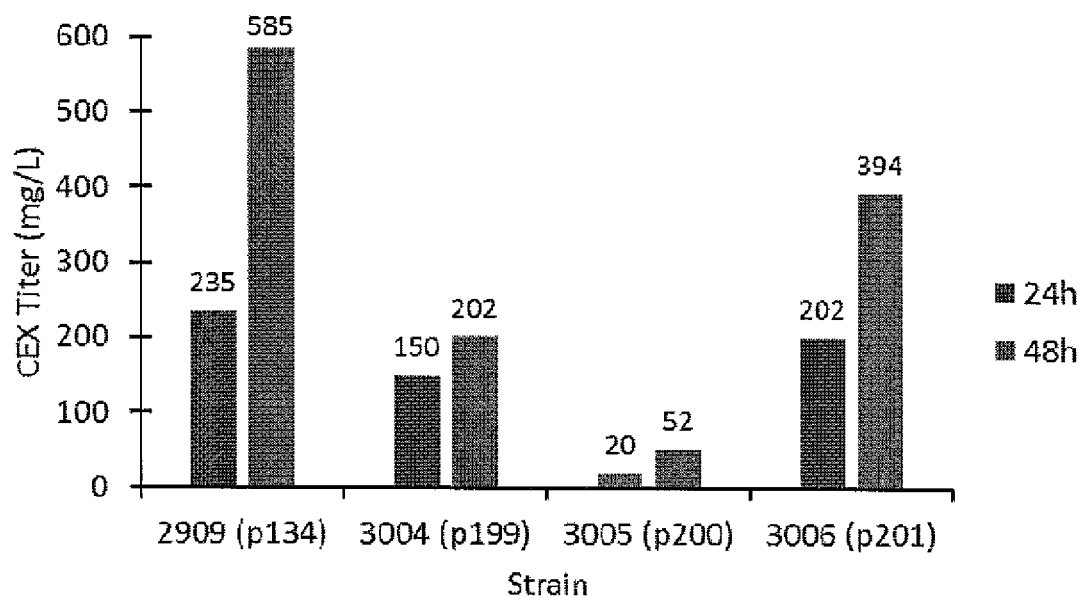
FIG. 11. Cell pellet titers of various strains expressing helper factors parB locus and FkpA chaperone varying in their position and orientation in the plasmid.

Toward this end, three new plasmids (p199, p200 and p201) were designed and constructed by varying the FkpA chaperone position and orientation with respect to parB-F position as shown in Table 8. Three (3) new production strains (strains 3004, 3005 and 3006) harboring these new plasmids were tested for their effects on Fab expression titer. As shown in FIG. 11, position and orientation of FkpA chaperone with respect to parB-F orientation significantly affected the Fab titer. No leakage of Fab to the media were observed (data not shown).

TABLE 8

Effects of Position and Orientation of parB locus and FkpA Chaperone on Fab Expression Titer.

| Strain | Plasmid | Position | | Orientation | |
| --- | --- | --- | --- | --- | --- |
| | | Upstream | Downstream | FkpA | parB |
| 2909 | p134 | FkpA | parB | For | For |
| 3004 | p199 | FkpA | parB | Rev | For |
| 3005 | p200 | parB | FkpA | For | For |
| 3006 | p201 | parB | FkpA | Rev | For |

Example 14: Effect of Host Strain on Anti-CD3 Fab Titer and Product Quality

It is known in the literature that antibody Fabs when produced in *E. coli* are clipped by proteases in the periplasm under production conditions without any unnatural amino acid insertion (Battersby, J. E. et. al., Journal of Chromatography A, 927, 61, 2001). To investigate how Fab product quality is affected by an orthogonal amber suppression system, a Fab capture column was developed, by cation exchange using Capto S resin, which captures the intact Fab as well as several additional fragments. Proteins from strain 2886 harboring plasmid p119 (Tablet) with parB locus were utilized for this study.

Figure 12:
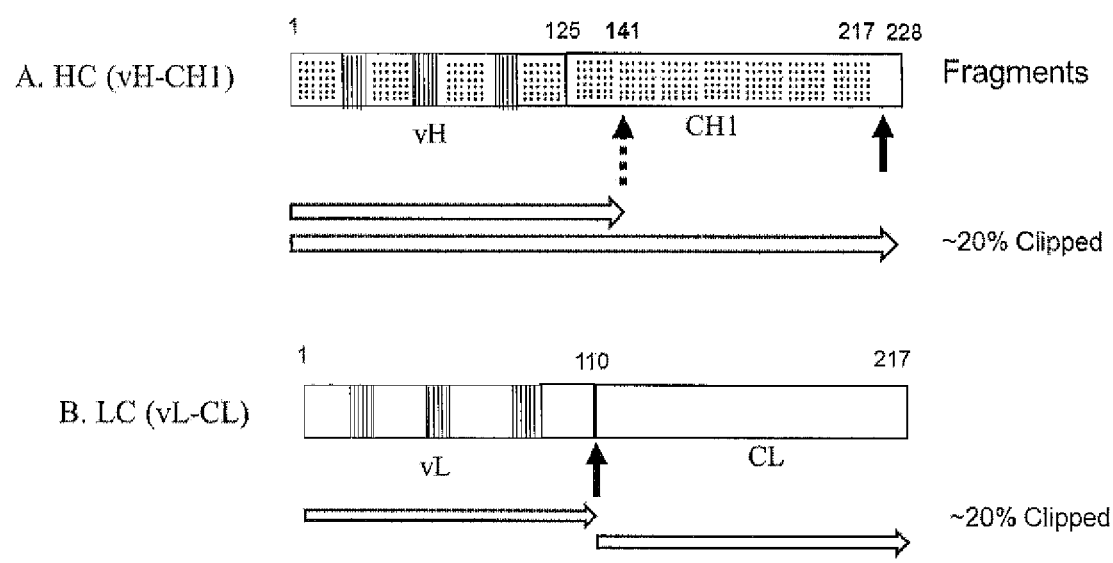
FIGS. 12A-B. Schematic of various translationally truncated (dotted arrow) and proteolytically clipped (solid arrow) fragments of Fab heavy chain (FIG. 12A) and light chain (FIG. 12B) from strain 2886, captured in a Capto S column elution fraction. In this strain, typical intact Fab recovery was between 20-25% of total captured proteins.

Analytical characterization of the Capto S elution pool by RP-HPLC plus mass spectroscopy (MS) from strain 2886 revealed two captured fragments to be proteolytically clipped HC and LC Fab fragments consistent with the literature report (Battersby, J. E. et. al., Journal of Chromatography A, 927, 61, 2001), and one additional translationally truncated HC fragment since the amber stop codon is located at the HC (FIGS. 12A-B). Intact Fab was found to be only ~20% of the captured protein by $A_{280}$ absorbance percent area from RP-HPLC on Capto S pool. The remaining Fab fragments captured were clipped light chain from the N-terminus (aa 1 to 110) (~20%), clipped heavy chain from the N-terminus (~20%) (aa 1 to 217), and heavy chain truncated at the amber stop codon at HK129 position for pAcF incorporation (~40%) (aa 1 to 141) (FIGS. 12A-B). The only fragment that was not captured in this Capto S column was the C-terminal light chain clipped fragment (aa 111 to 217).

Example 15: Design, Engineering and Expression Analysis of Vectors with Various Heavy Chain Extensions Construction of the heavy chain (HC) C-terminal extension strains: As disclosed in the above Examples, RP-HPLC and intact mass on Capto S elution pool identified various Fab fragments that were present at high percentages of total Fab protein, A likely protease responsible for Fab cleavage is the periplasmic serine endo-protease Prc (for processing of C-terminus), also known as tail-specific protease (Tsp) (Chen C. et al., Biotechnology and Bioengineering, 85, 463, 2004). Prc is believed to recognize and bind to the C-terminus of a protein and then cleave at loose or unfolded regions within the protein sequence (Keiler et al., Protein Science, 4, 1507, 1995). The site of cleavage is determined by protein secondary or tertiary structure and not primary sequence, and Prc therefore has a broad sequence specificity with respect to the proteolysis site. It has been shown, however, that a protein's C-terminal sequence affects its cleavage by Prc, and that modifying a protein's C-terminal sequence can change the amount of cleavage of that protein by Prc (Keiler K. C. & Sauer R. T., The Journal of Biological Chemistry, 271, 2589, 1996).

In this study, the Fab heavy chain C-terminal sequences were modified with the goal of reducing Prc C-terminal binding and thereby reducing Prc cleavage. This strategy was sought to improve the purity of the starting material of the Capto S capture column for purification, as well as to increase the intact Fab titer by decreasing the percentage of HC generated as clipped species thereby increasing the HC amount available for assembly into intact Fab. In the Fab design, the heavy chain sequence ended with $KSC^{220}$ where $C^{220}$ is implicated in the only inter-chain disulphide bond formation with the light chain. Unlike the light chain (LC) sequence which ends at $C^{214}$, natural HC sequence extends beyond the CH1 domain in the Fab fragment into the hinge region, CH2 domain and finally ends at the CH3 domain. To determine whether the Prc recognition at the HC C-terminal sequence could be altered by extending it beyond the $C^{220}$ residue based on the criteria reported in the literature (Keiler K. C. & Sauer R. T., The Journal of Biological Chemistry, 271, 2589, 1996), several heavy chain sequence variants were designed by extending the C-terminus from 1 to 5 amino acids (see Table 2) with the sequence $D^{221}KTHT^{225}$, the natural sequence into the hinge region. Variants with the $T^{225}$ to $L^{225}$ substitution (Table 2), reported for Genentech's Lucentis Fab (Ranibizumab), were also designed (see on the worldwideweb drugbank.ca/drugs/DB01270). The cell lines used in this study all had parB locus and the FkpA chaperone co-expressed off the anti-CD3 Fab plasmid, as 2909 (anti-CD3 Fab, parB-ZraI-F, fkpA).

Figure 13A:
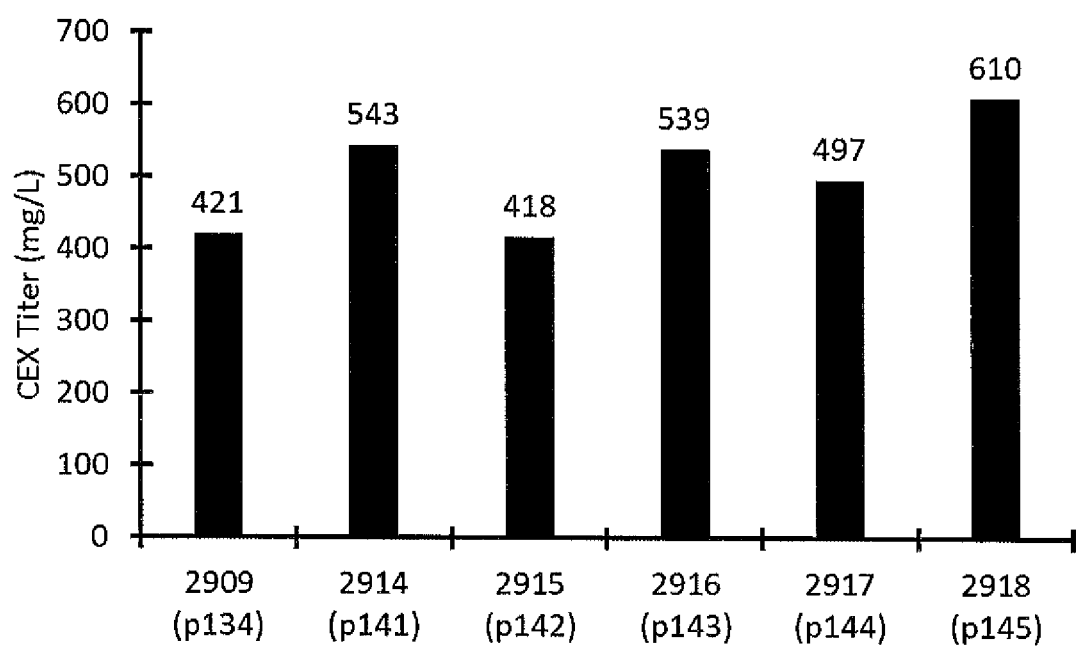
FIGS. 13A-B. Recoverable titers (FIG. 13A) and purity analysis (FIG. 13B) of various heavy chain (HC) carboxy-terminal (C-term) extension variants. New strains 2914 to 2918 (harboring plasmid p141 to p145 respectively) are compared with control strain 2909 (harboring plasmid p134) without any HC C-terminal extension.

Testing the effects of HC C-terminal extensions: A set of 50 mL samples were purified by Capto S column, with recoverable titer estimated by Capto S $A_{280}$ recovery times RP-HPLC purity on Capto S pool (FIG. 13A). RP-HPLC purity results on Capto S pools from the 50 mL purifications are shown in FIG. 13B.

All 5 heavy chain C-terminal extension variants gave higher recoverable titers when compared to control 2909, up to 610 mg/L for 2918 (FIG. 13A). These heavy chain variants also showed a higher percentage of intact Fab in the Capto S pool than control 2909 (30% to 42% intact for heavy chain variants vs. 25% intact for control 2909, FIG. 13B). Surprisingly, while there was a small decrease in percentage of clipped heavy chain species (as expected from reduced Prc proteolysis), a larger reduction was seen in the percentage of truncated heavy chain (31% to 38% truncated for heavy chain variants vs. 39% truncated for control 2909). This suggests that not all of the "truncated" HC species are necessarily from the results of low suppression efficiency and pAcF incorporation, and that some of these species could be due to proteolysis as well. Alternatively, the change in heavy chain C-terminal sequence could be independently affecting the suppression efficiency.

While the heavy chain C-terminal extension variants did show higher titers and higher percentage of intact Fab, suggesting that binding and proteolysis by Prc was reduced, there was not a direct correlation between percentage of intact Fab and Fab titers. Of the heavy chain extension variants, 2918 had the highest recoverable titer (610 mg/L) but lowest percentage of intact Fab (30%). There are many variables that affect the titer, and changing the protein sequence may, for example, be affecting the expression, secretion to periplasm, folding including cis-trans proline isomerization and disulfide bond formation in addition to affecting proteolysis by Prc.

Figure 13B:
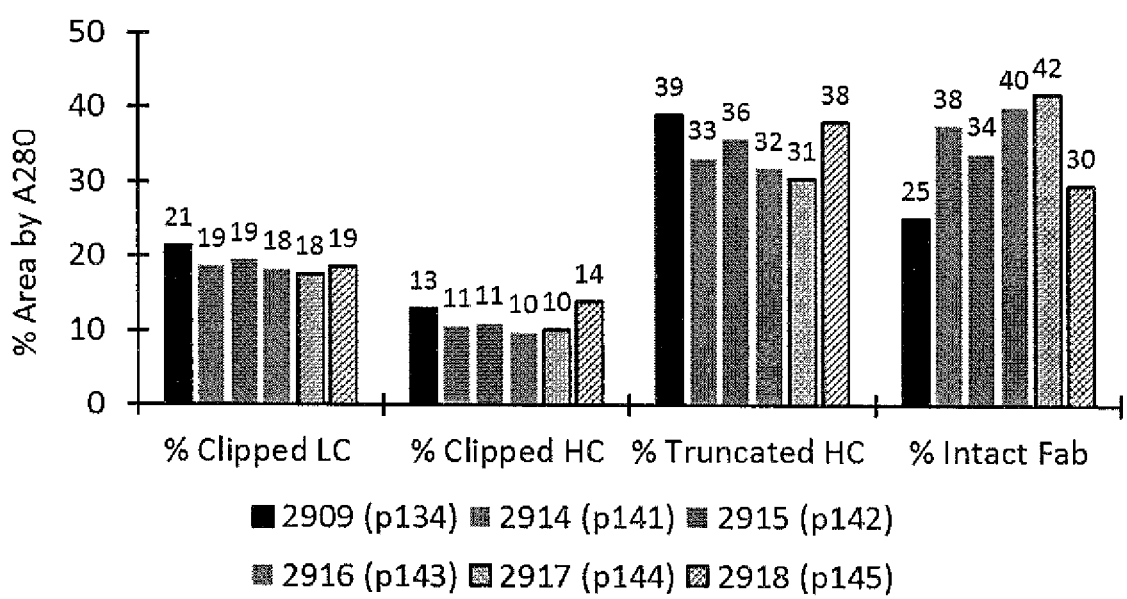

As can be seen in FIG. 13B, 2917 with heavy chain C-terminal sequence $KSC^{220}DKTHT^{225}$ had the lowest percentages of clipped LC, clipped HC and truncated HC fragments concomitant with the highest percentage of intact Fab titer. Even though strain 2917 Fab titer was lower compared to other variants, this strain was selected, due to better overall protein quality, to move forward for further process development, cell line generation and in vivo studies.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions disclosed and described herein belong. Although any methods, devices, and materials similar or equivalent to those described herein can be used in the practice or testing of the inventions described herein, the preferred methods, devices and materials are now described.

All publications and patents mentioned herein are incorporated herein by reference in their entirety for the purpose of describing and disclosing, for example, the constructs and methodologies that are described in the publications, which might be used in connection with the presently described inventions. The publications discussed herein are provided solely for their disclosure prior to the filing date of the present application. Nothing herein is to be construed as an admission that the inventors described herein are not entitled to antedate such disclosure by virtue of prior invention or for any other reason.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described herein can be used in various combinations. It is understood that the examples and embodiments described herein are for illustrative purposes only and that various modifications or changes in light thereof will be suggested to persons skilled in the art and are to be included within the spirit and purview of this application and scope of the appended claims.

INCORPORATION BY REFERENCE

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A vector for expressing a recombinant protein comprising a site-specifically incorporated non-naturally encoded amino acid in *Escherichia coli* (*E. coli*), comprising: (i) a nucleic acid sequence encoding the recombinant protein; and (ii) a nucleic acid sequence comprising a partition B (parB) locus having the nucleobase sequence of SEQ ID NO: 12, wherein the recombinant protein is an antibody or an antibody fragment, and wherein the parB locus is positioned in:
   a) a reverse transcriptional orientation and upstream relative to the nucleic acid sequence encoding the recombinant protein;
   b) a forward transcriptional orientation and downstream relative to the nucleic acid sequence encoding the recombinant protein; or
   c) a reverse transcriptional orientation and downstream relative to the nucleic acid sequence encoding the recombinant protein.

2. The vector of claim 1, comprising a nucleic acid sequence having an Afe1 restriction enzyme site upstream of the nucleic acid sequence encoding the recombinant protein, wherein the parB locus is positioned at the Afe1 restriction enzyme site in a reverse transcriptional orientation relative to the nucleic acid sequence encoding the recombinant protein.

3. The vector of claim 1, comprising a nucleic acid sequence having a Zra1 restriction enzyme site downstream of the nucleic acid sequence encoding the recombinant protein, wherein the parB locus is positioned at the Zra1 restriction enzyme site in a forward or reverse transcriptional orientation relative to the nucleic acid sequence encoding the recombinant protein.

4. The vector of claim 1, comprising a nucleic acid sequence encoding a chaperone.

5. The vector of claim 4, wherein the chaperone is a Skp chaperone having the amino acid sequence of SEQ ID NO: 18 or a FkpA chaperone having the amino acid sequence of SEQ ID NO: 16.

6. The vector of claim 5, wherein the Skp or FkpA chaperone is positioned in a forward or reverse transcriptional orientation relative to the parB locus.

7. The vector of claim 5, wherein the Skp or FkpA chaperone is positioned upstream or downstream relative to the parB locus.

8. The vector of claim 4, wherein the nucleic acid sequence encoding the recombinant protein, the nucleic acid sequence comprising the parB locus, and the nucleic acid sequence encoding the chaperone are included in a single expression plasmid having a native promoter.

9. The vector of claim 4, comprising a nucleic acid sequence encoding a Skp chaperone having the amino acid sequence of SEQ ID NO: 18 and a FkpA chaperone having the amino acid sequence of SEQ ID NO: 16.

10. The vector of claim 1, wherein the antibody fragment is a Fab antibody fragment comprising a heavy chain C-terminal extension.

11. The vector of claim 10, wherein the heavy chain C-terminal extension comprises 1, 2, 3, 4, or 5 amino acids.

12. The vector of claim 1, wherein the antibody or antibody fragment targets HER2, CD-70, PSMA, 5T4, EGFR, TROP2, CD3, IL-2, IL-3, IL-10, IL-12, IL-15, IL-21, GPC3, DLL3, ROR1, leptin, ghrelin, FGF-1, FGF-19, FGF-21, FGF-23, HGH, FcR, insulin, IGF1, TNFR1, TRAIL, or EPO.

13. The vector of claim 1, wherein the antibody is an IgG 1, IgG2, IgG3, or IgG4 antibody.

14. The vector of claim 1, wherein the antibody fragment is a Fab, a Fab', a F(ab')2, a Fv fragment, a single chain antibody fragment (scFv), a disulfide stabilized scFv (dsFv)), a diabody (Db), a BiTE (bispecific T-cell Engager), a DART (Dual Affinity Re-Targeting), or a Tandem Diabody (TandAb).

15. The vector of claim 14, wherein the antibody fragment is a Fab.

16. The vector of claim 14, wherein the antibody fragment is an anti-CD3 Fab.

17. The vector of claim 16, wherein the anti-CD3 Fab has a para-acetyl phenylalanine site-specifically incorporated at the lysine (K) residue at position 129 of the heavy-chain constant domain (CH1).

18. A bacterial cell or cell line comprising the vector of claim 1, wherein the bacterial cell or cell line is an *Escherichia coli* cell or cell line.

19. A method of producing a recombinant protein comprising a site-specifically incorporated non-naturally encoded amino acid, the method comprising expressing the recombinant protein in an *E. coli* bacterial cell from the vector of claim 1, wherein the recombinant protein is an antibody or an antibody fragment.

20. The method of claim 19 wherein the yield of the recombinant protein comprising a site-specifically incorporated non-naturally occurring encoded amino acid is increased by at least 0.2-fold.

21. The method of claim 19, wherein the non-naturally encoded amino acid is O-methyl-L-tyrosine, L-3-(2-naphthyl) alanine, 3-methyl-phenylalanine, O-4-allyl-L-tyrosine, 4-propyl-L-tyrosine, p-propargyloxy-L-phenylalanine, tri-O-acetyl-GlcNAcβ-serine, L-Dopa, a fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, phenylalanine, isopropyl-L-phenylalanine, para-acetyl p-nitrophenylalanine, p-sulfotyrosine, p-carboxyphenylalanine, o-nitrophenylalanine, m-nitrophenylalanine, p-boronyl phenylalanine, o-boronylphenylalanine, m-boronylphenylalanine, p-aminophenylalanine, o-aminophenylalanine, m-aminophenylalanine, p-acylphenylalanine, o-acylphenylalanine, m-acylphenylalanine, p-OMe phenylalanine, o-OMe phenylalanine, m-OMe phenylalanine, p-sulfophenylalanine, o-sulfophenylalanine, m-sulfophenylalanine, 5-nitro His, 3-nitro Tyr, 2-nitro Tyr, nitro substituted Leu, nitro substituted His, nitro substituted De, nitro substituted Trp, 2-nitro Trp, 4-nitro Trp, 5-nitro Trp, 6-nitro Trp, 7-nitro Trp, 3-aminotyrosine, 2-aminotyrosine, O-sulfotyrosine, 2-sulfooxyphenylalanine, 3-sulfooxyphenylalanine, o-carboxyphenylalanine, m-carboxyphenylalanine, p-acetyl-L-phenylalanine, or p-propargyl-phenylalanine.

22. The method of claim 21, wherein the non-naturally encoded amino acid is p-acetyl-L-phenylalanine.

* * * * *